(12) United States Patent
Ved

(10) Patent No.: US 12,296,050 B2
(45) Date of Patent: May 13, 2025

(54) PHARMACEUTICAL COMPOSITIONS COMPRISING MARALIXIBAT AND USES THEREOF

(71) Applicant: Mirum Pharmaceuticals, Inc., Foster City, CA (US)

(72) Inventor: Parag Ved, Foster City, CA (US)

(73) Assignee: MIRUM PHARMACEUTICALS, INC., Foster City, CA (US)

( * ) Notice: Subject to any disclaimer, the term of this patent is extended or adjusted under 35 U.S.C. 154(b) by 0 days.

(21) Appl. No.: 18/377,216

(22) Filed: Oct. 5, 2023

(65) Prior Publication Data
US 2025/0114310 A1   Apr. 10, 2025

(51) Int. Cl.
| | |
|---|---|
| A61K 9/20 | (2006.01) |
| A61K 31/4995 | (2006.01) |
| A61K 47/10 | (2017.01) |
| A61K 47/12 | (2006.01) |
| A61K 47/18 | (2017.01) |
| A61K 47/22 | (2006.01) |

(52) U.S. Cl.
CPC .......... *A61K 9/2054* (2013.01); *A61K 9/2009* (2013.01); *A61K 9/2031* (2013.01); *A61K 31/4995* (2013.01); *A61K 47/10* (2013.01); *A61K 47/12* (2013.01); *A61K 47/183* (2013.01); *A61K 47/22* (2013.01)

(58) Field of Classification Search
CPC .. A61K 9/2054; A61K 9/2009; A61K 9/2031; A61K 31/4995; A61K 47/10; A61K 47/12; A61K 47/183; A61K 47/22
See application file for complete search history.

(56) References Cited

U.S. PATENT DOCUMENTS

| | | | |
|---|---|---|---|
| 10,709,755 B2 * | 7/2020 | Ando | A61P 7/00 |
| 11,185,519 B2 | 11/2021 | Hanf | |
| 2006/0193910 A1 * | 8/2006 | Bernigal | A61K 9/1694 |
| | | | 264/109 |
| 2009/0142404 A1 | 6/2009 | Appel et al. | |
| 2011/0129530 A1 | 6/2011 | Venkatesh et al. | |
| 2012/0269891 A1 | 10/2012 | McKearn et al. | |
| 2014/0275090 A1 | 9/2014 | Gedulin et al. | |
| 2017/0143783 A1 * | 5/2017 | Ando | A61P 7/02 |
| 2020/0375989 A1 * | 12/2020 | Jaecklin | A61K 38/05 |
| 2023/0190743 A1 | 6/2023 | Vig et al. | |

FOREIGN PATENT DOCUMENTS

WO   WO-2022074681 A1 *   4/2022   ............... A61K 9/00

OTHER PUBLICATIONS

International Search Report and Written Opinion mailed Feb. 20, 2024 in connection with PCT/US23/034580.

* cited by examiner

*Primary Examiner* — Robert A Wax
*Assistant Examiner* — Olga V. Tcherkasskaya
(74) *Attorney, Agent, or Firm* — Troutman Pepper Locke LLP

(57) ABSTRACT

The invention relates to a pharmaceutical composition comprising maralixibat, or a pharmaceutically acceptable salt thereof, as the active ingredient. The invention further relates to the use of the pharmaceutical composition as a solid dosage drug product. The invention also relates to the use of the pharmaceutical composition and the solid dosage drug product described herein for treating cholestatic pruritus and cholestatic liver disease.

28 Claims, 21 Drawing Sheets

PHARMACEUTICAL COMPOSITIONS COMPRISING MARALIXIBAT AND USES THEREOF

FIELD

The present invention relates to pharmaceutical compositions and dosage forms comprising maralixibat, methods of administering the same, methods of preparing the same, and methods of treating cholestatic pruritus and cholestatic liver disease comprising administering pharmaceutical compositions and oral dosage forms of maralixibat.

BACKGROUND

Hypercholemia and cholestatic liver diseases are liver diseases associated with impaired bile secretion (i.e., cholestasis), associated with and often secondary to the intracellular accumulation of bile acids/salts in the hepatocyte. Hypercholemia is characterized by increased serum concentration of bile acid or bile salt. Cholestasis can be categorized clinicopathologically into two principal categories of obstructive, often extrahepatic, cholestasis, and nonobstructive, or intrahepatic, cholestasis. Nonobstructive intrahepatic cholestasis can further be classified into two principal subgroups of primary intrahepatic cholestasis that result from constitutively defective bile secretion, and secondary intrahepatic cholestasis that result from hepatocellular injury. Primary intrahepatic cholestasis includes diseases such as benign recurrent intrahepatic cholestasis, which is predominantly an adult form with similar clinical symptoms, and progressive familial intrahepatic cholestasis (PFIC) types 1, 2, 3, 4, 5, and 6, which are diseases that affect children.

Alagille syndrome is an inherited condition in which bile builds up in the liver. One of the major features of Alagille syndrome is liver damage caused by abnormalities in the bile ducts. Alagille syndrome is associated with abnormalities of the liver, heart, skeleton, eye, and kidneys and a characteristic facial appearance.

Cholestatic pruritus is an itching sensation that can lead to excessive scratching, rashes or lesions caused by scratching, sleep deprivation, depression, and suicidal ideations. Cholestatic pruritus is a symptom of cholestasis, which is the obstructing or disrupting of bile flow through the biliary system. This can be caused from problems in the liver, gallbladder, and/or biliary tract. These problems can be caused by biliary stricture, bile duct obstructions, liver diseases, hepatitis, pregnancy, parenteral nutrition, and medications. It may be caused by Alagille syndrome.

Maralixibat (as maralixibat chloride) is currently the only approved medication to treat pruritus in people with Alagille syndrome. It is known that maralixibat chloride inhibits apical sodium co-dependent bile acid transport (U.S. Pat. No. 5,994,391). Maralixibat is currently available as an oral solution.

There is a need for formulations and dosage forms of maralixibat having favorable dissolution and pharmacokinetic profiles, which also demonstrate good storage stability. Embodiments of the present disclosure are directed to this and other considerations.

SUMMARY

Provided herein is a pharmaceutical composition comprising maralixibat, or a pharmaceutically acceptable salt thereof, and:
  (i) a diluent;
  (ii) a glidant;
  (iii) a lubricant; and optionally
  (iv) a disintegrant.

Also provided herein is a pharmaceutical composition comprising maralixibat, or a pharmaceutically acceptable salt thereof, and:
  (i) a diluent;
  (ii) a glidant;
  (iii) a lubricant; and
  (iv) a disintegrant.

Also provided herein is a composition comprising about 10.5% (w/w) maralixibat chloride and
  (i) about 62.5% (w/w) microcrystalline cellulose (MCC) and about 23.5% (w/w) lactose monohydrate;
  (ii) about 0.5% (w/w) silicon dioxide; and
  (iii) about 3% (w/w) Poloxamer 188.

Also provided herein is a composition comprising about 10.5% (w/w) maralixibat chloride and
  (i) about 62.5% (w/w) MCC and about 23.5% (w/w) lactose monohydrate;
  (ii) about 0.5% (w/w) silicon dioxide; and
  (iii) about 3% (w/w) PEG 8000.

Further provided herein is an oral dosage form comprising about 5 mg to about 50 mg maralixibat, or a pharmaceutically acceptable salt thereof, based on the free base weight of maralixibat, and one or more excipients, wherein:
  about 100% of maralixibat, or a pharmaceutically acceptable salt thereof, dissolves in an acidic pH environment of a pH less than about 5.0; and
  upon pH increase from the acidic pH environment to a pH of about 6.0 to about 7.4, at least about 65% of maralixibat, or a pharmaceutically acceptable salt thereof, remains dissolved for at least about 1 hour.

In one embodiment, the oral dosage form as described above is formulated for once-daily or twice-daily administration.

Also provided herein is a method of administering maralixibat, or a pharmaceutically acceptable salt thereof, to a subject in need thereof, comprising administering to the subject the dosage form as described herein.

Further provided herein is a method of preparing the pharmaceutical composition as described herein, comprising:
  milling maralixibat, or a pharmaceutically acceptable salt thereof;
  combining the milled maralixibat, or a pharmaceutically acceptable salt thereof, with the diluent, the glidant, the lubricant; and optionally the disintegrant to form an admixture; and compacting the admixture to form the pharmaceutical composition.

Also provided herein is a method of treating cholestatic pruritus in a subject in need thereof, comprising administering to the subject a therapeutically effective amount of the pharmaceutical composition as described herein.

Also provided herein is a method of treating cholestatic liver disease or condition in a subject in need thereof, comprising administering to the subject a therapeutically effective amount of the pharmaceutical composition as described herein.

Further provided herein is a method of preparing the dosage form as described herein, comprising:
  milling maralixibat, or a pharmaceutically acceptable salt thereof;
  combining the milled maralixibat, or a pharmaceutically acceptable salt thereof, with the diluent, the glidant, the lubricant; and optionally the disintegrant to form an admixture; and compacting the admixture to form the dosage form.

Also provided herein is a method of treating cholestatic pruritus in a subject in need thereof, comprising administering to the subject the dosage form as described herein.

Also provided herein is a method of treating cholestatic liver disease or condition in a subject in need thereof, comprising administering to the subject the dosage form as described herein.

DETAILED DESCRIPTION

Figure 1:
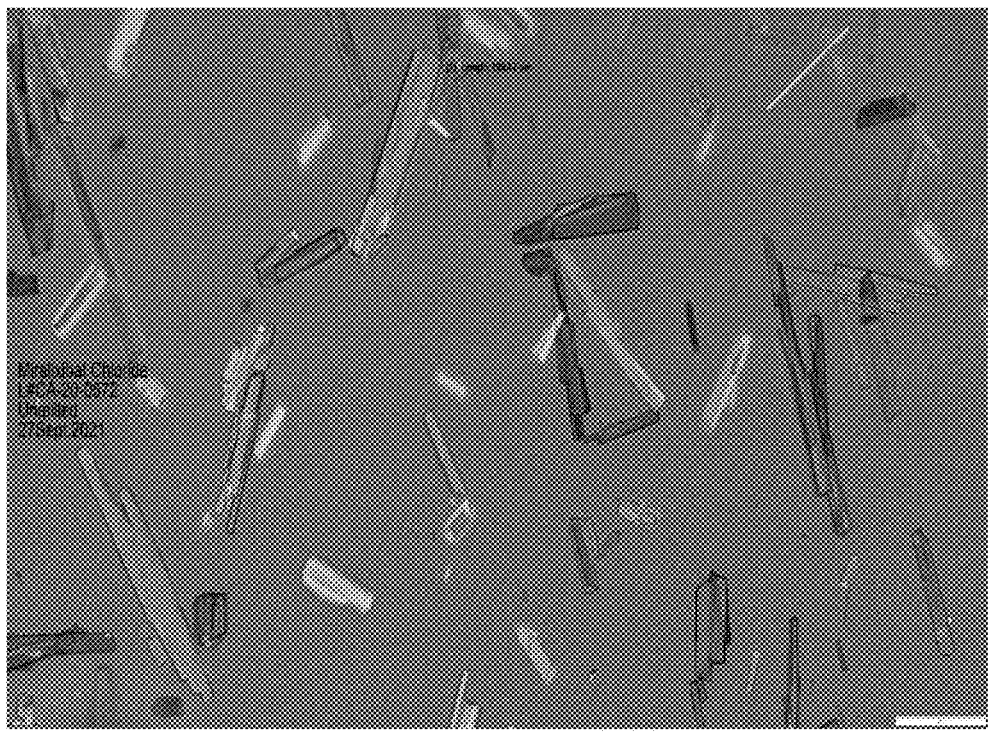
FIG. 1 shows maralixibat chloride active pharmaceutical ingredient (API) before milling.
Figure 2:
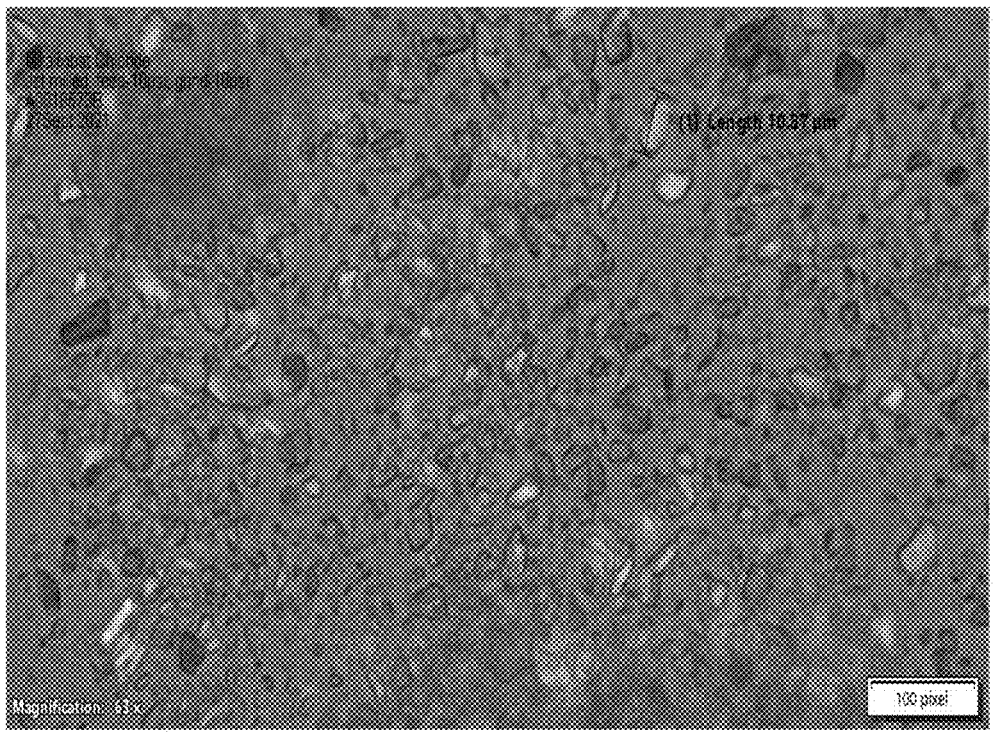
FIG. 2 shows maralixibat chloride API after jet milling at a feed pressure of 10 psi and a grind pressure of 10 psi.
Figure 3:
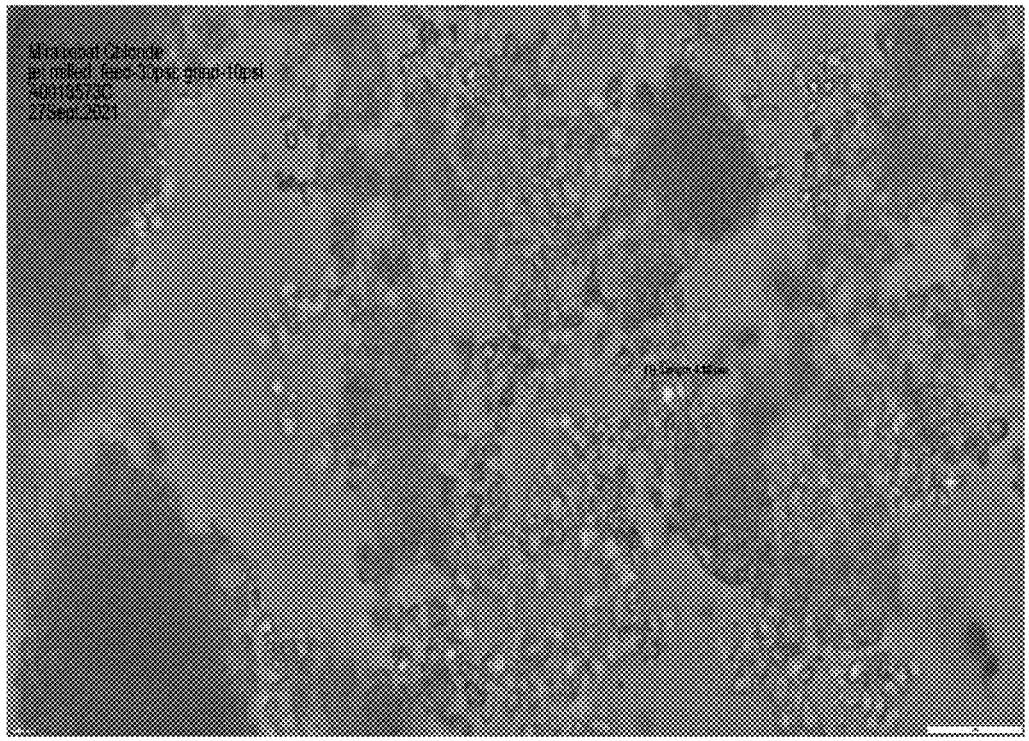
FIG. 3 shows maralixibat chloride API after jet milling at a feed pressure of 30 psi and a grind pressure of 10 psi.
Figure 4:
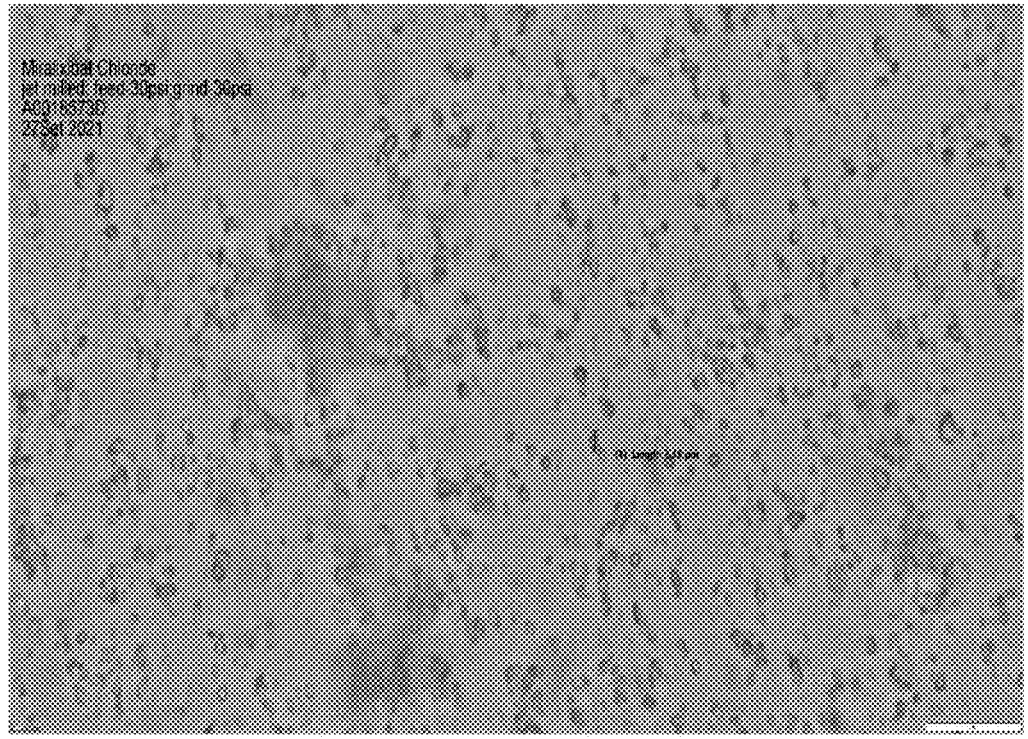
FIG. 4 shows maralixibat chloride API after jet milling at a feed pressure of 30 psi and a grind pressure of 30 psi.

Unless defined otherwise, all technical and scientific terms have the same meaning as is commonly understood by one of ordinary skill in the art to which the embodiments disclosed belong.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "active pharmaceutical ingredient" or "API" refers to a biologically active compound. Exemplary APIs include maralixibat or a pharmaceutically acceptable salt, hydrate, or solvate thereof. Maralixibat is sold under the trademark of Livmarli®, and known as SHP625, LUM001, lopixibat, or 1-[[4-[[4-[(4R,5R)-3,3-dibutyl-7-(dimethylamino)-2,3,4,5-tetrahydro-4-hydroxy-1,1-dioxido-1-benzothiepin-5-yl]phenoxy]methyl]phenyl]methyl]-4-aza-1-azoniabicyclo[2.2.2]octane. The structure of maralixibat in the free base form is shown below:

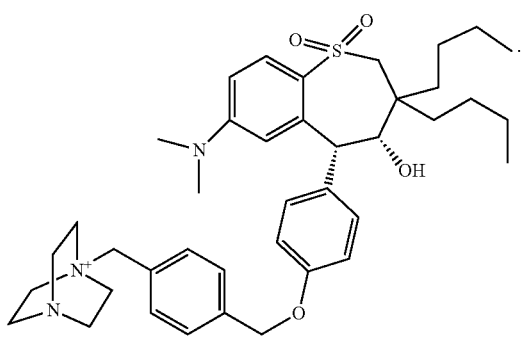 [SMILES: CCCCC1(CCCC)CS(=O)(=O)c2ccc(N(C)C)cc2[C@@H](c2ccc(OCc3ccc(C[N+]45CCN(CC4)CC5)cc3)cc2)[C@H]1O]

The structure of maralixibat chloride is shown below:

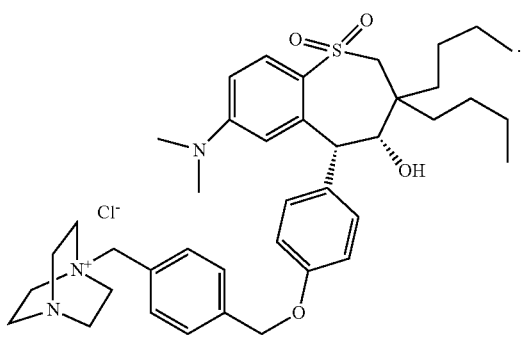 [SMILES: CCCCC1(CCCC)CS(=O)(=O)c2ccc(N(C)C)cc2[C@@H](c2ccc(OCc3ccc(C[N+]45CCN(CC4)CC5)cc3)cc2)[C@H]1O ; [Cl-]]

In the present disclosure, "MRX" refers to maralixibat. In the present disclosure, "maralixibat salt" or "MRX salt" refers to maralixibat chloride.

As used herein, "Ac-Di-Sol©" refers to the trademark that identifies the source of croscarmellose sodium, which is cross-linked sodium carboxymethyl cellulose.

As used herein, the term "animal" includes, but is not limited to, humans and non-human vertebrates such as wild, domestic, and farm animals.

As used herein, the term "Avicel®", "Avicel® PH-302", or "Avicel® PH-102" refers to the trademark that identifies the source of microcrystalline cellulose (MCC).

In the present disclosure, the weight or weight percentage of "maralixibat, or a pharmaceutically acceptable salt thereof" is based on the weight of the free base of maralixibat. When the salt form of maralixibat is specified and the weight or the weight percentage of the salt is specifically indicated, for example, in a "composition of comprising about 10.5% (w/w) maralixibat chloride", the weight percentage is based on the weight of the maralixibat chloride.

As used herein, a "binder" is an excipient that imparts a pharmaceutical composition with enhanced cohesion or tensile strength (e.g., hardness).

As used herein, "Cab-O-Sil©" refers to the trademark that identifies the source of silicon dioxide.

As used herein, the term "composition" generally refers to a composition of two or more components, usually one or more drugs (e.g., maralixibat or a pharmaceutically acceptable salt) and one or more pharmaceutical excipients.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "Compritol® 888 ATO" or "Compritol® 888" refers to the trademark that identifies the source of a glyceride, known as glyceryl dibehenate, comprised of a blend of behenic acid esters with glycerol.

As used herein, a "disintegrant" is an excipient that hydrates a pharmaceutical composition and aids in tablet dispersion.

As used herein, a "diluent" or "filler" is an excipient that adds bulkiness to a pharmaceutical composition.

As used herein, "DS" refers to drug substance.

As used herein, "dv90" refers to the point in the size distribution wherein 90% of the total volume of material in the sample falls below (e.g., if the dv90 is 850 nm, then 90% of the sample has a size of 850 nm or smaller).

As used herein, an "excipient" includes functional and non-functional ingredients in a pharmaceutical composition.

As used herein, the term "fasted" is defined as follows: the dosing state which is defined following an overnight fast (wherein 0 caloric intake has occurred) of at least 10 hours (i.e., >10 hours). Subjects may administer the dosage form with 240 mL of water. No food should be allowed for at least 4 hours post-dose. Water may be allowed as desired except for one hour before and after drug administration.

As used herein, a "glidant" is an excipient that imparts a pharmaceutical composition with enhanced flow properties.

As used herein, the term "hydroxy" or "hydroxyl" means an —OH group.

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, a "loop mill" refers to a "mill" that performs "loop milling" which is a process that uses pressurized gas to create high particle velocity and high-energy impact between particles and between the particles and the mill chamber.

As used herein, a "lubricant" is an excipient that is added to pharmaceutical compositions that are pressed into tablets. The lubricant aids in compaction of granules into tablets and ejection of a tablet of a pharmaceutical composition from a die press.

As used herein, "Lubritab®" refers to the trademark that identifies the source of hydrogenated cottonseed oil (a plant-derived lubricant).

As used herein, "lactose FF316" or "lactose monohydrate FF316" refers to lactose monohydrate.

As used herein, "mill" refers to a device that breaks solid materials down through mechanical forces into smaller pieces. "Milling" refers to the process of breaking solid materials into smaller pieces.

As used herein, the term "PEG 8000" refers to polyethylene glycol with an average molecular weight of about 8000.

As used herein, the term "percent" or "%" means the weight percentage of the total weight of the composition (i.e., by weight of the total composition).

As used herein, a "pin mill" refers to a "mill" comprising two discs or plates each containing circular rows of pins or vertical projections that are arranged in concentric circles moving past one another. "Pin milling" refers to the process of particles repeatedly impacting pins as the material is fed into the space between the discs of the milling chamber.

As used herein, "Poloxamer 188" refers to a nonionic block copolymer comprised of poly(ethylene oxide) and poly(propylene oxide).

As used herein, "Precirol® ATO 5" or "Precirol©" refers to the trademark that identifies the source of glyceryl palmitostearate.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present embodiments include pharmaceutically acceptable salt of the compounds described herein. The present embodiments also include quaternary ammonium salts of the compounds described herein, where the compounds have one or more tertiary amine moieties.

As used herein, the term "relative humidity" or "RH" is a measure of a present state of how much water vapor is in a water-air mixture compared to the maximum amount possible given the same temperature.

As used herein, the term "solid dosage form" generally refers to a pharmaceutical composition, which when used in an oral mode of administration includes capsules, tablets, pills, powders and granules. In such solid dosage forms, the active compound is mixed with at least one inert, pharmaceutically acceptable excipient or carrier.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, elimination or amelioration of a disorder, or side-effects. The amount needed to elicit the therapeutic response can be determined based on the age, health, size and sex of the subject. Optimal amounts can also be determined based on monitoring of the subject's response to treatment.

As used herein, the term "treat," "treated," or "treating" means therapeutic treatment wherein the object is to slow down (lessen) an undesired physiological condition, disorder or disease, or obtain beneficial or desired clinical results. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment.

As used herein, the term "oral dosage form" generally refers to a pharmaceutical composition, which when used in an oral mode of administration include, but are not limited to, liquid dosage forms (e.g., solutions, elixers, suspensions, syrups, emulsions, aerosols, slurries, dispersions, and colloids) and solid dosage forms (e.g., capsules, tablets, pills, powders and granules). In such oral dosage forms, the active compound is mixed with at least one inert, pharmaceutically acceptable excipient or carrier.

As used herein, the term "percentage" or "%" of a component refers to the weight percentage (w/w) of the component, which is the weight of the component over the total weight of the composition.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

It is understood that the present embodiments encompass the use, where applicable, of stereoisomers, diastereomers and optical stereoisomers of the compounds, as well as mixtures thereof. Additionally, it is understood that stereoisomers, diastereomers, and optical stereoisomers of the compounds, and mixtures thereof, are within the scope of the embodiments. By way of non-limiting example, the mixture may be a racemate or the mixture may comprise unequal proportions of one particular stereoisomer over the other. Additionally, the compounds can be provided as substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the embodiments unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present embodiments. Cis and trans geometric isomers of the compounds are also included within the scope of the embodiments and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, chiral HPLC and fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the embodiments. Substantial separation can include compositions containing at least about 50%, at least about 60%, at least about 70%, at least about 80%, at least about 90%, at least about 95%, at least about 97%, or at least about 99% by weight of the compound of the embodiments, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach TRL Press Oxford 1989) now allow the synthesis of homodisperse compounds with molecular weights approaching 5,000 Daltons. Other substitution patterns are equally effective.

The compounds also include derivatives referred to as prodrugs.

Embodiments of various compounds and salts thereof are provided. Where a variable is not specifically recited, the variable can be any option described herein, except as otherwise noted or dictated by context.

Pharmaceutical Compositions

Provided herein is a pharmaceutical composition comprising maralixibat, or a pharmaceutically acceptable salt thereof, and:
(i) a diluent;
(ii) a glidant;
(iii) a lubricant; and optionally
(iv) a disintegrant.

Also provided herein is a pharmaceutical composition comprising maralixibat, or a pharmaceutically acceptable salt thereof, and:
(i) a diluent;
(ii) a glidant;
(iii) a lubricant; and
(iv) a disintegrant.

The compositions can be in the form of tablets, pills, powders, lozenges, sachets, cachets, aerosols (as a solid), soft and hard gelatin capsules, and sterile packaged powders.

In some embodiments, the pharmaceutical composition of the invention is a solid dosage form, such as a tablet, a granule, a sachet, or a powder. Also provided are pharmaceutical compositions comprising a compound of the invention or a pharmaceutically acceptable salt thereof in the form of a dissolving tablet, a dissolving wafer, a capsule, or a gel capsule. In certain embodiments, solid dosage forms described herein comprise a solid vehicle (e.g., as used in a tablet), and/or a gaseous vehicle (e.g., as used in dry powder inhalation (DPI)).

In one embodiment, the composition is in a solid dosage form.

In an additional embodiment, the composition is formulated as a capsule, a pill, a cachet, a tablet, a granule, a multi-particulate, a mini-tablet, or powder.

In an additional embodiment, the composition is formulated as a tablet.

In some embodiments, a composition is in a unit dose formulation for oral, intranasal, or other administration to a patient. The term "unit dose", "unit dosage", or "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the composition comprises about 1 mg to about 250 mg maralixibat or a pharmaceutically acceptable salt thereof based on the free base weight of maralixibat. In some embodiments, the composition comprises about 1 mg to about 250 mg, about 1 mg to about 220 mg, about 1 mg to about 200 mg, about 1 mg to about 180 mg, about 1 mg to about 160 mg, about 1 mg to about 150 mg, about 1 mg to about 140 mg, about 1 mg to about 120 mg, about 1 mg to about 110 mg, about 1 mg to about 100 mg, about 1 mg to about 95 mg, about 1 mg to about 90 mg, about 1 mg to about 85 mg, about 1 mg to about 80 mg, about 1 mg to about 75 mg, about 1 mg to about 70 mg, about 1 mg to about 65 mg, about 1 mg to about 60 mg, about 1 mg to about 55 mg, about 1 mg to about 50 mg, about 1 mg to about 45 mg, about 1 mg to about 40 mg, about 1 mg to about 35 mg, about 1 mg to about 30 mg, about 1 mg to about 25 mg, about 1 mg to about 20 mg, about 1 mg to about 15 mg, about 1 mg to about 10 mg, about 1 mg to about 5 mg, about 5 mg to about 250 mg, about 5 mg to about 220 mg, about 5 mg to about 200 mg, about 5 mg to about 180 mg, about 5 mg to about 160 mg, about 5 mg to about 150 mg, about 5 mg to about 140 mg, about 5 mg to about 120 mg, about 5 mg to about 110 mg, about 5 mg to about 100 mg, about 5 mg to about 95 mg, about 5 mg to about 90 mg, about 5 mg to about 85 mg, about 5 mg to about 80 mg, about 5 mg to about 75 mg, about 5 mg to about 70 mg, about 5 mg to about 65 mg, about 5 mg to about 60 mg, about 5 mg to about 55 mg, about 5 mg to about 50 mg, about 5 mg to about 45 mg, about 5 mg to about 40 mg, about 5 mg to about 35 mg, about 5 mg to about 30 mg, about 5 mg to about 25 mg, about 5 mg to about 20 mg, about 5 mg to about 15 mg, about 5 mg to about 10 mg, about 10 mg to about 250 mg, about 10 mg to about 220 mg, about 10 mg to about 200 mg, about 10 mg to about 180 mg, about 10 mg to about 160 mg, about 10 mg to about 150 mg, about 10 mg to about 140 mg, about 10 mg to about 120 mg, about 10 mg to about 110 mg, about 10 mg to about 100 mg, about 10 mg to about 95 mg, about 10 mg to about 90 mg, about 10 mg to about 85 mg, about 10 mg to about 80 mg, about 10 mg to about 75 mg, about 10 mg to about 70 mg, about 10 mg to about 65 mg, about 10 mg to about 60 mg, about 10 mg to about 55 mg, about 10 mg to about 50 mg, about 10 mg to about 45 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 250 mg, about 15 mg to about 220 mg, about 15 mg to about 200 mg, about 15 mg to about 180 mg, about 15 mg to about 160 mg, about 15 mg to about 150 mg, about 15 mg to about 140 mg, about 15 mg to about 120 mg, about 15 mg to about 110 mg, about 15 mg to about 100 mg, about 15 mg to about 95 mg, about 15 mg to about 90 mg, about 15 mg to about 85 mg, about 15 mg to about 80 mg, about 15 mg to about 75 mg, about 15 mg to about 70 mg, about 15 mg to about 65 mg, about 15 mg to about 60 mg, about 15 mg to about 55 mg, about 15 mg to about 50 mg, about 15 mg to about 45 mg, about 15 mg to about 40 mg, about 15 mg to about 35 mg, about 15 mg to about 30 mg, about 15 mg to about 25 mg, about 15 mg to about 20 mg, about 20 mg to about 250 mg, about 20 mg to about 220 mg, about 20 mg to about 200 mg, about 20 mg to about 180 mg, about 20 mg to about 160 mg, about 20 mg to about 150 mg, about 20 mg to about 140 mg, about 20 mg to about 120 mg, about 20 mg to about 110 mg, about 20 mg to about 100 mg, about 20 mg to about 95 mg, about 20 mg to about 90 mg, about 20 mg to about 85 mg, about 20 mg to about 80 mg, about 20 mg to about 75 mg, about 20 mg to about 70 mg, about 20 mg to about 65 mg, about 20 mg to about 60 mg, about 20 mg to about 55 mg, about 20 mg to about 50 mg, about 20 mg to about 45 mg, about 20 mg to about 40 mg, about 20 mg to about 35 mg, about 20 mg to about 30 mg, about 20 mg to about 25 mg, about 25 mg to about 250 mg, about 25 mg to about 220 mg, about 25 mg to about 200 mg, about 25 mg to about 180 mg, about 25 mg to about 160 mg, about 25 mg to about 150 mg, about 25 mg to about 140 mg, about 25 mg to about 120 mg, about 25 mg to about 110 mg, about 25 mg to about 100 mg, about 25 mg to about 95 mg, about 25 mg to about 90 mg, about 25 mg to about 85 mg, about 25 mg to about 80 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 25 mg to about 35 mg, about 25 mg to about 30 mg, about 30 mg to about 250 mg, about 30 mg to about 220 mg, about 30 mg to about 200 mg, about 30 mg to about 180 mg, about 30 mg to about 160 mg, about 30 mg to about 150 mg, about 30 mg to about 140 mg, about 30 mg to about 120 mg, about 30 mg to about 110 mg, about 30 mg to about 100 mg, about 30 mg to about 95 mg, about 30 mg to about 90 mg, about 30 mg to about 85 mg, about 30 mg to about 80 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, about 30 mg to about 35 mg, about 35 mg to about 250 mg, about 35 mg to about 220 mg, about 35 mg to about 200 mg, about 35 mg to about 180 mg, about 35 mg to about 160 mg, about 35 mg to about 150 mg, about 35 mg to about 140 mg, about 35 mg to about 120 mg, about 35 mg to about 110 mg, about 35 mg to about 100 mg, about 35 mg to about 95 mg, about 35 mg to about 90 mg, about 35 mg to about 85 mg, about 35 mg to about 80 mg, about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg, about 35 mg to about 40 mg, about 40 mg to about 250 mg, about 40 mg to about 220 mg, about 40 mg to about 200 mg, about 40 mg to about 180 mg, about 40 mg to about 160 mg, about 40 mg to about 150 mg, about 40 mg to about 140 mg, about 40 mg to about 120 mg, about 40 mg to about 110 mg, about 40 mg to about 100 mg, about 40 mg to about 95 mg, about 40 mg to about 90 mg, about 40 mg to about 85 mg, about 40 mg to about 80 mg, about 40 mg to about 75 mg, about 40 mg to about 70 mg, about 40 mg to about 65 mg, about 40 mg to about 60 mg, about 40 mg to about 55 mg, about 40 mg to about 50 mg, about 40 mg to about 45 mg, about 45 mg to about 250 mg, about 45 mg to about 220 mg, about 45 mg to about 200 mg, about 45 mg to about 180 mg, about 45 mg to about 160 mg, about 45 mg to about 150 mg, about 45 mg to about 140 mg, about 45 mg to about 120 mg, about 45 mg to about 110 mg, about 45 mg to about 100 mg, about 45 mg to about 95 mg, about 45 mg to about 90 mg, about 45 mg to about 85 mg, about 45 mg to about 80 mg, about 45 mg to about 75 mg, about 45 mg to about 70 mg, about 45 mg to about 65 mg, about 45 mg to about 60 mg, about 45 mg to about 55 mg, about 45 mg to about 50 mg, about 50 mg to about 250 mg, about 50 mg to about 220 mg, about 50 mg to about 200 mg, about 50 mg to about 180 mg, about 50 mg to about 160 mg, about 50 mg to about 150 mg, about 50 mg to about 140 mg, about 50 mg to about 120 mg, about 50 mg to about 110 mg, about 50 mg to about 100 mg, about 50 mg to about 95 mg, about 50 mg to about 90 mg, about 50 mg to about 85 mg, about 50 mg to about 80 mg, about 50 mg to about 75 mg, about 50 mg to about 70 mg, about 50 mg to about 65 mg, about 50 mg to about 60 mg, about 50 mg to about 55 mg, about 55 mg to about 250 mg, about 55 mg to about 220 mg, about 55 mg to about 200 mg, about 55 mg to about 180 mg, about 55 mg to about 160 mg, about 55 mg to about 150 mg, about 55 mg to about 140 mg, about 55 mg to about 120 mg, about 55 mg to about 110 mg, about 55 mg to about 100 mg, about 55 mg to about 95 mg, about 55 mg to about 90 mg, about 55 mg to about 85 mg, about 55 mg to about 80 mg, about 55 mg to about 75 mg, about 55 mg to about 70 mg, about 55 mg to about 65 mg, about 55 mg to about 60 mg, about 60 mg to about 250 mg, about 60 mg to about 220 mg, about 60 mg to about 200 mg, about 60 mg to about 180 mg, about 60 mg to about 160 mg, about 60 mg to about 150 mg, about 60 mg to about 140 mg, about 60 mg to about 120 mg, about 60 mg to about 110 mg, about 60 mg to about 100 mg, about 60 mg to about 95 mg, about 60 mg to about 90 mg, about 60 mg to about 85 mg, about 60 mg to about 80 mg, about 60 mg to about 75 mg, about 60 mg to about 70 mg, about 60 mg to about 65 mg, about 65 mg to about 250 mg, about 65 mg to about 220 mg, about 65 mg to about 200 mg, about 65 mg to about 180 mg, about 65 mg to about 160 mg, about 65 mg to about 150 mg, about 65 mg to about 140 mg, about 65 mg to about 120 mg, about 65 mg to about 110 mg, about 65 mg to about 100 mg, about 65 mg to about 95 mg, about 65 mg to about 90 mg, about 65 mg to about 85 mg, about 65 mg to about 80 mg, about 65 mg to about 75 mg, about 65 mg to about 70 mg, about 70 mg to about 250 mg, about 70 mg to about 220 mg, about 70 mg to about 200 mg, about 70 mg to about 180 mg, about 70 mg to about 160 mg, about 70 mg to about 150 mg, about 70 mg to about 140 mg, about 70 mg to about 120 mg, about 70 mg to about 110 mg, about 70 mg to about 100 mg, about 70 mg to about 95 mg, about 70 mg to about 90 mg, about 70 mg to about 85 mg, about 70 mg to about 80 mg, about 70 mg to about 75 mg, about 75 mg to about 250 mg, about 75 mg to about 220 mg, about 75 mg to about 200 mg, about 75 mg to about 180 mg, about 75 mg to about 160 mg, about 75 mg to about 150 mg, about 75 mg to about 140 mg, about 75 mg to about 120 mg, about 75 mg to about 110 mg, about 75 mg to about 100 mg, about 75 mg to about 95 mg, about 75 mg to about 90 mg, about 75 mg to about 85 mg, about 75 mg to about 80 mg, about 80 mg to about 250 mg, about 80 mg to about 220 mg, about 80 mg to about 200 mg, about 80 mg to about 180 mg, about 80 mg to about 160 mg, about 80 mg to about 150 mg, about 80 mg to about 140 mg, about 80 mg to about 120 mg, about 80 mg to about 110 mg, about 80 mg to about 100 mg, about 80 mg to about 95 mg, about 80 mg to about 90 mg, about 80 mg to about 85 mg, about 85 mg to about 250 mg, about 85 mg to about 220 mg, about 85 mg to about 200 mg, about 85 mg to about 180 mg, about 85 mg to about 160 mg, about 85 mg to about 150 mg, about 85 mg to about 140 mg, about 85 mg to about 120 mg, about 85 mg to about 110 mg, about 85 mg to about 100 mg, about 85 mg to about 95 mg, about 85 mg to about 90 mg, about 90 mg to about 250 mg, about 90 mg to about 220 mg, about 90 mg to about 200 mg, about 90 mg to about 180 mg, about 90 mg to about 160 mg, about 90 mg to about 150 mg, about 90 mg to about 140 mg, about 90 mg to about 120 mg, about 90 mg to about 110 mg, about 90 mg to about 100 mg, about 90 mg to about 95 mg, about 95 mg to about 250 mg, about 95 mg to about 220 mg, about 95 mg to about 200 mg, about 95 mg to about 180 mg, about 95 mg to about 160 mg, about 95 mg to about 150 mg, about 95 mg to about 140 mg, about 95 mg to about 120 mg, about 95 mg to about 110 mg, about 95 mg to about 100 mg, about 100 mg to about 250 mg, about 100 mg to about 220 mg, about 100 mg to about 200 mg, about 100 mg to about 180 mg, about 100 mg to about 160 mg, about 100 mg to about 150 mg, about 100 mg to about 140 mg, about 100 mg to about 120 mg, about 100 mg to about 110 mg, about 110 mg to about 250 mg, about 110 mg to about 220 mg, about 110 mg to about 200 mg, about 110 mg to about 180 mg, about 110 mg to about 160 mg, about 110 mg to about 150 mg, about 110 mg to about 140 mg, about 110 mg to about 120 mg, about 120 mg to about 250 mg, about 120 mg to about 220 mg, about 120 mg to about 200 mg, about 120 mg to about 180 mg, about 120 mg to about 160 mg, about 120 mg to about 150 mg, about 120 mg to about 140 mg, about 140 mg to about 250 mg, about 140 mg to about 220 mg, about 140 mg to about 200 mg, about 140 mg to about 180 mg, about 140 mg to about 160 mg, about 140 mg to about 150 mg, about 150 mg to about 250 mg, about 150 mg to about 220 mg, about 150 mg to about 200 mg, about 150 mg to about 180 mg, about 150 mg to about 160 mg, about 160 mg to about 250 mg, about 160 mg to about 220 mg, about 160 mg to about 200 mg, about 160 mg to about 180 mg, about 180 mg to about 250 mg, about 180 mg to about 220 mg, about 180 mg to about 200 mg, about 200 mg to about 250 mg, about 200 mg to about 220 mg, or about 220 mg to about 250 mg maralixibat or a pharmaceutically acceptable salt thereof based on the free base weight of maralixibat.

In some embodiments, the composition comprises about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 140 mg, about 150 mg, about 160 mg, about 180 mg, about 200 mg, about 220 mg, or about 250 mg maralixibat or a pharmaceutically acceptable salt thereof based on the free base weight of maralixibat.

In another embodiment, the composition comprises about 5 mg to about 50 mg maralixibat or a pharmaceutically acceptable salt thereof based on the free base weight of maralixibat.

In another embodiment, the composition comprises about 5 mg, about 10 mg, about 30 mg, or about 50 mg maralixibat or a pharmaceutically acceptable salt thereof based on the free base weight of maralixibat.

In some embodiments, the composition comprises about 1% to about 90% (w/w) maralixibat or a pharmaceutically acceptable salt thereof. In some embodiments, the composition comprises about 1% to about 90%, about 1% to about 75%, about 1% to about 50%, about 1% to about 40%, about 1% to about 35%, about 1% to about 30%, about 1% to about 25%, about 1% to about 22%, about 1% to about 20%, about 1% to about 17%, about 1% to about 15%, about 1% to about 12%, about 1% to about 10%, about 1% to about 7%, about 1% to about 5%, about 1% to about 2%, about 2% to about 90%, about 2% to about 75%, about 2% to about 50%, about 2% to about 40%, about 2% to about 35%, about 2% to about 30%, about 2% to about 25%, about 2% to about 22%, about 2% to about 20%, about 2% to about 17%, about 2% to about 15%, about 2% to about 12%, about 2% to about 10%, about 2% to about 7%, about 2% to about 5%, about 5% to about 90%, about 5% to about 75%, about 5% to about 50%, about 5% to about 40%, about 5% to about 35%, about 5% to about 30%, about 5% to about 25%, about 5% to about 22%, about 5% to about 20%, about 5% to about 17%, about 5% to about 15%, about 5% to about 12%, about 5% to about 10%, about 5% to about 7%, about 7% to about 90%, about 7% to about 75%, about 7% to about 50%, about 7% to about 40%, about 7% to about 35%, about 7% to about 30%, about 7% to about 25%, about 7% to about 22%, about 7% to about 20%, about 7% to about 17%, about 7% to about 15%, about 7% to about 12%, about 7% to about 10%, about 10% to about 90%, about 10% to about 75%, about 10% to about 50%, about 10% to about 40%, about 10% to about 35%, about 10% to about 30%, about 10% to about 25%, about 10% to about 22%, about 10% to about 20%, about 10% to about 17%, about 10% to about 15%, about 10% to about 12%, about 12% to about 90%, about 12% to about 75%, about 12% to about 50%, about 12% to about 40%, about 12% to about 35%, about 12% to about 30%, about 12% to about 25%, about 12% to about 22%, about 12% to about 20%, about 12% to about 17%, about 12% to about 15%, about 15% to about 90%, about 15% to about 75%, about 15% to about 50%, about 15% to about 40%, about 15% to about 35%, about 15% to about 30%, about 15% to about 25%, about 15% to about 22%, about 15% to about 20%, about 15% to about 17%, about 17% to about 90%, about 17% to about 75%, about 17% to about 50%, about 17% to about 40%, about 17% to about 35%, about 17% to about 30%, about 17% to about 25%, about 17% to about 22%, about 17% to about 20%, about 20% to about 90%, about 20% to about 75%, about 20% to about 50%, about 20% to about 40%, about 20% to about 35%, about 20% to about 30%, about 20% to about 25%, about 20% to about 22%, about 22% to about 90%, about 22% to about 75%, about 22% to about 50%, about 22% to about 40%, about 22% to about 35%, about 22% to about 30%, about 22% to about 25%, about 25% to about 90%, about 25% to about 75%, about 25% to about 50%, about 25% to about 40%, about 25% to about 35%, about 25% to about 30%, about 30% to about 90%, about 30% to about 75%, about 30% to about 50%, about 30% to about 40%, about 30% to about 35%, about 35% to about 90%, about 35% to about 75%, about 35% to about 50%, about 35% to about 40%, about 40% to about 90%, about 40% to about 75%, about 40% to about 50%, about 50% to about 90%, about 50% to about 75%, or about 75% to about 90% (w/w) maralixibat or a pharmaceutically acceptable salt thereof.

In some embodiments, the composition comprises about 1%, about 2%, about 5%, about 7%, about 10%, about 12%, about 15%, about 17%, about 20%, about 22%, about 25%, about 30%, about 35%, about 40%, about 50%, about 75%, or about 90% (w/w) maralixibat or a pharmaceutically acceptable salt thereof.

In some embodiments, the composition comprises about 5% to about 40% (w/w) maralixibat or a pharmaceutically acceptable salt thereof based on the free base weight of maralixibat.

In some embodiments, the composition comprises about 10% to about 25% (w/w) maralixibat or a pharmaceutically acceptable salt thereof based on the free base weight of maralixibat.

In some embodiments, the composition comprises about 5% or about 15% (w/w) maralixibat or a pharmaceutically acceptable salt thereof based on the free base weight of maralixibat.

In one embodiment, the composition comprises maralixibat chloride.

In preparing a formulation, the active compound can be milled to provide the appropriate particle size prior to combining with the other ingredients.

In some embodiments, the maralixibat, or a pharmaceutically acceptable salt thereof is loop milled.

In some embodiments, the maralixibat, or a pharmaceutically acceptable salt thereof is pin milled.

In some embodiments, the particle size of the maralixibat, or a pharmaceutically acceptable salt thereof is about 20 μm to about 2500 μm. In some embodiments, the particle size of the maralixibat, or a pharmaceutically acceptable salt thereof is about 20 μm to about 2500 μm, about 20 μm to about 2000 μm, about 20 μm to about 1500 μm, about 20 μm to about 1000 μm, about 20 μm to about 850 μm, about 20 μm to about 800 μm, about 20 μm to about 750 μm, about 20 μm to about 700 μm, about 20 μm to about 650 μm, about 20 μm to about 600 μm, about 20 μm to about 550 μm, about 20 μm to about 500 μm, about 20 μm to about 450 μm, about 20 μm to about 400 μm, about 20 μm to about 350 μm, about 20 μm to about 300 μm, about 20 μm to about 250 μm, about 20 μm to about 200 μm, about 20 μm to about 150 μm, about 20 μm to about 125 μm, about 20 μm to about 100 μm, about 20 μm to about 80 μm, about 20 μm to about 60 μm, about 20 μm to about 40 μm, about 40 μm to about 2500 μm, about 40 μm to about 2000 μm, about 40 μm to about 1500 μm, about 40 μm to about 1000 μm, about 40 μm to about 850 μm, about 40 μm to about 800 μm, about 40 μm to about 750 μm, about 40 μm to about 700 μm, about 40 μm to about 650 μm, about 40 μm to about 600 μm, about 40 μm to about 550 μm, about 40 μm to about 500 μm, about 40 μm to about 450 μm, about 40 μm to about 400 μm, about 40 μm to about 350 μm, about 40 μm to about 300 μm, about 40 μm to about 250 μm, about 40 μm to about 200 μm, about 40 μm to about 150 μm, about 40 μm to about 125 μm, about 40 μm to about 100 μm, about 40 μm to about 80 μm, about 40 μm to about 60 μm, about 60 μm to about 2500 μm, about 60 μm to about 2000 μm, about 60 μm to about 1500 μm, about 60 μm to about 1000 μm, about 60 μm to about 850 μm, about 60 μm to about 800 μm, about 60 μm to about 750 μm, about 60 μm to about 700 μm, about 60 μm to about 650 μm, about 60 μm to about 600 μm, about 60 μm to about 550 μm, about 60 μm to about 500 μm, about 60 μm to about 450 μm, about 60 μm to about 400 μm, about 60 μm to about 350 μm, about 60 μm to about 300 μm, about 60 μm to about 250 μm, about 60 μm to about 200 μm, about 60 μm to about 150 μm, about 60 μm to about 125 μm, about 60 μm to about 100 μm, about 60 μm to about 80 μm, about 80 μm to about 2500 μm, about 80 μm to about 2000 µm, about 80 µm to about 1500 µm, about 80 µm to about 1000 µm, about 80 µm to about 850 µm, about 80 µm to about 800 µm, about 80 µm to about 750 µm, about 80 µm to about 700 µm, about 80 µm to about 650 µm, about 80 µm to about 600 µm, about 80 µm to about 550 µm, about 80 µm to about 500 µm, about 80 µm to about 450 µm, about 80 µm to about 400 µm, about 80 µm to about 350 µm, about 80 µm to about 300 µm, about 80 µm to about 250 µm, about 80 µm to about 200 µm, about 80 µm to about 150 µm, about 80 µm to about 125 µm, about 80 µm to about 100 µm, about 100 µm to about 2500 µm, about 100 µm to about 2000 µm, about 100 µm to about 1500 µm, about 100 µm to about 1000 µm, about 100 µm to about 850 µm, about 100 µm to about 800 µm, about 100 µm to about 750 µm, about 100 µm to about 700 µm, about 100 µm to about 650 µm, about 100 µm to about 600 µm, about 100 µm to about 550 µm, about 100 µm to about 500 µm, about 100 µm to about 450 µm, about 100 µm to about 400 µm, about 100 µm to about 350 µm, about 100 µm to about 300 µm, about 100 µm to about 250 µm, about 100 µm to about 200 µm, about 100 µm to about 150 µm, about 100 µm to about 125 µm, about 125 µm to about 2500 µm, about 125 µm to about 2000 µm, about 125 µm to about 1500 µm, about 125 µm to about 1000 µm, about 125 µm to about 850 µm, about 125 µm to about 800 µm, about 125 µm to about 750 µm, about 125 µm to about 700 µm, about 125 µm to about 650 µm, about 125 µm to about 600 µm, about 125 µm to about 550 µm, about 125 µm to about 500 µm, about 125 µm to about 450 µm, about 125 µm to about 400 µm, about 125 µm to about 350 µm, about 125 µm to about 300 µm, about 125 µm to about 250 µm, about 125 µm to about 200 µm, about 125 µm to about 150 µm, about 150 µm to about 2500 µm, about 150 µm to about 2000 µm, about 150 µm to about 1500 µm, about 150 µm to about 1000 µm, about 150 µm to about 850 µm, about 150 µm to about 800 µm, about 150 µm to about 750 µm, about 150 µm to about 700 µm, about 150 µm to about 650 µm, about 150 µm to about 600 µm, about 150 µm to about 550 µm, about 150 µm to about 500 µm, about 150 µm to about 450 µm, about 150 µm to about 400 µm, about 150 µm to about 350 µm, about 150 µm to about 300 µm, about 150 µm to about 250 µm, about 150 µm to about 200 µm, about 200 µm to about 2500 µm, about 200 µm to about 2000 µm, about 200 µm to about 1500 µm, about 200 µm to about 1000 µm, about 200 µm to about 850 µm, about 200 µm to about 800 µm, about 200 µm to about 750 µm, about 200 µm to about 700 µm, about 200 µm to about 650 µm, about 200 µm to about 600 µm, about 200 µm to about 550 µm, about 200 µm to about 500 µm, about 200 µm to about 450 µm, about 200 µm to about 400 µm, about 200 µm to about 350 µm, about 200 µm to about 300 µm, about 200 µm to about 250 µm, about 250 µm to about 2500 µm, about 250 µm to about 2000 µm, about 250 µm to about 1500 µm, about 250 µm to about 1000 µm, about 250 µm to about 850 µm, about 250 µm to about 800 µm, about 250 µm to about 750 µm, about 250 µm to about 700 µm, about 250 µm to about 650 µm, about 250 µm to about 600 µm, about 250 µm to about 550 µm, about 250 µm to about 500 µm, about 250 µm to about 450 µm, about 250 µm to about 400 µm, about 250 µm to about 350 µm, about 250 µm to about 300 µm, about 300 µm to about 2500 µm, about 300 µm to about 2000 µm, about 300 µm to about 1500 µm, about 300 µm to about 1000 µm, about 300 µm to about 850 µm, about 300 µm to about 800 µm, about 300 µm to about 750 µm, about 300 µm to about 700 µm, about 300 µm to about 650 µm, about 300 µm to about 600 µm, about 300 µm to about 550 µm, about 300 µm to about 500 µm, about 300 µm to about 450 µm, about 300 µm to about 400 µm, about 300 µm to about 350 µm, about 350 µm to about 2500 µm, about 350 µm to about 2000 µm, about 350 µm to about 1500 µm, about 350 µm to about 1000 µm, about 350 µm to about 850 µm, about 350 µm to about 800 µm, about 350 µm to about 750 µm, about 350 µm to about 700 µm, about 350 µm to about 650 µm, about 350 µm to about 600 µm, about 350 µm to about 550 µm, about 350 µm to about 500 µm, about 350 µm to about 450 µm, about 350 µm to about 400 µm, about 400 µm to about 2500 µm, about 400 µm to about 2000 µm, about 400 µm to about 1500 µm, about 400 µm to about 1000 µm, about 400 µm to about 850 µm, about 400 µm to about 800 µm, about 400 µm to about 750 µm, about 400 µm to about 700 µm, about 400 µm to about 650 µm, about 400 µm to about 600 µm, about 400 µm to about 550 µm, about 400 µm to about 500 µm, about 400 µm to about 450 µm, about 450 µm to about 2500 µm, about 450 µm to about 2000 µm, about 450 µm to about 1500 µm, about 450 µm to about 1000 µm, about 450 µm to about 850 µm, about 450 µm to about 800 µm, about 450 µm to about 750 µm, about 450 µm to about 700 µm, about 450 µm to about 650 µm, about 450 µm to about 600 µm, about 450 µm to about 550 µm, about 450 µm to about 500 µm, about 500 µm to about 2500 µm, about 500 µm to about 2000 µm, about 500 µm to about 1500 µm, about 500 µm to about 1000 µm, about 500 µm to about 850 µm, about 500 µm to about 800 µm, about 500 µm to about 750 µm, about 500 µm to about 700 µm, about 500 µm to about 650 µm, about 500 µm to about 600 µm, about 500 µm to about 550 µm, about 550 µm to about 2500 µm, about 550 µm to about 2000 µm, about 550 µm to about 1500 µm, about 550 µm to about 1000 µm, about 550 µm to about 850 µm, about 550 µm to about 800 µm, about 550 µm to about 750 µm, about 550 µm to about 700 µm, about 550 µm to about 650 µm, about 550 µm to about 600 µm, about 600 µm to about 2500 µm, about 600 µm to about 2000 µm, about 600 µm to about 1500 µm, about 600 µm to about 1000 µm, about 600 µm to about 850 µm, about 600 µm to about 800 µm, about 600 µm to about 750 µm, about 600 µm to about 700 µm, about 600 µm to about 650 µm, about 650 µm to about 2500 µm, about 650 µm to about 2000 µm, about 650 µm to about 1500 µm, about 650 µm to about 1000 µm, about 650 µm to about 850 µm, about 650 µm to about 800 µm, about 650 µm to about 750 µm, about 650 µm to about 700 µm, about 700 µm to about 2500 µm, about 700 µm to about 2000 µm, about 700 µm to about 1500 µm, about 700 µm to about 1000 µm, about 700 µm to about 850 µm, about 700 µm to about 800 µm, about 700 µm to about 750 µm, about 750 µm to about 2500 µm, about 750 µm to about 2000 µm, about 750 µm to about 1500 µm, about 750 µm to about 1000 µm, about 750 µm to about 850 µm, about 750 µm to about 800 µm, about 800 µm to about 2500 µm, about 800 µm to about 2000 µm, about 800 µm to about 1500 µm, about 800 µm to about 1000 µm, about 800 µm to about 850 µm, about 850 µm to about 2500 µm, about 850 µm to about 2000 µm, about 850 µm to about 1500 µm, about 850 µm to about 1000 µm, about 1000 µm to about 2500 µm, about 1000 µm to about 2000 µm, about 1000 µm to about 1500 µm, about 1500 µm to about 2500 µm, about 1500 µm to about 2000 µm, or about 2000 µm to about 2500 µm.

In some embodiments, the particle size of the maralixibat, or a pharmaceutically acceptable salt thereof is about 20 µm, about 40 µm, about 60 µm, about 80 µm, about 100 µm, about 125 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 1000 µm, about 1500 µm, about 2000 µm, or about 2500 µm.

In an additional embodiment, the particle size distribution of the maralixibat, or a pharmaceutically acceptable salt thereof has a Dv90 of less than about 850 μm.

In an additional embodiment, the particle size distribution of the maralixibat, or a pharmaceutically acceptable salt thereof has a Dv90 of less than about 100 μm.

In an additional embodiment, the particle size distribution of the maralixibat, or a pharmaceutically acceptable salt thereof has a Dv90 of less than about 60 μm.

In some embodiments, the pharmaceutical composition comprises maralixibat, or a pharmaceutically acceptable salt thereof, and:
 (i) a diluent;
 (ii) a glidant;
 (iii) a lubricant in an amount of about 0.2% to about 12% (w/w); and
 (iv) a disintegrant in an amount of about 1% to about 10% (w/w).

In some embodiments, the pharmaceutical composition comprises maralixibat, or a pharmaceutically acceptable salt thereof, and:
 (i) a diluent;
 (ii) a glidant;
 (iii) a lubricant in an amount of about 6% to about 12% (w/w); and
 (iv) a disintegrant in an amount of about 3% to about 7% (w/w).

In some embodiments, the pharmaceutical composition comprises maralixibat, or a pharmaceutically acceptable salt thereof, and:
 (i) a diluent;
 (ii) a glidant in an amount of about 0.1 to about 2% (w/w);
 (iii) a lubricant in an amount of about 6% to about 12% (w/w); and
 (iv) a disintegrant in an amount of about 3% to about 7% (w/w).

In some embodiments, the composition comprises about 0.05% to about 35% (w/w) lubricant. In some embodiments, the composition comprises about 0.05% to about 35%, about 0.05% to about 30%, about 0.05% to about 25%, about 0.05% to about 20%, about 0.05% to about 15%, about 0.05% to about 12%, about 0.05% to about 10%, about 0.05% to about 9%, about 0.05% to about 7%, about 0.05% to about 6%, about 0.05% to about 5%, about 0.05% to about 3%, about 0.05% to about 1%, about 0.05% to about 0.75%, about 0.05% to about 0.5%, about 0.05% to about 0.2%, about 0.05% to about 0.1%, about 0.1% to about 35%, about 0.1% to about 30%, about 0.1% to about 25%, about 0.1% to about 20%, about 0.1% to about 15%, about 0.1% to about 12%, about 0.10% to about 10%, about 0.10% to about 9%, about 0.10% to about 7%, about 0.1% to about 6%, about 0.1% to about 5%, about 0.1% to about 3%, about 0.1% to about 1%, about 0.1% to about 0.75%, about 0.1% to about 0.5%, about 0.1% to about 0.2%, about 0.2% to about 35%, about 0.2% to about 30%, about 0.2% to about 25%, about 0.2% to about 20%, about 0.2% to about 15%, about 0.2% to about 12%, about 0.2% to about 10%, about 0.2% to about 9%, about 0.2% to about 7%, about 0.2% to about 6%, about 0.2% to about 5%, about 0.2% to about 3%, about 0.2% to about 1%, about 0.2% to about 0.75%, about 0.2% to about 0.5%, about 0.5% to about 35%, about 0.5% to about 30%, about 0.5% to about 25%, about 0.5% to about 20%, about 0.5% to about 15%, about 0.5% to about 12%, about 0.5% to about 10%, about 0.5% to about 9%, about 0.5% to about 7%, about 0.5% to about 6%, about 0.5% to about 5%, about 0.5% to about 3%, about 0.5% to about 1%, about 0.5% to about 0.75%, about 0.75% to about 35%, about 0.75% to about 30%, about 0.75% to about 25%, about 0.75% to about 20%, about 0.75% to about 15%, about 0.75% to about 12%, about 0.75% to about 10%, about 0.75% to about 9%, about 0.75% to about 7%, about 0.75% to about 6%, about 0.75% to about 5%, about 0.75% to about 3%, about 0.75% to about 1%, about 1% to about 35%, about 1% to about 30%, about 1% to about 25%, about 1% to about 20%, about 1% to about 15%, about 1% to about 12%, about 1% to about 10%, about 1% to about 9%, about 1% to about 7%, about 1% to about 6%, about 1% to about 5%, about 1% to about 3%, about 3% to about 35%, about 3% to about 30%, about 3% to about 25%, about 3% to about 20%, about 3% to about 15%, about 3% to about 12%, about 3% to about 10%, about 3% to about 9%, about 3% to about 7%, about 3% to about 6%, about 3% to about 5%, about 5% to about 35%, about 5% to about 30%, about 5% to about 25%, about 5% to about 20%, about 5% to about 15%, about 5% to about 12%, about 5% to about 10%, about 5% to about 9%, about 5% to about 7%, about 5% to about 6%, about 6% to about 35%, about 6% to about 30%, about 6% to about 25%, about 6% to about 20%, about 6% to about 15%, about 6% to about 12%, about 6% to about 10%, about 6% to about 9%, about 6% to about 7%, about 7% to about 35%, about 7% to about 30%, about 7% to about 25%, about 7% to about 20%, about 7% to about 15%, about 7% to about 12%, about 7% to about 10%, about 7% to about 9%, about 9% to about 35%, about 9% to about 30%, about 9% to about 25%, about 9% to about 20%, about 9% to about 15%, about 9% to about 12%, about 9% to about 10%, about 10% to about 35%, about 10% to about 30%, about 10% to about 25%, about 10% to about 20%, about 10% to about 15%, about 10% to about 12%, about 12% to about 35%, about 12% to about 30%, about 12% to about 25%, about 12% to about 20%, about 12% to about 15%, about 15% to about 35%, about 15% to about 30%, about 15% to about 25%, about 15% to about 20%, about 20% to about 35%, about 20% to about 30%, about 20% to about 25%, about 25% to about 35%, about 25% to about 30%, or about 30% to about 35% (w/w) lubricant.

In some embodiments, the composition comprises about 0.05%, about 0.1%, about 0.2%, about 0.5%, about 0.75%, about 1%, about 3%, about 5%, about 6%, about 7%, about 9%, about 10%, about 12%, about 15%, about 20%, about 25%, about 30%, or about 35% (w/w) lubricant.

In some embodiments, the composition comprises about 0.2% to about 12% (w/w) lubricant.

In some embodiments, the composition comprises about 0.2% to about 6%, or about 6% to about 12% (w/w) lubricant.

In some embodiments, the composition comprises about 0.5%, 0.75%, 1%, 3%, or 9% (w/w) lubricant.

In some embodiments, the composition comprises about 9% (w/w) lubricant.

In another embodiment, the lubricant is selected from the group consisting of magnesium stearate, talc, calcium stearate, zinc stearate, sodium stearate, sodium stearyl fumarate, sodium lauryl sulfate, stearic acid, aluminum stearate, leucine, glyceryl behenate, glyceryl dibehenate, glyceryl palmitostearate, hydrogenated vegetable oil, and any combinations thereof.

The hydrogenated cottonseed oil (a plant-derived lubricant) is sold under the trademark of Lubritab®.

In another embodiment, the lubricant is glyceryl palmitostearate.

Glyceryl palmitostearate is sold under the trademark of "Precirol® ATO 5" or "Precirol®".

In some embodiments, the composition comprises about 0.25% to about 30% (w/w) disintegrant. In some embodiments, the composition comprises about 0.25% to about 30%, about 0.25% to about 20%, about 0.25% to about 15%, about 0.25% to about 10%, about 0.25% to about 9%, about 0.25% to about 8%, about 0.25% to about 7%, about 0.25% to about 6%, about 0.25% to about 5%, about 0.25% to about 4%, about 0.25% to about 3%, about 0.25% to about 2%, about 0.25% to about 1%, about 0.25% to about 0.75%, about 0.25% to about 0.5%, about 0.5% to about 30%, about 0.5% to about 20%, about 0.5% to about 15%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 0.5% to about 0.75%, about 0.75% to about 30%, about 0.75% to about 20%, about 0.75% to about 15%, about 0.75% to about 10%, about 0.75% to about 9%, about 0.75% to about 8%, about 0.75% to about 7%, about 0.75% to about 6%, about 0.75% to about 5%, about 0.75% to about 4%, about 0.75% to about 3%, about 0.75% to about 2%, about 0.75% to about 1%, about 1% to about 30%, about 1% to about 20%, about 1% to about 15%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 30%, about 2% to about 20%, about 2% to about 15%, about 2% to about 10%, about 2% to about 9%, about 2% to about 8%, about 2% to about 7%, about 2% to about 6%, about 2% to about 5%, about 2% to about 4%, about 2% to about 3%, about 3% to about 30%, about 3% to about 20%, about 3% to about 15%, about 3% to about 10%, about 3% to about 9%, about 3% to about 8%, about 3% to about 7%, about 3% to about 6%, about 3% to about 5%, about 3% to about 4%, about 4% to about 30%, about 4% to about 20%, about 4% to about 15%, about 4% to about 10%, about 4% to about 9%, about 4% to about 8%, about 4% to about 7%, about 4% to about 6%, about 4% to about 5%, about 5% to about 30%, about 5% to about 20%, about 5% to about 15%, about 5% to about 10%, about 5% to about 9%, about 5% to about 8%, about 5% to about 7%, about 5% to about 6%, about 6% to about 30%, about 6% to about 20%, about 6% to about 15%, about 6% to about 10%, about 6% to about 9%, about 6% to about 8%, about 6% to about 7%, about 7% to about 30%, about 7% to about 20%, about 7% to about 15%, about 7% to about 10%, about 7% to about 9%, about 7% to about 8%, about 8% to about 30%, about 8% to about 20%, about 8% to about 15%, about 8% to about 10%, about 8% to about 9%, about 9% to about 30%, about 9% to about 20%, about 9% to about 15%, about 9% to about 10%, about 10% to about 30%, about 10% to about 20%, about 10% to about 15%, about 15% to about 30%, about 15% to about 20%, or about 20% to about 30% (w/w) disintegrant.

In some embodiments, the composition comprises about 0.25%, about 0.5%, about 0.75%, about 1%, about 2%, about 3%, about 4%, about 5%, about 6%, about 7%, about 8%, about 9%, about 10%, about 15%, about 20%, or about 30% (w/w) disintegrant.

In some embodiments, the composition comprises about 1% to about 10% (w/w) disintegrant.

In some embodiments, the composition comprises about 3% to about 7% (w/w) disintegrant.

In some embodiments, the composition comprises about 5% (w/w) disintegrant.

In another embodiment, the disintegrant is selected from the group consisting of croscarmellose sodium, crospovidone, starch, sodium starch glycolate, and any combinations thereof.

In another embodiment, the disintegrant is crospovidone.

In some embodiments, the composition comprises about 0.025% to about 6% (w/w) glidant. In some embodiments, the composition comprises about 0.025% to about 6%, about 0.025% to about 5%, about 0.025% to about 3%, about 0.025% to about 2%, about 0.025% to about 1.5%, about 0.025% to about 1%, about 0.025% to about 0.75%, about 0.025% to about 0.5%, about 0.025% to about 0.4%, about 0.025% to about 0.25%, about 0.025% to about 0.1%, about 0.025% to about 0.075%, about 0.025% to about 0.05, about 0.05% to about 6%, about 0.05% to about 5%, about 0.05% to about 3%, about 0.05% to about 2%, about 0.05% to about 1.5%, about 0.05% to about 1%, about 0.05% to about 0.75%, about 0.05% to about 0.5%, about 0.05% to about 0.4%, about 0.05% to about 0.25%, about 0.05% to about 0.1%, about 0.05% to about 0.075%, about 0.075% to about 6%, about 0.075% to about 5%, about 0.075% to about 3%, about 0.075% to about 2%, about 0.075% to about 1.5%, about 0.075% to about 1%, about 0.075% to about 0.75%, about 0.075% to about 0.5%, about 0.075% to about 0.4%, about 0.075% to about 0.25%, about 0.075% to about 0.1%, about 0.1% to about 6%, about 0.1% to about 5%, about 0.1% to about 3%, about 0.1% to about 2%, about 0.1% to about 1.5%, about 0.1% to about 1%, about 0.1% to about 0.75%, about 0.1% to about 0.5%, about 0.1% to about 0.4%, about 0.1% to about 0.25%, about 0.25% to about 6%, about 0.25% to about 5%, about 0.25% to about 3%, about 0.25% to about 2%, about 0.25% to about 1.5%, about 0.25% to about 1%, about 0.25% to about 0.75%, about 0.25% to about 0.5%, about 0.25% to about 0.4%, about 0.4% to about 6%, about 0.4% to about 5%, about 0.4% to about 3%, about 0.4% to about 2%, about 0.4% to about 1.5%, about 0.4% to about 1%, about 0.4% to about 0.75%, about 0.4% to about 0.5%, about 0.5% to about 6%, about 0.5% to about 5%, about 0.5% to about 3%, about 0.5% to about 2%, about 0.5% to about 1.5%, about 0.5% to about 1%, about 0.5% to about 0.75%, about 0.75% to about 6%, about 0.75% to about 5%, about 0.75% to about 3%, about 0.75% to about 2%, about 0.75% to about 1.5%, about 0.75% to about 1%, about 1% to about 6%, about 1% to about 5%, about 1% to about 3%, about 1% to about 2%, about 1% to about 1.5%, about 1.5% to about 6%, about 1.5% to about 5%, about 1.5% to about 3%, about 1.5% to about 2%, about 2% to about 6%, about 2% to about 5%, about 2% to about 3%, about 3% to about 6%, about 3% to about 5%, or about 5% to about 6% (w/w) glidant.

In some embodiments, the composition comprises about 0.025%, about 0.05%, about 0.075%, about 0.1%, about 0.25%, about 0.4%, about 0.5%, about 0.75%, about 1%, about 1.5%, about 2%, about 3%, about 5%, or about 6% (w/w) glidant.

In some embodiments, the composition comprises about 0.1 to about 2% (w/w) glidant.

In some embodiments, the composition comprises about 0.5% (w/w) glidant.

In an additional embodiment, the glidant is selected from the group consisting of silicon dioxide, magnesium stearate, talc, corn starch, and any combinations thereof.

In an additional embodiment, the glidant is silicon dioxide.

silicon dioxide is sold under the trademark of Cab-O-Sil®.

In some embodiments, the composition comprises about 25% to about 99% (w/w) diluent. In some embodiments, the composition comprises about 25% to about 99%, about 25% to about 95%, about 25% to about 92%, about 25% to about 90%, about 25% to about 89%, about 25% to about 88%, about 25% to about 87%, about 25% to about 86%, about 25% to about 85%, about 25% to about 84%, about 25% to about 82%, about 25% to about 80%, about 25% to about 77%, about 25% to about 75%, about 25% to about 72%, about 25% to about 70%, about 25% to about 69%, about 25% to about 67%, about 25% to about 65%, about 25% to about 60%, about 25% to about 50%, about 50% to about 99%, about 50% to about 95%, about 50% to about 92%, about 50% to about 90%, about 50% to about 89%, about 50% to about 88%, about 50% to about 87%, about 50% to about 86%, about 50% to about 85%, about 50% to about 84%, about 50% to about 82%, about 50% to about 80%, about 50% to about 77%, about 50% to about 75%, about 50% to about 72%, about 50% to about 70%, about 50% to about 69%, about 50% to about 67%, about 50% to about 65%, about 50% to about 60%, about 60% to about 99%, about 60% to about 95%, about 60% to about 92%, about 60% to about 90%, about 60% to about 89%, about 60% to about 88%, about 60% to about 87%, about 60% to about 86%, about 60% to about 85%, about 60% to about 84%, about 60% to about 82%, about 60% to about 80%, about 60% to about 77%, about 60% to about 75%, about 60% to about 72%, about 60% to about 70%, about 60% to about 69%, about 60% to about 67%, about 60% to about 65%, about 65% to about 99%, about 65% to about 95%, about 65% to about 92%, about 65% to about 90%, about 65% to about 89%, about 65% to about 88%, about 65% to about 87%, about 65% to about 86%, about 65% to about 85%, about 65% to about 84%, about 65% to about 82%, about 65% to about 80%, about 65% to about 77%, about 65% to about 75%, about 65% to about 72%, about 65% to about 70%, about 65% to about 69%, about 65% to about 67%, about 67% to about 99%, about 67% to about 95%, about 67% to about 92%, about 67% to about 90%, about 67% to about 89%, about 67% to about 88%, about 67% to about 87%, about 67% to about 86%, about 67% to about 85%, about 67% to about 84%, about 67% to about 82%, about 67% to about 80%, about 67% to about 77%, about 67% to about 75%, about 67% to about 72%, about 67% to about 70%, about 67% to about 69%, about 69% to about 99%, about 69% to about 95%, about 69% to about 92%, about 69% to about 90%, about 69% to about 89%, about 69% to about 88%, about 69% to about 87%, about 69% to about 86%, about 69% to about 85%, about 69% to about 84%, about 69% to about 82%, about 69% to about 80%, about 69% to about 77%, about 69% to about 75%, about 69% to about 72%, about 69% to about 70%, about 70% to about 99%, about 70% to about 95%, about 70% to about 92%, about 70% to about 90%, about 70% to about 89%, about 70% to about 88%, about 70% to about 87%, about 70% to about 86%, about 70% to about 85%, about 70% to about 84%, about 70% to about 82%, about 70% to about 80%, about 70% to about 77%, about 70% to about 75%, about 70% to about 72%, about 72% to about 99%, about 72% to about 95%, about 72% to about 92%, about 72% to about 90%, about 72% to about 89%, about 72% to about 88%, about 72% to about 87%, about 72% to about 86%, about 72% to about 85%, about 72% to about 84%, about 72% to about 82%, about 72% to about 80%, about 72% to about 77%, about 72% to about 75%, about 75% to about 99%, about 75% to about 95%, about 75% to about 92%, about 75% to about 90%, about 75% to about 89%, about 75% to about 88%, about 75% to about 87%, about 75% to about 86%, about 75% to about 85%, about 75% to about 84%, about 75% to about 82%, about 75% to about 80%, about 75% to about 77%, about 77% to about 99%, about 77% to about 95%, about 77% to about 92%, about 77% to about 90%, about 77% to about 89%, about 77% to about 88%, about 77% to about 87%, about 77% to about 86%, about 77% to about 85%, about 77% to about 84%, about 77% to about 82%, about 77% to about 80%, about 80% to about 99%, about 80% to about 95%, about 80% to about 92%, about 80% to about 90%, about 80% to about 89%, about 80% to about 88%, about 80% to about 87%, about 80% to about 86%, about 80% to about 85%, about 80% to about 84%, about 80% to about 82%, about 82% to about 99%, about 82% to about 95%, about 82% to about 92%, about 82% to about 90%, about 82% to about 89%, about 82% to about 88%, about 82% to about 87%, about 82% to about 86%, about 82% to about 85%, about 82% to about 84%, about 84% to about 99%, about 84% to about 95%, about 84% to about 92%, about 84% to about 90%, about 84% to about 89%, about 84% to about 88%, about 84% to about 87%, about 84% to about 86%, about 84% to about 85%, about 85% to about 99%, about 85% to about 95%, about 85% to about 92%, about 85% to about 90%, about 85% to about 89%, about 85% to about 88%, about 85% to about 87%, about 85% to about 86%, about 86% to about 99%, about 86% to about 95%, about 86% to about 92%, about 86% to about 90%, about 86% to about 89%, about 86% to about 88%, about 86% to about 87%, about 87% to about 99%, about 87% to about 95%, about 87% to about 92%, about 87% to about 90%, about 87% to about 89%, about 87% to about 88%, about 88% to about 99%, about 88% to about 95%, about 88% to about 92%, about 88% to about 90%, about 88% to about 89%, about 89% to about 99%, about 89% to about 95%, about 89% to about 92%, about 89% to about 90%, about 90% to about 99%, about 90% to about 95%, about 90% to about 92%, about 92% to about 99%, about 92% to about 95%, or about 95% to about 99% (w/w) diluent.

In some embodiments, the composition comprises about 25%, about 50%, about 60%, about 65%, about 67%, about 69%, about 70%, about 72%, about 75%, about 77%, about 80%, about 82%, about 84%, about 85%, about 86%, about 87%, about 88%, about 89%, about 90%, about 92%, about 95%, or about 99% (w/w) diluent.

In some embodiments, the composition comprises about 65% to about 90% (w/w) diluent.

In some embodiments, the composition comprises about 65% to about 80%, about 70% to about 85%, or about 70% to about 80% (w/w) diluent.

In some embodiments, the composition comprises about 69%, 75%, 84%, 86%, 88%, or 89% (w/w) diluent.

In an additional embodiment, the diluent is selected from the group consisting of a sugar, dextrates, dextrin, dextrose, lactose, lactose monohydrate, mannitol, sorbitol, starch, cellulose, and modified celluloses, and any combination thereof.

In an additional embodiment, the diluent is microcrystalline cellulose (MCC), lactose monohydrate, mannitol, dicalcium phosphate, or a combination thereof.

In an additional embodiment, the diluent is microcrystalline cellulose (MCC), lactose monohydrate, or a combination thereof.

The MCC is sold under the trademark of Avicel® PH-302.

The formulations can additionally include: wetting agents; emulsifying and suspending agents; preserving agents such as methyl- and propylhydroxy-benzoates; sweetening agents; coloring agents; anti-adherent agents; stabilizing agents; release-modifying agents; solvent agents; antioxidant agents; buffering agents; disintegrating agents; and flavoring agents. The compositions of the invention can be formulated so as to provide quick, sustained or delayed release of the active ingredient after administration to the patient by employing procedures known in the art.

In an additional embodiment, the composition further comprises a binder.

In one embodiment, the binder is polyvinylpyrrolidone (povidone), dibasic calcium phosphate, sucrose, corn starch, gelatin, glucose, lactose, lactose monohydrate, sodium alginate, modified cellulose, hydroxypropyl methylcellulose E3 (HPMC E3), or a combination thereof.

In some embodiments, the composition comprising maralixibat, or a pharmaceutically acceptable salt thereof, further comprises one or more of the following excipients:
 (i) a solubilizing agent;
 (ii) a channeling agent;
 (iii) a chelating agent; and
 (iv) a film coating agent.

In some embodiments, the solubilizing agent is selected from the group consisting of sodium lauryl sulfates; poloxamers; alcohols such as ethanol; sugars such as sorbitol; polyethylene glycols; propylene glycol; glycerin; N-methyl-2-pyrrolidone; dimethylacetamide; dimethylsulfoxide; cyclodextrins; phospholipids; long and medium chain fatty acid mono, di, and triglycerides; long chain fatty acid esters of polyethylene glycols (i.e., polyoxyethylated glycerides); polysorbates; propylene glycol mono- and di-esters of glycerol monocaprylocaprate, glycerol monocaprylate, glycerol mono/dicaprates, and medium chain fatty acids such as propylene glycol monocaprylate and propylene glycol monolaurate, or a combination thereof.

In one embodiment, the solubilizing agent is Poloxamer 188.

In some embodiments, the channeling agent is selected from the group consisting of sodium chloride, sugars such as lactose, lactose monohydrate, microcrystalline cellulose, polyols such as mannitol, dicalcium phosphate, polyvinylpyrrolidone (PVP), and polyethylene glycols (PEG), and a combination thereof.

In one embodiment, the channeling agent is PEG 8000.

In some embodiments, the chelating agent is selected from the group consisting of betadex sulfobutyl ether sodium; calcium acetate; citric acid monohydrate; cyclodextrins; disodium edetate; edetic acid; fumaric acid; galactose; glutamic acid; histidine; hydroxypropyl betadex; malic acid; pentetic acid; phytochelatins; poly(methyl vinyl ether-alt-maleic anhydride); potassium citrate; sodium citrate dihydrate; sodium phosphate, dibasic; sodium phosphate, monobasic; tartaric acid; and trehalose, or a combination thereof.

In one embodiment, the chelating agent is ethylenediaminetetraacetic acid (EDTA).

In some embodiments, the film coating agent is selected from the group consisting of hydrophilic polymeric materials, including but not limited to as individual component polymers or co-polymers: hydroxypropyl methyl cellulose (HPMC), hydroxypropyl methylcellulose phthalate (HPMCP), methyl cellulose, hydroxyethyl cellulose (HEC), hydroxypropyl cellulose (HPC), methyl hydroxyethyl cellulose, sodium carboxymethyl cellulose, polyvinylacetal diethylaminoacetate, polyethylene glycol, copolyvidone, polyvinylpyrrolidone, poly(methacrylic acid), aminoalkyl methacrylate copolymers, polyethylene glycol-polyvinyl alcohol (PEG-PVA) grafted copolymer, poly(acrylic acid), poly(ethyl acrylate), polysaccharides such as pullulan, and other water-soluble polymers; titanium dioxide; talc; lecithin; triethyl citrate; glycerol; glyceryl triacetate; and glycerides, or a combination thereof.

In one embodiment, the film coating agent is Polyvinyl alcohol (PVA).

In one embodiment, the film coating agent is OPADRY II.

In some embodiments, the composition comprises about 25% (w/w) maralixibat chloride and:
 (i) about 25% (w/w) MCC and about 45% (w/w) lactose monohydrate;
 (ii) about 0.5% (w/w) silicon dioxide;
 (iii) about 0.5% (w/w) magnesium stearate; and
 (iv) about 5% (w/w) croscarmellose sodium.

In some embodiments, the composition comprises about 25% (w/w) maralixibat chloride and:
 (i) about 25% (w/w) MCC and about 28% (w/w) lactose monohydrate;
 (ii) about 0.5% (w/w) silicon dioxide;
 (iii) about 0.5% (w/w) magnesium stearate; and
 (iv) about 5% (w/w) croscarmellose sodium.

In some embodiments, the composition comprises about 25% (w/w) maralixibat chloride and:
 (i) about 32% (w/w) MCC and about 25% (w/w) lactose monohydrate;
 (ii) about 0.5% (w/w) silicon dioxide;
 (iii) about 0.5% (w/w) magnesium stearate; and
 (iv) about 5% (w/w) croscarmellose sodium.

In some embodiments, the composition comprises about 25% (w/w) maralixibat chloride and:
 (i) about 37% (w/w) MCC and about 45% (w/w) lactose monohydrate;
 (ii) about 0.5% (w/w) silicon dioxide;
 (iii) about 0.5% (w/w) magnesium stearate; and
 (iv) about 5% (w/w) croscarmellose sodium.

In some embodiments, the composition comprises about 25% (w/w) maralixibat chloride and:
 (i) about 35% (w/w) MCC and about 32% (w/w) lactose monohydrate;
 (ii) about 0.5% (w/w) silicon dioxide;
 (iii) about 0.5% (w/w) magnesium stearate; and
 (iv) about 5% (w/w) croscarmellose sodium.

In some embodiments, the composition comprises about 25% (w/w) maralixibat chloride and:
 (i) about 32% (w/w) MCC and about 37% (w/w) lactose monohydrate;
 (ii) about 0.5% (w/w) silicon dioxide;
 (iii) about 0.5% (w/w) magnesium stearate; and
 (iv) about 5% (w/w) croscarmellose sodium.

In some embodiments, the composition comprises about 25% (w/w) maralixibat chloride and:
 (i) about 31.5% (w/w) MCC and about 37% (w/w) lactose monohydrate;
 (ii) about 0.5% (w/w) silicon dioxide;
 (iii) about 1% (w/w) magnesium stearate; and
 (iv) about 5% (w/w) croscarmellose sodium.

In some embodiments, the composition comprises about 25% (w/w) maralixibat chloride and:
 (i) about 25% (w/w) MCC and about 45% (w/w) lactose monohydrate;
 (ii) about 1% (w/w) silicon dioxide;
 (iii) about 0.5% (w/w) magnesium stearate; and
 (iv) about 5% (w/w) croscarmellose sodium.

In some embodiments, the composition comprises about 25% (w/w) maralixibat chloride and:
 (i) about 25% (w/w) MCC and about 28% (w/w) lactose monohydrate;
 (ii) about 1% (w/w) silicon dioxide;
 (iii) about 0.5% (w/w) magnesium stearate; and
 (iv) about 5% (w/w) croscarmellose sodium.

In some embodiments, the composition comprises about 25% (w/w) maralixibat chloride and:
(i) about 32% (w/w) MCC and about 25% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 25% (w/w) maralixibat chloride and:
(i) about 37% (w/w) MCC and about 45% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 25% (w/w) maralixibat chloride and:
(i) about 35% (w/w) MCC and about 32% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 25% (w/w) maralixibat chloride and:
(i) about 32% (w/w) MCC and about 37% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 25% (w/w) maralixibat chloride and:
(i) about 31.5% (w/w) MCC and about 37% (w/w) lactose monohydrate;
(ii) about 1% (w/w) silicon dioxide;
(iii) about 1% (w/w) magnesium stearate; and
(iv) about 5% (w/w) croscarmellose sodium.

In some embodiments, the composition comprises about 25% (w/w) maralixibat chloride and:
(i) about 25% (w/w) MCC and about 45% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 25% (w/w) maralixibat chloride and:
(i) about 25% (w/w) MCC and about 28% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 25% (w/w) maralixibat chloride and:
(i) about 32% (w/w) MCC and about 25% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 25% (w/w) maralixibat chloride and:
(i) about 37% (w/w) MCC and about 45% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 25% (w/w) maralixibat chloride and:
(i) about 35% (w/w) MCC and about 32% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 25% (w/w) maralixibat chloride and:
(i) about 32% (w/w) MCC and about 37% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 25% (w/w) maralixibat chloride and:
(i) about 31.5% (w/w) MCC and about 37% (w/w) lactose monohydrate;
(ii) about 0.5% (w/w) silicon dioxide;
(iii) about 0.5% (w/w) magnesium stearate; and
(iv) about 5% (w/w) croscarmellose sodium.

In some embodiments, the composition comprises about 25% (w/w) maralixibat chloride and:
(i) about 25% (w/w) MCC and about 45% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 25% (w/w) maralixibat chloride and:
(i) about 25% (w/w) MCC and about 28% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 25% (w/w) maralixibat chloride and:
(i) about 32% (w/w) MCC and about 25% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 25% (w/w) maralixibat chloride and:
(i) about 37% (w/w) MCC and about 45% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 25% (w/w) maralixibat chloride and:
(i) about 35% (w/w) MCC and about 32% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 25% (w/w) maralixibat chloride and:
(i) about 32% (w/w) MCC and about 37% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 25% (w/w) maralixibat chloride and:
(i) about 31.5% (w/w) MCC and about 37% (w/w) lactose monohydrate;
(ii) about 0.5% (w/w) silicon dioxide;
(iii) about 1% (w/w) magnesium stearate; and
(iv) about 3% (w/w) croscarmellose sodium.

In some embodiments, the composition comprises about 10.5% (w/w) maralixibat chloride and:
(i) about 24% (w/w) MCC and about 59.5% (w/w) lactose monohydrate;
(ii) about 0.5% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 24% (w/w) MCC and about 59% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 60% (w/w) MCC and about 23.5% (w/w) lactose monohydrate;
(ii) about 0.5% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and
(i) about 60% (w/w) MCC and about 23.5% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 32% (w/w) MCC and about 37% (w/w) lactose monohydrate;
(ii) about 0.5% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 25% (w/w) MCC and about 45% (w/w) lactose monohydrate;
(ii) about 0.5% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 37% (w/w) MCC and about 45% (w/w) lactose monohydrate;
(ii) about 0.5% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 35% (w/w) MCC and about 32% (w/w) lactose monohydrate;
(ii) about 0.5% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 40% (w/w) MCC and about 40% (w/w) lactose monohydrate;
(ii) about 0.5% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 24% (w/w) MCC and about 59.5% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 60% (w/w) MCC and about 23.5% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 32% (w/w) MCC and about 37% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 60% (w/w) MCC and about 23.5% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 60% (w/w) MCC and about 23.5% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 32% (w/w) MCC and about 37% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 25% (w/w) MCC and about 45% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 37% (w/w) MCC and about 45% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 35% (w/w) MCC and about 32% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 40% (w/w) MCC and about 40% (w/w) lactose monohydrate;
(ii) about 1% (w/w) silicon dioxide;
(iii) about 0.5% (w/w) magnesium stearate; and
(iv) about 5% (w/w) croscarmellose sodium.

In some embodiments, the composition comprises about 10.5% (w/w) maralixibat chloride and:
(i) about 24% (w/w) MCC and about 59.5% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 60% (w/w) MCC and about 23.5% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 32% (w/w) MCC and about 37% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 25% (w/w) MCC and about 45% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 37% (w/w) MCC and about 45% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 35% (w/w) MCC and about 32% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 40% (w/w) MCC and about 40% (w/w) lactose monohydrate;
(ii) about 0.5% (w/w) silicon dioxide;
(iii) about 1% (w/w) magnesium stearate; and
(iv) about 5% (w/w) croscarmellose sodium.

In some embodiments, the composition comprises about 10.5% (w/w) maralixibat chloride and:
(i) about 24% (w/w) MCC and about 59.5% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 10.5% (w/w) maralixibat chloride and:
(i) about 60% (w/w) MCC and about 23.5% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 10.5% (w/w) maralixibat chloride and:
(i) about 32% (w/w) MCC and about 37% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 10.5% (w/w) maralixibat chloride and:
(i) about 25% (w/w) MCC and about 45% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 10.5% (w/w) maralixibat chloride and:
(i) about 37% (w/w) MCC and about 45% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 10.5% (w/w) maralixibat chloride and:
(i) about 35% (w/w) MCC and about 32% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 10.5% (w/w) maralixibat chloride and:
(i) about 40% (w/w) MCC and about 40% (w/w) lactose monohydrate;
(ii) about 0.5% (w/w) silicon dioxide;
(iii) about 0.5% (w/w) magnesium stearate; and
(iv) about 3% (w/w) croscarmellose sodium.

In some embodiments, the composition comprises about 10.5% (w/w) maralixibat chloride and:
(i) about 65% (w/w) MCC and about 23.5% (w/w) lactose monohydrate;
(ii) about 0.5% (w/w) silicon dioxide; and
(iii) about 0.75% (w/w) magnesium stearate.

In some embodiments, the composition comprises about 10.5% (w/w) maralixibat chloride and:
(i) about 35% (w/w) MCC and about 40% (w/w) lactose monohydrate;
(ii) about 0.5% (w/w) silicon dioxide; and
(iii) about 0.75% (w/w) magnesium stearate.

In some embodiments, the composition comprises about 10.5% (w/w) maralixibat chloride and:
(i) about 30% (w/w) MCC and about 50% (w/w) lactose monohydrate;
(ii) about 0.5% (w/w) silicon dioxide; and
(iii) about 0.75% (w/w) magnesium stearate.

In some embodiments, the composition comprises about 10.5% (w/w) maralixibat chloride and:
(i) about 23.5% (w/w) MCC and about 65% (w/w) lactose monohydrate;
(ii) about 1% (w/w) silicon dioxide; and
(iii) about 0.75% (w/w) magnesium stearate.

In some embodiments, the composition comprises about 10.5% (w/w) maralixibat chloride and:
(i) about 23.5% (w/w) MCC and about 65% (w/w) lactose monohydrate;
(ii) about 0.5% (w/w) silicon dioxide; and
(iii) about 2% (w/w) magnesium stearate.

In some embodiments, the composition comprises about 10.5% (w/w) maralixibat chloride and:
(i) about 65% (w/w) MCC and about 23.5% (w/w) lactose monohydrate;
(ii) about 0.5% (w/w) silicon dioxide;
(iii) about 0.75% (w/w) magnesium stearate; and
(iv) about 0.1% (w/w) EDTA.

In some embodiments, the composition comprises about 10.5% (w/w) maralixibat chloride and:
(i) about 35% (w/w) MCC and about 40% (w/w) lactose monohydrate;
(ii) about 0.5% (w/w) silicon dioxide;
(iii) about 0.75% (w/w) magnesium stearate; and
(iv) about 0.1% (w/w) EDTA.

In some embodiments, the composition comprises about 10.5% (w/w) maralixibat chloride and:
(i) about 30% (w/w) MCC and about 50% (w/w) lactose monohydrate;
(ii) about 0.5% (w/w) silicon dioxide;
(iii) about 0.75% (w/w) magnesium stearate; and
(iv) about 0.1% (w/w) EDTA.

In some embodiments, the composition comprises about 10.5% (w/w) maralixibat chloride and:
(i) about 23.5% (w/w) MCC and about 65% (w/w) lactose monohydrate;
(ii) about 1% (w/w) silicon dioxide;
(iii) about 0.75% (w/w) magnesium stearate; and
(iv) about 0.1% (w/w) EDTA.

In some embodiments, the composition comprises about 10.5% (w/w) maralixibat chloride and:
(i) about 23.5% (w/w) MCC and about 65% (w/w) lactose monohydrate;
(ii) about 0.5% (w/w) silicon dioxide;
(iii) about 2% (w/w) magnesium stearate; and
(iv) about 0.1% (w/w) EDTA.

In some embodiments, the composition comprises about 10.5% (w/w) maralixibat chloride and:
(i) about 65% (w/w) MCC and about 23.5% (w/w) lactose monohydrate;
(ii) about 0.5% (w/w) silicon dioxide; and
(iii) about 0.75% (w/w) sodium stearyl fumarate.

In some embodiments, the composition comprises about 10.5% (w/w) maralixibat chloride and:
(i) about 35% (w/w) MCC and about 40% (w/w) lactose monohydrate;
(ii) about 0.5% (w/w) silicon dioxide; and
(iii) about 0.75% (w/w) sodium stearyl fumarate.

In some embodiments, the composition comprises about 10.5% (w/w) maralixibat chloride and:
(i) about 30% (w/w) MCC and about 50% (w/w) lactose monohydrate;
(ii) about 0.5% (w/w) silicon dioxide; and
(iii) about 0.75% (w/w) sodium stearyl fumarate.

In some embodiments, the composition comprises about 10.5% (w/w) maralixibat chloride and:
(i) about 23.5% (w/w) MCC and about 65% (w/w) lactose monohydrate;
(ii) about 1% (w/w) silicon dioxide; and
(iii) about 0.75% (w/w) sodium stearyl fumarate.

In some embodiments, the composition comprises about 10.5% (w/w) maralixibat chloride and:
(i) about 23.5% (w/w) MCC and about 65% (w/w) lactose monohydrate;
(ii) about 0.5% (w/w) silicon dioxide; and
(iii) about 2% (w/w) sodium stearyl fumarate.

In some embodiments, the composition comprises about 10.5% (w/w) maralixibat chloride and:
(i) about 65% (w/w) MCC and about 23.5% (w/w) lactose monohydrate;
(ii) about 0.5% (w/w) silicon dioxide; and
(iii) about 0.75% (w/w) stearic acid.

In some embodiments, the composition comprises about 10.5% (w/w) maralixibat chloride and:
(i) about 64.5% (w/w) MCC and about 23.5% (w/w) lactose monohydrate;
(ii) about 0.5% (w/w) silicon dioxide; and
(iii) about 1% (w/w) stearic acid.

In some embodiments, the composition comprises about 10.5% (w/w) maralixibat chloride and:
(i) about 35% (w/w) MCC and about 40% (w/w) lactose monohydrate;
(ii) about 0.5% (w/w) silicon dioxide; and
(iii) about 0.75% (w/w) stearic acid.

In some embodiments, the composition comprises about 10.5% (w/w) maralixibat chloride and:
(i) about 30% (w/w) MCC and about 50% (w/w) lactose monohydrate;
(ii) about 0.5% (w/w) silicon dioxide; and
(iii) about 0.75% (w/w) stearic acid.

In some embodiments, the composition comprises about 10.5% (w/w) maralixibat chloride and:
(i) about 23.5% (w/w) MCC and about 65% (w/w) lactose monohydrate;
(ii) about 1% (w/w) silicon dioxide; and
(iii) about 0.75% (w/w) stearic acid.

In some embodiments, the composition comprises about 10.5% (w/w) maralixibat chloride and:
(i) about 23.5% (w/w) MCC and about 65% (w/w) lactose monohydrate;
(ii) about 0.5% (w/w) silicon dioxide; and
(iii) about 2% (w/w) stearic acid.

In some embodiments, the composition comprises about 10.5% (w/w) maralixibat chloride and:
(i) about 62.5% (w/w) MCC and about 23.5% (w/w) lactose monohydrate;
(ii) about 0.5% (w/w) silicon dioxide; and
(iii) about 3% (w/w) hydrogenated cottonseed oil.

In some embodiments, the composition comprises about 10.5% (w/w) maralixibat chloride and:
(i) about 40% (w/w) MCC and about 35% (w/w) lactose monohydrate;
(ii) about 0.5% (w/w) silicon dioxide; and
(iii) about 3% (w/w) hydrogenated cottonseed oil.

In some embodiments, the composition comprises about 10.5% (w/w) maralixibat chloride and:
(i) about 50% (w/w) MCC and about 30% (w/w) lactose monohydrate;
(ii) about 0.5% (w/w) silicon dioxide; and
(iii) about 3% (w/w) hydrogenated cottonseed oil.

In some embodiments, the composition comprises about 10.5% (w/w) maralixibat chloride and:
(i) about 62.5% (w/w) MCC and about 23.5% (w/w) lactose monohydrate;
(ii) about 1% (w/w) silicon dioxide; and
(iii) about 3% (w/w) lubritab.

In some embodiments, the composition comprises about 10.5% (w/w) maralixibat chloride and:
(i) about 62.5% (w/w) MCC and about 23.5% (w/w) lactose monohydrate;
(ii) about 0.5% (w/w) silicon dioxide; and
(iii) about 2% (w/w) hydrogenated cottonseed oil.

In some embodiments, the composition comprises about 10.5% (w/w) maralixibat chloride and:
(i) about 62.5% (w/w) MCC and about 23.5% (w/w) lactose monohydrate;
(ii) about 0.5% (w/w) silicon dioxide; and
(iii) about 3% (w/w) glyceryl dibehenate.

In some embodiments, the composition comprises about 10.5% (w/w) maralixibat chloride and:
(i) about 40% (w/w) MCC and about 35% (w/w) lactose monohydrate;
(ii) about 0.5% (w/w) silicon dioxide; and
(iii) about 3% (w/w) glyceryl dibehenate.

In some embodiments, the composition comprises about 10.5% (w/w) maralixibat chloride and:
(i) about 50% (w/w) MCC and about 30% (w/w) lactose monohydrate;
(ii) about 0.5% (w/w) silicon dioxide; and
(iii) about 3% (w/w) glyceryl dibehenate.

In some embodiments, the composition comprises about 10.5% (w/w) maralixibat chloride and:
(i) about 62.5% (w/w) MCC and about 23.5% (w/w) lactose monohydrate;
(ii) about 1% (w/w) silicon dioxide; and
(iii) about 3% (w/w) glyceryl dibehenate.

In some embodiments, the composition comprises about 10.5% (w/w) maralixibat chloride and:
(i) about 62.5% (w/w) MCC and about 23.5% (w/w) lactose monohydrate;
(ii) about 0.5% (w/w) silicon dioxide; and
(iii) about 2% (w/w) glyceryl dibehenate.

In some embodiments, the composition comprises about 10.5% (w/w) maralixibat chloride and:
  (i) 62.5% (w/w) MCC and about 23.5% (w/w) lactose monohydrate;
  (ii) about 0.5% (w/w) silicon dioxide; and
  (iii) about 3% (w/w) glyceryl palmitostearate.

In some embodiments, the composition comprises about 10.5% (w/w) maralixibat chloride and:
  (i) 40% (w/w) MCC and about 35% (w/w) lactose monohydrate;
  (ii) about 0.5% (w/w) silicon dioxide; and
  (iii) about 3% (w/w) glyceryl palmitostearate.

In some embodiments, the composition comprises about 10.5% (w/w) maralixibat chloride and:
  (i) 50% (w/w) MCC and about 30% (w/w) lactose monohydrate;
  (ii) about 0.5% (w/w) silicon dioxide; and
  (iii) about 3% (w/w) glyceryl palmitostearate.

In some embodiments, the composition comprises about 10.5% (w/w) maralixibat chloride and:
  (i) 62.5% (w/w) MCC and about 23.5% (w/w) lactose monohydrate;
  (ii) about 1% (w/w) silicon dioxide; and
  (iii) about 3% (w/w) glyceryl palmitostearate.

In some embodiments, the composition comprises about 10.5% (w/w) maralixibat chloride and:
  (i) 62.5% (w/w) MCC and about 23.5% (w/w) lactose monohydrate;
  (ii) about 0.5% (w/w) silicon dioxide; and
  (iii) about 2% (w/w) glyceryl palmitostearate.

In some embodiments, the composition comprises about 10.5% (w/w) maralixibat chloride and:
  (i) about 62.5% (w/w) MCC and about 23.5% (w/w) lactose monohydrate;
  (ii) about 0.5% (w/w) silicon dioxide; and
  (iii) about 3% (w/w) sodium lauryl sulfate.

In some embodiments, the composition comprises about 10.5% (w/w) maralixibat chloride and:
  (i) about 40% (w/w) MCC and about 35% (w/w) lactose monohydrate;
  (ii) about 0.5% (w/w) silicon dioxide; and
  (iii) about 3% (w/w) sodium lauryl sulfate.

In some embodiments, the composition comprises about 10.5% (w/w) maralixibat chloride and:
  (i) about 50% (w/w) MCC and about 30% (w/w) lactose monohydrate;
  (ii) about 0.5% (w/w) silicon dioxide; and
  (iii) about 3% (w/w) sodium lauryl sulfate.

In some embodiments, the composition comprises about 10.5% (w/w) maralixibat chloride and:
  (i) about 62.5% (w/w) MCC and about 23.5% (w/w) lactose monohydrate;
  (ii) about 1% (w/w) silicon dioxide; and
  (iii) about 3% (w/w) sodium lauryl sulfate.

In some embodiments, the composition comprises about 10.5% (w/w) maralixibat chloride and:
  (i) about 62.5% (w/w) MCC and about 23.5% (w/w) lactose monohydrate;
  (ii) about 0.5% (w/w) silicon dioxide; and
  (iii) about 2% (w/w) sodium lauryl sulfate.

Also provided herein is a composition comprising about 10.5% (w/w) maralixibat chloride and:
  (i) about 62.5% (w/w) MCC and about 23.5% (w/w) lactose monohydrate;
  (ii) about 0.5% (w/w) silicon dioxide; and
  (iii) about 3% (w/w) Poloxamer 188.

In some embodiments, the composition comprises about 10.5% (w/w) maralixibat chloride and:
  (i) about 40% (w/w) MCC and about 35% (w/w) lactose monohydrate;
  (ii) about 0.5% (w/w) silicon dioxide; and
  (iii) about 3% (w/w) Poloxamer 188.

In some embodiments, the composition comprises about 10.5% (w/w) maralixibat chloride and:
  (i) about 50% (w/w) MCC and about 30% (w/w) lactose monohydrate;
  (ii) about 0.5% (w/w) silicon dioxide; and
  (iii) about 3% (w/w) Poloxamer 188.

In some embodiments, the composition comprises about 10.5% (w/w) maralixibat chloride and:
  (i) about 62.5% (w/w) MCC and about 23.5% (w/w) lactose monohydrate;
  (ii) about 1% (w/w) silicon dioxide; and
  (iii) about 3% (w/w) Poloxamer 188.

In some embodiments, the composition comprises about 10.5% (w/w) maralixibat chloride and:
  (i) about 62.5% (w/w) MCC and about 23.5% (w/w) lactose monohydrate;
  (ii) about 0.5% (w/w) silicon dioxide; and
  (iii) about 2% (w/w) Poloxamer 188.

Also provided herein is a composition comprising about 10.5% (w/w) maralixibat chloride and:
  (i) about 62.5% (w/w) MCC and about 23.5% (w/w) lactose monohydrate;
  (ii) about 0.5% (w/w) silicon dioxide; and
  (iii) about 3% (w/w) PEG 8000.

In some embodiments, the composition comprises about 10.5% (w/w) maralixibat chloride and:
  (i) about 40% (w/w) MCC and about 35% (w/w) lactose monohydrate;
  (ii) about 0.5% (w/w) silicon dioxide; and
  (iii) about 3% (w/w) PEG 8000.

In some embodiments, the composition comprises about 10.5% (w/w) maralixibat chloride and:
  (i) about 50% (w/w) MCC and about 30% (w/w) lactose monohydrate;
  (ii) about 0.5% (w/w) silicon dioxide; and
  (iii) about 3% (w/w) PEG 8000.

In some embodiments, the composition comprises about 10.5% (w/w) maralixibat chloride and:
  (i) about 62.5% (w/w) MCC and about 23.5% (w/w) lactose monohydrate;
  (ii) about 1% (w/w) silicon dioxide; and
  (iii) about 3% (w/w) PEG 8000.

In some embodiments, the composition comprises about 10.5% (w/w) maralixibat chloride and:
  (i) about 62.5% (w/w) MCC and about 23.5% (w/w) lactose monohydrate;
  (ii) about 0.5% (w/w) silicon dioxide; and
  (iii) about 2% (w/w) PEG 8000.

In some embodiments, the composition comprises about 9.8% (w/w) maralixibat chloride and
  (i) about 60% (w/w) MCC and about 21.8% (w/w) lactose monohydrate;
  (ii) about 0.5% (w/w) silicon dioxide; and
  (iii) about 10% (w/w) hydrogenated cottonseed oil.

In some embodiments, the composition comprises about 10.5% (w/w) maralixibat chloride and
  (i) about 59% (w/w) MCC and about 22.5% (w/w) lactose monohydrate;
  (ii) about 0.5% (w/w) silicon dioxide; and
  (iii) about 7.5% (w/w) glyceryl palmitostearate.

In some embodiments, the composition comprises about 10.4% (w/w) maralixibat chloride and
(i) about 58% (w/w) MCC and about 22.1% (w/w) lactose monohydrate;
(ii) about 0.5% (w/w) silicon dioxide; and
(iii) about 9.0% (w/w) glyceryl palmitostearate.

In some embodiments, the composition comprises about 9.8% (w/w) maralixibat chloride and
(i) about 55.2% (w/w) MCC and about 21.0% (w/w) lactose monohydrate;
(ii) about 0.5% (w/w) silicon dioxide;
(iii) about 8.6% (w/w) glyceryl palmitostearate; and
(iv) about 5.0% (w/w) crospovidone.

In some embodiments, the composition comprises about 10.0% (w/w) maralixibat chloride and
(i) about 61.7% (w/w) MCC and about 22.4% (w/w) lactose monohydrate;
(ii) about 0.5% (w/w) silicon dioxide;
(iii) about 8.6% (w/w) glyceryl palmitostearate and about 0.7% (w/w) magnesium stearate; and
(iv) about 4.8% (w/w) crospovidone.

In some embodiments, the composition comprises about 10.5% (w/w) maralixibat chloride and:
(i) about 50% (w/w) MCC and about 25% (w/w) lactose monohydrate;
(ii) about 0.5% (w/w) silicon dioxide;
(iii) about 9% (w/w) glyceryl palmitostearate; and
(iv) about 5% (w/w) crospovidone.

In some embodiments, the composition comprises about 10.5% (w/w) maralixibat chloride and:
(i) about 40% (w/w) MCC and about 35% (w/w) lactose monohydrate;
(ii) about 0.5% (w/w) silicon dioxide;
(iii) about 9% (w/w) glyceryl palmitostearate; and
(iv) about 5% (w/w) crospovidone.

In some embodiments, the composition comprises about 10.5% (w/w) maralixibat chloride and:
(i) about 45% (w/w) MCC and about 30% (w/w) lactose monohydrate;
(ii) about 0.5% (w/w) silicon dioxide;
(iii) about 9% (w/w) glyceryl palmitostearate; and
(iv) about 5% (w/w) crospovidone.

In some embodiments, the composition comprises about 10.5% (w/w) maralixibat chloride and:
(i) about 50% (w/w) MCC and about 25% (w/w) lactose monohydrate;
(ii) about 1% (w/w) silicon dioxide;
(iii) about 9% (w/w) glyceryl palmitostearate; and
(iv) about 5% (w/w) crospovidone.

In some embodiments, the composition comprises about 10.5% (w/w) maralixibat chloride and:
(i) about 50% (w/w) MCC and about 25% (w/w) lactose monohydrate;
(ii) about 0.5% (w/w) silicon dioxide;
(iii) about 7% (w/w) glyceryl palmitostearate; and
(iv) about 5% (w/w) crospovidone.

In some embodiments, the composition comprises about 10.5% (w/w) maralixibat chloride and:
(i) about 50% (w/w) MCC and about 25% (w/w) lactose monohydrate;
(ii) about 0.5% (w/w) silicon dioxide;
(iii) about 9% (w/w) glyceryl palmitostearate; and
(iv) about 3% (w/w) crospovidone.

In some embodiments, the composition comprises about 5 mg to about 50 mg maralixibat or a pharmaceutically acceptable salt thereof based on the free base weight of maralixibat.

In some embodiments, the composition comprises about 5 mg, about 10 mg, about 30 mg, or about 50 mg maralixibat or a pharmaceutically acceptable salt thereof based on the free base weight of maralixibat.

In an additional embodiment, the composition is stable at room temperature and 60% relative humidity (RH) for at least 6 months.

In an additional embodiment, the composition is stable at −4° C. and 60% RH for at least 6 months.

In an additional embodiment, the composition is stable at 25° C. and 60% RH for at least 6 months.

In an additional embodiment, the composition is stable at 30° C. and 60% RH for at least 6 months.

In an additional embodiment, the composition is stable at 30° C. and 65% RH for at least 6 months.

In an additional embodiment, the composition is stable at 40° C. and 60% RH for at least 6 months.

In an additional embodiment, the composition is stable at 60° C. and 60% RH for at least 6 months.

In an additional embodiment, the composition is stable at 40° C. and 75% RH for at least 6 months.

In an additional embodiment, the composition is stable at room temperature and 75% RH for at least 6 months.

In an additional embodiment, the composition is stable at −4° C. and 75% RH for at least 6 months.

In an additional embodiment, the composition is stable at 25° C. and 75% RH for at least 6 months.

In an additional embodiment, the composition is stable at 30° C. and 75% RH for at least 6 months.

In an additional embodiment, the composition is stable at 60° C. and 75% RH for at least 6 months.

In an additional embodiment, the composition is stable at 40° C. and 85% RH for at least 6 months.

In an additional embodiment, the composition is stable at room temperature and 85% RH for at least 6 months.

In an additional embodiment, the composition is stable at −4° C. and 85% RH for at least 6 months.

In an additional embodiment, the composition is stable at 25° C. and 85% RH for at least 6 months.

In an additional embodiment, the composition is stable at 30° C. and 85% RH for at least 6 months.

In an additional embodiment, the composition is stable at 60° C. and 85% RH for at least 6 months.

In an additional embodiment, the composition is stable at 40° C. and 50% RH for at least 6 months.

In an additional embodiment, the composition is stable at room temperature and 50% RH for at least 6 months.

In an additional embodiment, the composition is stable at −4° C. and 50% RH for at least 6 months.

In an additional embodiment, the composition is stable at 25° C. and 50% RH for at least 6 months.

In an additional embodiment, the composition is stable at 21° C. and 45% RH for at least 6 months.

In an additional embodiment, the composition is stable at 30° C. and 50% RH for at least 6 months.

In an additional embodiment, the composition is stable at 30° C. and 35% RH for at least 6 months.

In an additional embodiment, the composition is stable at 60° C. and 50% RH for at least 6 months.

In one embodiment, the composition is stable for at least 12 months.

In one embodiment, the composition is stable for at least 24 months.

In one embodiment, the composition is stable for at least 36 months.

In one embodiment, the composition is stable for at least 48 months.

In one embodiment, the composition is stable for at least 60 months.

Further provided herein is an oral dosage form comprising about 5 mg to about 50 mg maralixibat, or a pharmaceutically acceptable salt thereof, based on the free base weight of maralixibat, and one or more excipients, wherein:
about 100% of maralixibat, or a pharmaceutically acceptable salt thereof, dissolves in an acidic pH environment; and
upon pH increase from the acidic pH environment to a pH of about 5.0 to about 8.5, at least about 65% of maralixibat, or a pharmaceutically acceptable salt thereof, remains dissolved for at least about 1 hour.

Further provided herein is an oral dosage form comprising about 5 mg to about 50 mg maralixibat, or a pharmaceutically acceptable salt thereof, based on the free base weight of maralixibat, and one or more excipients, wherein:
about 100% of maralixibat, or a pharmaceutically acceptable salt thereof, dissolves in an acidic pH environment of a pH less than about 5.0; and
upon pH increase from the acidic pH environment to a pH of about 6.0 to about 7.4, at least about 65% of maralixibat, or a pharmaceutically acceptable salt thereof, remains dissolved for at least about 1 hour.

In some embodiments, the acidic pH environment has a pH of less than about 6.8. In some embodiments, the acidic pH environment has a pH of less than about 9.0, 8.5, 8.0, 7.5, 7.0, 6.5, 6.0, 5.5, 5.0, 4.5, 4.0, 3.5, 3.0, 2.5, 2.0, 1.5, 1.0, 0.5.

In some embodiments, the acidic pH environment has a pH of about 0.5 to about 1.0, about 0.5 to about 1.5, about 0.5 to about 2.0, about 0.5 to about 2.5, about 0.5 to about 3.0, about 0.5 to about 3.5, about 0.5 to about 4.0, about 0.5 to about 4.5, about 0.5 to about 5.0, about 0.5 to about 5.5, about 0.5 to about 6.0, about 0.5 to about 6.5, about 0.5 to about 7.0, about 0.5 to about 7.5, about 0.5 to about 8.0, about 0.5 to about 8.5, about 0.5 to about 9.0, about 1.0 to about 1.5, about 1.0 to about 2.0, about 1.0 to about 2.5, about 1.0 to about 3.0, about 1.0 to about 3.5, about 1.0 to about 4.0, about 1.0 to about 4.5, about 1.0 to about 5.0, about 1.0 to about 5.5, about 1.0 to about 6.0, about 1.0 to about 6.5, about 1.0 to about 7.0, about 1.0 to about 7.5, about 1.0 to about 8.0, about 1.0 to about 8.5, about 1.0 to about 9.0, about 1.5 to about 2.0, about 1.5 to about 2.5, about 1.5 to about 3.0, about 1.5 to about 3.5, about 1.5 to about 4.0, about 1.5 to about 4.5, about 1.5 to about 5.0, about 1.5 to about 5.5, about 1.5 to about 6.0, about 1.5 to about 6.5, about 1.5 to about 7.0, about 1.5 to about 7.5, about 1.5 to about 8.0, about 1.5 to about 8.5, about 1.5 to about 9.0, about 2.0 to about 2.5, about 2.0 to about 3.0, about 2.0 to about 3.5, about 2.0 to about 4.0, about 2.0 to about 4.5, about 2.0 to about 5.0, about 2.0 to about 5.5, about 2.0 to about 6.0, about 2.0 to about 6.5, about 2.0 to about 7.0, about 2.0 to about 7.5, about 2.0 to about 8.0, about 2.0 to about 8.5, about 2.0 to about 9.0, about 2.5 to about 3.0, about 2.5 to about 3.5, about 2.5 to about 4.0, about 2.5 to about 4.5, about 2.5 to about 5.0, about 2.5 to about 5.5, about 2.5 to about 6.0, about 2.5 to about 6.5, about 2.5 to about 7.0, about 2.5 to about 7.5, about 2.5 to about 8.0, about 2.5 to about 8.5, about 2.5 to about 9.0, about 3.0 to about 3.5, about 3.0 to about 4.0, about 3.0 to about 4.5, about 3.0 to about 5.0, about 3.0 to about 5.5, about 3.0 to about 6.0, about 3.0 to about 6.5, about 3.0 to about 7.0, about 3.0 to about 7.5, about 3.0 to about 8.0, about 3.0 to about 8.5, about 3.0 to about 9.0, about 3.5 to about 4.0, about 3.5 to about 4.5, about 3.5 to about 5.0, about 3.5 to about 5.5, about 3.5 to about 6.0, about 3.5 to about 6.5, about 3.5 to about 7.0, about 3.5 to about 7.5, about 3.5 to about 8.0, about 3.5 to about 8.5, about 3.5 to about 9.0, about 4.0 to about 4.5, about 4.0 to about 5.0, about 4.0 to about 5.5, about 4.0 to about 6.0, about 4.0 to about 6.5, about 4.0 to about 7.0, about 4.0 to about 7.5, about 4.0 to about 8.0, about 4.0 to about 8.5, about 4.0 to about 9.0, about 4.5 to about 5.0, about 4.5 to about 5.5, about 4.5 to about 6.0, about 4.5 to about 6.5, about 4.5 to about 7.0, about 4.5 to about 7.5, about 4.5 to about 8.0, about 4.5 to about 8.5, about 4.5 to about 9.0, about 5.0 to about 5.5, about 5.0 to about 6.0, about 5.0 to about 6.5, about 5.0 to about 7.0, about 5.0 to about 7.5, about 5.0 to about 8.0, about 5.0 to about 8.5, about 5.0 to about 9.0, about 5.5 to about 6.0, about 5.5 to about 6.5, about 5.5 to about 7.0, about 5.5 to about 7.5, about 5.5 to about 8.0, about 5.5 to about 8.5, about 5.5 to about 9.0, about 6.0 to about 6.5, about 6.0 to about 7.0, about 6.0 to about 7.5, about 6.0 to about 8.0, about 6.0 to about 8.5, about 6.0 to about 9.0, about 6.5 to about 7.0, about 6.5 to about 7.5, about 6.5 to about 8.0, about 6.5 to about 8.5, about 6.5 to about 9.0, about 7.0 to about 7.5, about 7.0 to about 8.0, about 7.0 to about 8.5, about 7.0 to about 9.0, about 7.5 to about 8.0, about 7.5 to about 8.5, about 7.5 to about 9.0, about 8.0 to about 8.5, about 8.0 to about 9.0, or about 8.5 to about 9.0.

In some embodiments, the acidic pH environment has a pH of about 1.0 to about 4.0.

In some embodiments, the acidic pH environment has a pH of about 1.0.

In some embodiments, the pH increases from the acidic pH environment to the pH of about 5.0, about 5.5, about 6.0, about 6.5, about 7.0, about 7.5, about 8.0, about 8.5, or about 9.0.

In some embodiments, the pH increases from the acidic pH environment to the pH of about 6.8.

In some embodiments, upon the pH increase, about 65%, 70%, 75%, 80%, 85%, 90%, 95%, or 100% of maralixibat, or a pharmaceutically acceptable salt thereof, remains dissolved for at least about 1 hour.

In some embodiments, upon the pH increase, at least about 70%, about 75%, about 80%, or about 85% of maralixibat, or a pharmaceutically acceptable salt thereof, remains dissolved for at least about 1 hour.

In some embodiments, about 100% maralixibat, or a pharmaceutically acceptable salt thereof, remains dissolved in the acidic pH environment for about 2 hours upon contact with the acid pH environment.

In some embodiments, about 90% to about 100% of maralixibat, or a pharmaceutically acceptable salt thereof, dissolves in the acidic pH in less than about 15 minutes upon contact with the acid pH environment.

In some embodiments, at least about 90% of maralixibat, or a pharmaceutically acceptable salt thereof, dissolves in the acidic pH in less than about 15 minutes upon contact with the acid pH environment.

In some embodiments, about 100% of maralixibat, or a pharmaceutically acceptable salt thereof, dissolves in the acidic pH in less than about 15 minutes upon contact with the acid pH environment.

In some embodiments, the dosage form comprises about 5 mg to about 50 mg maralixibat or a pharmaceutically acceptable salt thereof based on the free base weight of maralixibat.

In some embodiments, the dosage form comprises about 1 mg to about 250 mg maralixibat or a pharmaceutically acceptable salt thereof based on the free base weight of maralixibat. In some embodiments, the dosage form comprises about 1 mg to about 250 mg, about 1 mg to about 220 mg, about 1 mg to about 200 mg, about 1 mg to about 180 mg, about 1 mg to about 160 mg, about 1 mg to about 150 mg, about 1 mg to about 140 mg, about 1 mg to about 120 mg, about 1 mg to about 110 mg, about 1 mg to about 100 mg, about 1 mg to about 95 mg, about 1 mg to about 90 mg, about 1 mg to about 85 mg, about 1 mg to about 80 mg, about 1 mg to about 75 mg, about 1 mg to about 70 mg, about 1 mg to about 65 mg, about 1 mg to about 60 mg, about 1 mg to about 55 mg, about 1 mg to about 50 mg, about 1 mg to about 45 mg, about 1 mg to about 40 mg, about 1 mg to about 35 mg, about 1 mg to about 30 mg, about 1 mg to about 25 mg, about 1 mg to about 20 mg, about 1 mg to about 15 mg, about 1 mg to about 10 mg, about 1 mg to about 5 mg, about 5 mg to about 250 mg, about 5 mg to about 220 mg, about 5 mg to about 200 mg, about 5 mg to about 180 mg, about 5 mg to about 160 mg, about 5 mg to about 150 mg, about 5 mg to about 140 mg, about 5 mg to about 120 mg, about 5 mg to about 110 mg, about 5 mg to about 100 mg, about 5 mg to about 95 mg, about 5 mg to about 90 mg, about 5 mg to about 85 mg, about 5 mg to about 80 mg, about 5 mg to about 75 mg, about 5 mg to about 70 mg, about 5 mg to about 65 mg, about 5 mg to about 60 mg, about 5 mg to about 55 mg, about 5 mg to about 50 mg, about 5 mg to about 45 mg, about 5 mg to about 40 mg, about 5 mg to about 35 mg, about 5 mg to about 30 mg, about 5 mg to about 25 mg, about 5 mg to about 20 mg, about 5 mg to about 15 mg, about 5 mg to about 10 mg, about 10 mg to about 250 mg, about 10 mg to about 220 mg, about 10 mg to about 200 mg, about 10 mg to about 180 mg, about 10 mg to about 160 mg, about 10 mg to about 150 mg, about 10 mg to about 140 mg, about 10 mg to about 120 mg, about 10 mg to about 110 mg, about 10 mg to about 100 mg, about 10 mg to about 95 mg, about 10 mg to about 90 mg, about 10 mg to about 85 mg, about 10 mg to about 80 mg, about 10 mg to about 75 mg, about 10 mg to about 70 mg, about 10 mg to about 65 mg, about 10 mg to about 60 mg, about 10 mg to about 55 mg, about 10 mg to about 50 mg, about 10 mg to about 45 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 250 mg, about 15 mg to about 220 mg, about 15 mg to about 200 mg, about 15 mg to about 180 mg, about 15 mg to about 160 mg, about 15 mg to about 150 mg, about 15 mg to about 140 mg, about 15 mg to about 120 mg, about 15 mg to about 110 mg, about 15 mg to about 100 mg, about 15 mg to about 95 mg, about 15 mg to about 90 mg, about 15 mg to about 85 mg, about 15 mg to about 80 mg, about 15 mg to about 75 mg, about 15 mg to about 70 mg, about 15 mg to about 65 mg, about 15 mg to about 60 mg, about 15 mg to about 55 mg, about 15 mg to about 50 mg, about 15 mg to about 45 mg, about 15 mg to about 40 mg, about 15 mg to about 35 mg, about 15 mg to about 30 mg, about 15 mg to about 25 mg, about 15 mg to about 20 mg, about 20 mg to about 250 mg, about 20 mg to about 220 mg, about 20 mg to about 200 mg, about 20 mg to about 180 mg, about 20 mg to about 160 mg, about 20 mg to about 150 mg, about 20 mg to about 140 mg, about 20 mg to about 120 mg, about 20 mg to about 110 mg, about 20 mg to about 100 mg, about 20 mg to about 95 mg, about 20 mg to about 90 mg, about 20 mg to about 85 mg, about 20 mg to about 80 mg, about 20 mg to about 75 mg, about 20 mg to about 70 mg, about 20 mg to about 65 mg, about 20 mg to about 60 mg, about 20 mg to about 55 mg, about 20 mg to about 50 mg, about 20 mg to about 45 mg, about 20 mg to about 40 mg, about 20 mg to about 35 mg, about 20 mg to about 30 mg, about 20 mg to about 25 mg, about 25 mg to about 250 mg, about 25 mg to about 220 mg, about 25 mg to about 200 mg, about 25 mg to about 180 mg, about 25 mg to about 160 mg, about 25 mg to about 150 mg, about 25 mg to about 140 mg, about 25 mg to about 120 mg, about 25 mg to about 110 mg, about 25 mg to about 100 mg, about 25 mg to about 95 mg, about 25 mg to about 90 mg, about 25 mg to about 85 mg, about 25 mg to about 80 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 25 mg to about 35 mg, about 25 mg to about 30 mg, about 30 mg to about 250 mg, about 30 mg to about 220 mg, about 30 mg to about 200 mg, about 30 mg to about 180 mg, about 30 mg to about 160 mg, about 30 mg to about 150 mg, about 30 mg to about 140 mg, about 30 mg to about 120 mg, about 30 mg to about 110 mg, about 30 mg to about 100 mg, about 30 mg to about 95 mg, about 30 mg to about 90 mg, about 30 mg to about 85 mg, about 30 mg to about 80 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, about 30 mg to about 35 mg, about 35 mg to about 250 mg, about 35 mg to about 220 mg, about 35 mg to about 200 mg, about 35 mg to about 180 mg, about 35 mg to about 160 mg, about 35 mg to about 150 mg, about 35 mg to about 140 mg, about 35 mg to about 120 mg, about 35 mg to about 110 mg, about 35 mg to about 100 mg, about 35 mg to about 95 mg, about 35 mg to about 90 mg, about 35 mg to about 85 mg, about 35 mg to about 80 mg, about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg, about 35 mg to about 40 mg, about 40 mg to about 250 mg, about 40 mg to about 220 mg, about 40 mg to about 200 mg, about 40 mg to about 180 mg, about 40 mg to about 160 mg, about 40 mg to about 150 mg, about 40 mg to about 140 mg, about 40 mg to about 120 mg, about 40 mg to about 110 mg, about 40 mg to about 100 mg, about 40 mg to about 95 mg, about 40 mg to about 90 mg, about 40 mg to about 85 mg, about 40 mg to about 80 mg, about 40 mg to about 75 mg, about 40 mg to about 70 mg, about 40 mg to about 65 mg, about 40 mg to about 60 mg, about 40 mg to about 55 mg, about 40 mg to about 50 mg, about 40 mg to about 45 mg, about 45 mg to about 250 mg, about 45 mg to about 220 mg, about 45 mg to about 200 mg, about 45 mg to about 180 mg, about 45 mg to about 160 mg, about 45 mg to about 150 mg, about 45 mg to about 140 mg, about 45 mg to about 120 mg, about 45 mg to about 110 mg, about 45 mg to about 100 mg, about 45 mg to about 95 mg, about 45 mg to about 90 mg, about 45 mg to about 85 mg, about 45 mg to about 80 mg, about 45 mg to about 75 mg, about 45 mg to about 70 mg, about 45 mg to about 65 mg, about 45 mg to about 60 mg, about 45 mg to about 55 mg, about 45 mg to about 50 mg, about 50 mg to about 250 mg, about 50 mg to about 220 mg, about 50 mg to about 200 mg, about 50 mg to about 180 mg, about 50 mg to about 160 mg, about 50 mg to about 150 mg, about 50 mg to about 140 mg, about 50 mg to about 120 mg, about 50 mg to about 110 mg, about 50 mg to about 100 mg, about 50 mg to about 95 mg, about 50 mg to about 90 mg, about 50 mg to about 85 mg, about 50 mg to about 80 mg, about 50 mg to about 75 mg, about 50 mg to about 70 mg, about 50 mg to about 65 mg, about 50 mg to about 60 mg, about 50 mg to about 55 mg, about 55 mg to about 250 mg, about 55 mg to about 220 mg, about 55 mg to about 200 mg, about 55 mg to about 180 mg, about 55 mg to about 160 mg, about 55 mg to about 150 mg, about 55 mg to about 140 mg, about 55 mg to about 120 mg, about 55 mg to about 110 mg, about 55 mg to about 100 mg, about 55 mg to about 95 mg, about 55 mg to about 90 mg, about 55 mg to about 85 mg, about 55 mg to about 80 mg, about 55 mg to about 75 mg, about 55 mg to about 70 mg, about 55 mg to about 65 mg, about 55 mg to about 60 mg, about 60 mg to about 250 mg, about 60 mg to about 220 mg, about 60 mg to about 200 mg, about 60 mg to about 180 mg, about 60 mg to about 160 mg, about 60 mg to about 150 mg, about 60 mg to about 140 mg, about 60 mg to about 120 mg, about 60 mg to about 110 mg, about 60 mg to about 100 mg, about 60 mg to about 95 mg, about 60 mg to about 90 mg, about 60 mg to about 85 mg, about 60 mg to about 80 mg, about 60 mg to about 75 mg, about 60 mg to about 70 mg, about 60 mg to about 65 mg, about 65 mg to about 250 mg, about 65 mg to about 220 mg, about 65 mg to about 200 mg, about 65 mg to about 180 mg, about 65 mg to about 160 mg, about 65 mg to about 150 mg, about 65 mg to about 140 mg, about 65 mg to about 120 mg, about 65 mg to about 110 mg, about 65 mg to about 100 mg, about 65 mg to about 95 mg, about 65 mg to about 90 mg, about 65 mg to about 85 mg, about 65 mg to about 80 mg, about 65 mg to about 75 mg, about 65 mg to about 70 mg, about 70 mg to about 250 mg, about 70 mg to about 220 mg, about 70 mg to about 200 mg, about 70 mg to about 180 mg, about 70 mg to about 160 mg, about 70 mg to about 150 mg, about 70 mg to about 140 mg, about 70 mg to about 120 mg, about 70 mg to about 110 mg, about 70 mg to about 100 mg, about 70 mg to about 95 mg, about 70 mg to about 90 mg, about 70 mg to about 85 mg, about 70 mg to about 80 mg, about 70 mg to about 75 mg, about 75 mg to about 250 mg, about 75 mg to about 220 mg, about 75 mg to about 200 mg, about 75 mg to about 180 mg, about 75 mg to about 160 mg, about 75 mg to about 150 mg, about 75 mg to about 140 mg, about 75 mg to about 120 mg, about 75 mg to about 110 mg, about 75 mg to about 100 mg, about 75 mg to about 95 mg, about 75 mg to about 90 mg, about 75 mg to about 85 mg, about 75 mg to about 80 mg, about 80 mg to about 250 mg, about 80 mg to about 220 mg, about 80 mg to about 200 mg, about 80 mg to about 180 mg, about 80 mg to about 160 mg, about 80 mg to about 150 mg, about 80 mg to about 140 mg, about 80 mg to about 120 mg, about 80 mg to about 110 mg, about 80 mg to about 100 mg, about 80 mg to about 95 mg, about 80 mg to about 90 mg, about 80 mg to about 85 mg, about 85 mg to about 250 mg, about 85 mg to about 220 mg, about 85 mg to about 200 mg, about 85 mg to about 180 mg, about 85 mg to about 160 mg, about 85 mg to about 150 mg, about 85 mg to about 140 mg, about 85 mg to about 120 mg, about 85 mg to about 110 mg, about 85 mg to about 100 mg, about 85 mg to about 95 mg, about 85 mg to about 90 mg, about 90 mg to about 250 mg, about 90 mg to about 220 mg, about 90 mg to about 200 mg, about 90 mg to about 180 mg, about 90 mg to about 160 mg, about 90 mg to about 150 mg, about 90 mg to about 140 mg, about 90 mg to about 120 mg, about 90 mg to about 110 mg, about 90 mg to about 100 mg, about 90 mg to about 95 mg, about 95 mg to about 250 mg, about 95 mg to about 220 mg, about 95 mg to about 200 mg, about 95 mg to about 180 mg, about 95 mg to about 160 mg, about 95 mg to about 150 mg, about 95 mg to about 140 mg, about 95 mg to about 120 mg, about 95 mg to about 110 mg, about 95 mg to about 100 mg, about 100 mg to about 250 mg, about 100 mg to about 220 mg, about 100 mg to about 200 mg, about 100 mg to about 180 mg, about 100 mg to about 160 mg, about 100 mg to about 150 mg, about 100 mg to about 140 mg, about 100 mg to about 120 mg, about 100 mg to about 110 mg, about 110 mg to about 250 mg, about 110 mg to about 220 mg, about 110 mg to about 200 mg, about 110 mg to about 180 mg, about 110 mg to about 160 mg, about 110 mg to about 150 mg, about 110 mg to about 140 mg, about 110 mg to about 120 mg, about 120 mg to about 250 mg, about 120 mg to about 220 mg, about 120 mg to about 200 mg, about 120 mg to about 180 mg, about 120 mg to about 160 mg, about 120 mg to about 150 mg, about 120 mg to about 140 mg, about 140 mg to about 250 mg, about 140 mg to about 220 mg, about 140 mg to about 200 mg, about 140 mg to about 180 mg, about 140 mg to about 160 mg, about 140 mg to about 150 mg, about 150 mg to about 250 mg, about 150 mg to about 220 mg, about 150 mg to about 200 mg, about 150 mg to about 180 mg, about 150 mg to about 160 mg, about 160 mg to about 250 mg, about 160 mg to about 220 mg, about 160 mg to about 200 mg, about 160 mg to about 180 mg, about 180 mg to about 250 mg, about 180 mg to about 220 mg, about 180 mg to about 200 mg, about 200 mg to about 250 mg, about 200 mg to about 220 mg, or about 220 mg to about 250 mg maralixibat or a pharmaceutically acceptable salt thereof based on the free base weight of maralixibat.

In some embodiments, the dosage form comprises about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 140 mg, about 150 mg, about 160 mg, about 180 mg, about 200 mg, about 220 mg, or about 250 mg maralixibat or a pharmaceutically acceptable salt thereof based on the free base weight of maralixibat.

In some embodiments, the dosage form comprises about 5 mg, about 10 mg, about 20 mg, about 30 mg, about 40 mg, or about 50 mg maralixibat or a pharmaceutically acceptable salt thereof based on the free base weight of maralixibat.

In some embodiments, the dosage form comprises about 10 mg maralixibat or a pharmaceutically acceptable salt thereof based on the free base weight of maralixibat, wherein upon the pH increase, at least about 50%, about 55%, about 60%, about 65%, about 70%, about 75%, about 80%, about 85%, about 90%, about 95% of maralixibat, or a pharmaceutically acceptable salt thereof, remains dissolved for at least about 1 hour.

In some embodiments, the dosage form comprises about 10 mg maralixibat or a pharmaceutically acceptable salt thereof based on the free base weight of maralixibat, wherein upon the pH increase, at least about 68% of maralixibat, or a pharmaceutically acceptable salt thereof, remains dissolved for at least about 1 hour.

In some embodiments, the dosage form comprises about 50 mg maralixibat or a pharmaceutically acceptable salt thereof based on the free base weight of maralixibat, wherein upon the pH increase, at least about 50%, about 55%, about 60%, about 65%, about 70%, about 75%, about 80%, about 85%, about 90%, about 95% of maralixibat, or a pharmaceutically acceptable salt thereof, remains dissolved for at least about 1 hour.

In some embodiments, the dosage form comprises about 50 mg maralixibat or a pharmaceutically acceptable salt thereof based on the free base weight of maralixibat, wherein upon the pH increase, at least about 80% of maralixibat, or a pharmaceutically acceptable salt thereof, remains dissolved for at least about 1 hour.

In some embodiments, the dosage form comprises about 50 mg maralixibat or a pharmaceutically acceptable salt thereof based on the free base weight of maralixibat, wherein upon the pH increase, at least about 85% of maralixibat, or a pharmaceutically acceptable salt thereof, remains dissolved for at least about 1 hour.

In some embodiments, the one or more excipients does not comprise metal ions.

In some embodiments, the dosage form comprising maralixibat, or a pharmaceutically acceptable salt thereof, further comprises the following excipients:
(i) a diluent,
(ii) a glidant in an amount of about 0.1 to about 2% (w/w),
(iii) a lubricant in an amount of about 6% to about 12% (w/w); and optionally
(iv) a disintegrant in an amount of about 3% to about 7% (w/w).

In some embodiments,
(i) the diluent is selected from the group consisting of a sugar, dextrates, dextrin, dextrose, lactose, lactose monohydrate, mannitol, sorbitol, starch, cellulose, modified celluloses, and any combinations thereof;
(ii) the glidant is selected from the group consisting of silicon dioxide, talc, corn starch, and any combinations thereof,
(iii) the lubricant is selected from the group consisting of talc, stearic acid, leucine, glyceryl behenate, glyceryl dibehenate, glyceryl palmitostearate, hydrogenated vegetable oil, and any combinations thereof; and/or
(iv) the disintegrant is selected from the group consisting of crospovidone, starch, and a combination thereof.

In some embodiments, the dosage form comprising about 5 mg to about 50 mg maralixibat, or a pharmaceutically acceptable salt thereof, based on the free base weight of maralixibat, and:
(i) about 50% (w/w) MCC and about 25% (w/w) lactose monohydrate;
(ii) about 0.5% (w/w) silicon dioxide;
(iii) about 9% (w/w) glyceryl palmitostearate; and
(iv) about 5% (w/w) crospovidone.

In some embodiments, the dosage form comprises about 50 mg maralixibat, or a pharmaceutically acceptable salt thereof, based on the free base weight of maralixibat, and
(i) about 50% (w/w) MCC and about 25% (w/w) lactose monohydrate;
(ii) about 0.5% (w/w) silicon dioxide;
(iii) about 9% (w/w) glyceryl palmitostearate; and
(iv) about 5% (w/w) crospovidone.

In one embodiment, the dosage form as described above is formulated for once-daily or twice-daily administration. In one embodiment, the dosage form is formulated for once-daily administration.

Provided herein is a method of administering maralixibat, or a pharmaceutically acceptable salt thereof, to a subject in need thereof, comprising administering to the subject the dosage form as described herein.

Methods of Preparing Pharmaceutical Compositions

Provided herein is a method of preparing the pharmaceutical composition comprising: milling maralixibat, or a pharmaceutically acceptable salt thereof;
combining the milled maralixibat, or a pharmaceutically acceptable salt thereof, with the diluent, the glidant, the lubricant; and optionally the disintegrant to form an admixture; and
compacting the admixture to form the pharmaceutical composition.

In some embodiments, the milling process applies energy through mechanical forces to break down larger particles into smaller sizes.

In some embodiments, the milling process is executed with grinding media, screen mills, conical mills, hammer mills, vibration mills, sieves, oscillating granulators, pegs, pebbles, or rods.

In some embodiments, the particles are passed through the milling device multiple times with or without decreasing mesh size depending on device.

In some embodiments, the particles are forced through the milling device and are torn or crushed.

In some embodiments, milling may also be referred to as grinding, granulation, size reduction, comminution, or pulverization.

In some embodiments, the milling is loop milling or pin milling.

In some embodiments, loop milling is performed with an oval chamber mill, spiral jet mill, or loop jet mill.

In some embodiments, loop milling uses pressurized gas to create high particle velocity and high-energy impact between particles and between the particles and the mill chamber.

In some embodiments, size reduction is achieved by particle-to-particle collisions.

In some embodiments, nitrogen is used as the loop milling gas.

In some embodiments, pin milling is performed with a pin mill, pin mill grinder, or disc mill.

In some embodiments, the pin mill grinder chamber consists of two discs or plates each containing circular rows of pins or vertical projections that are arranged in concentric circles moving past one another.

In some embodiments, either one or both disks of the pin mill are rotated at high speeds and the speed of one or both discs can be adjusted to vary the range of particle size.

In some embodiments, pin milling relies on particles repeatedly impacting pins as the material is fed into the space between the discs of the milling chamber.

In another embodiment, the milled maralixibat, or a pharmaceutically acceptable salt thereof, has a particle size distribution with a Dv90 of less than about 2500 μm.

In another embodiment, the milled maralixibat, or a pharmaceutically acceptable salt thereof, has a particle size distribution with a Dv90 of less than about 1500 μm.

In another embodiment, the milled maralixibat, or a pharmaceutically acceptable salt thereof, has a particle size distribution with a Dv90 of less than about 850 μm.

In another embodiment, the milled maralixibat, or a pharmaceutically acceptable salt thereof, has a particle size distribution with a Dv90 of less than about 700 μm.

In another embodiment, the milled maralixibat, or a pharmaceutically acceptable salt thereof, has a particle size distribution with a Dv90 of less than about 500 μm.

In another embodiment, the milled maralixibat, or a pharmaceutically acceptable salt thereof, has a particle size distribution with a Dv90 of less than about 300 μm.

In another embodiment, the milled maralixibat, or a pharmaceutically acceptable salt thereof, has a particle size distribution with a Dv90 of less than about 100 μm.

In another embodiment, the milled maralixibat, or a pharmaceutically acceptable salt thereof, has a particle size distribution with a Dv90 of less than about 60 μm.

Generally, the compounds of this invention are administered in a therapeutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The compounds of this invention can also be administered in sustained release forms or from sustained release drug delivery systems. A description of representative sustained release materials can be found in Remington's Pharmaceutical Sciences.

The tablets or pills containing the compound of maralixibat or a pharmaceutically acceptable salt thereof can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The therapeutic dosage of the compounds of the invention can vary according to, for example, the particular use for which the treatment is made, the manner of administration of the compound, the health and condition of the patient, and the judgment of the prescribing physician. The proportion or concentration of the compounds of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Methods of Treatment

Provided herein is a method of treating cholestatic pruritus in a subject in need thereof, comprising administering to the subject a therapeutically effective amount of the pharmaceutical composition.

Provided herein is also a method of treating a disease or condition characterized by cholestatic pruritus in a subject in need thereof, comprising administering to the subject a therapeutically effective amount of the pharmaceutical composition.

In one embodiment, the cholestatic pruritus is associated with Alagille syndrome (ALGS).

In another embodiment, the subject has Alagille syndrome (ALGS).

In a further embodiment, the subject is 2 months of age and older.

In a further embodiment, the subject is 3 months of age and older.

In one embodiment, the subject is a pediatric subject between 2 months and 18 years of age. In one embodiment, the subject is an adult who is 18 years of age or older.

Provided herein is a method of treating cholestatic liver disease or condition in a subject in need thereof, comprising administering to the subject a therapeutically effective amount of the pharmaceutical composition according to the present disclosure.

In another embodiment, the cholestatic liver disease or condition is selected from the group consisting of obstructive cholestasis, non-obstructive cholestasis, extrahepatic cholestasis, intrahepatic cholestasis, primary intrahepatic cholestasis, secondary intrahepatic cholestasis, progressive familial intrahepatic cholestasis (PFIC), PFIC type 1, PFIC type 2, PFIC type 3, PFIC type 4, PFIC type 5, PFIC type 6, benign recurrent intrahepatic cholestasis (BRIC), BRIC type 1, BRIC type 2, BRIC type 3, total parenteral nutrition associated cholestasis, paraneoplastic cholestasis, Stauffer syndrome, intrahepatic cholestasis of pregnancy, contraceptive-associated cholestasis, drug-associated cholestasis, infection-associated cholestasis, Dubin-Johnson Syndrome, primary biliary cirrhosis (PBC), primary sclerosing cholangitis (PSC), gallstone disease, Alagille syndrome, Dubin-Johnson Syndrome, biliary atresia, post-Kasai biliary atresia, post-liver transplantation biliary atresia, post-liver transplantation cholestasis, post-liver transplantation associated liver disease, intestinal failure associated liver disease, bile acid mediated liver injury, multidrug resistance-associated protein 2 (MRP2) deficiency syndrome, and neonatal sclerosing cholangitis.

In one embodiment, the cholestatic liver disease or condition is Alagille syndrome (ALGS).

In one embodiment, the cholestatic liver disease is progressive familial intrahepatic cholestasis (PFIC).

In one embodiment, the cholestatic liver disease is biliary atresia.

In one embodiment, the composition decreases the levels of serum bile acids or hepatic bile acids, reduces bilirubin, reduces liver enzymes, lowers intraenterocyte bile acids/salts, or reduces necrosis and/or damage to hepatocellular architecture.

In an additional embodiment, the composition decreases serum bile acid or hepatic bile acid levels in the patient by at least about 10%.

In an additional embodiment, the composition decreases serum bile acid or hepatic bile acid levels in the patient by at least about 20%.

In an additional embodiment, the composition decreases serum bile acid or hepatic bile acid levels in the patient by at least about 30%.

In an additional embodiment, the composition decreases serum bile acid or hepatic bile acid levels in the patient by at least about 40%.

In an additional embodiment, the composition decreases serum bile acid or hepatic bile acid levels in the patient by at least about 50%.

In some embodiments, less than 10% of maralixibat, or a pharmaceutically acceptable salt thereof, is systemically absorbed upon oral administration.

In some embodiments, less than 7% of maralixibat, or a pharmaceutically acceptable salt thereof, is systemically absorbed upon oral administration.

In some embodiments, less than 5% of maralixibat, or a pharmaceutically acceptable salt thereof, is systemically absorbed upon oral administration.

In some embodiments, less than 3% of maralixibat, or a pharmaceutically acceptable salt thereof, is systemically absorbed upon oral administration.

In some embodiments, less than 1% of maralixibat, or a pharmaceutically acceptable salt thereof, is systemically absorbed upon oral administration.

In some embodiments, the composition is administered at a dosage comprising from about 1 mg to about 250 mg maralixibat or a pharmaceutically acceptable salt thereof based on the free base weight of maralixibat. In some embodiments, the composition is administered at a dosage comprising from about 1 mg to about 250 mg, about 1 mg to about 220 mg, about 1 mg to about 200 mg, about 1 mg to about 180 mg, about 1 mg to about 160 mg, about 1 mg to about 150 mg, about 1 mg to about 140 mg, about 1 mg to about 120 mg, about 1 mg to about 110 mg, about 1 mg to about 100 mg, about 1 mg to about 95 mg, about 1 mg to about 90 mg, about 1 mg to about 85 mg, about 1 mg to about 80 mg, about 1 mg to about 75 mg, about 1 mg to about 70 mg, about 1 mg to about 65 mg, about 1 mg to about 60 mg, about 1 mg to about 55 mg, about 1 mg to about 50 mg, about 1 mg to about 45 mg, about 1 mg to about 40 mg, about 1 mg to about 35 mg, about 1 mg to about 30 mg, about 1 mg to about 25 mg, about 1 mg to about 20 mg, about 1 mg to about 15 mg, about 1 mg to about 10 mg, about 1 mg to about 5 mg, about 5 mg to about 250 mg, about 5 mg to about 220 mg, about 5 mg to about 200 mg, about 5 mg to about 180 mg, about 5 mg to about 160 mg, about 5 mg to about 150 mg, about 5 mg to about 140 mg, about 5 mg to about 120 mg, about 5 mg to about 110 mg, about 5 mg to about 100 mg, about 5 mg to about 95 mg, about 5 mg to about 90 mg, about 5 mg to about 85 mg, about 5 mg to about 80 mg, about 5 mg to about 75 mg, about 5 mg to about 70 mg, about 5 mg to about 65 mg, about 5 mg to about 60 mg, about 5 mg to about 55 mg, about 5 mg to about 50 mg, about 5 mg to about 45 mg, about 5 mg to about 40 mg, about 5 mg to about 35 mg, about 5 mg to about 30 mg, about 5 mg to about 25 mg, about 5 mg to about 20 mg, about 5 mg to about 15 mg, about 5 mg to about 10 mg, about 10 mg to about 250 mg, about 10 mg to about 220 mg, about 10 mg to about 200 mg, about 10 mg to about 180 mg, about 10 mg to about 160 mg, about 10 mg to about 150 mg, about 10 mg to about 140 mg, about 10 mg to about 120 mg, about 10 mg to about 110 mg, about 10 mg to about 100 mg, about 10 mg to about 95 mg, about 10 mg to about 90 mg, about 10 mg to about 85 mg, about 10 mg to about 80 mg, about 10 mg to about 75 mg, about 10 mg to about 70 mg, about 10 mg to about 65 mg, about 10 mg to about 60 mg, about 10 mg to about 55 mg, about 10 mg to about 50 mg, about 10 mg to about 45 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 250 mg, about 15 mg to about 220 mg, about 15 mg to about 200 mg, about 15 mg to about 180 mg, about 15 mg to about 160 mg, about 15 mg to about 150 mg, about 15 mg to about 140 mg, about 15 mg to about 120 mg, about 15 mg to about 110 mg, about 15 mg to about 100 mg, about 15 mg to about 95 mg, about 15 mg to about 90 mg, about 15 mg to about 85 mg, about 15 mg to about 80 mg, about 15 mg to about 75 mg, about 15 mg to about 70 mg, about 15 mg to about 65 mg, about 15 mg to about 60 mg, about 15 mg to about 55 mg, about 15 mg to about 50 mg, about 15 mg to about 45 mg, about 15 mg to about 40 mg, about 15 mg to about 35 mg, about 15 mg to about 30 mg, about 15 mg to about 25 mg, about 15 mg to about 20 mg, about 20 mg to about 250 mg, about 20 mg to about 220 mg, about 20 mg to about 200 mg, about 20 mg to about 180 mg, about 20 mg to about 160 mg, about 20 mg to about 150 mg, about 20 mg to about 140 mg, about 20 mg to about 120 mg, about 20 mg to about 110 mg, about 20 mg to about 100 mg, about 20 mg to about 95 mg, about 20 mg to about 90 mg, about 20 mg to about 85 mg, about 20 mg to about 80 mg, about 20 mg to about 75 mg, about 20 mg to about 70 mg, about 20 mg to about 65 mg, about 20 mg to about 60 mg, about 20 mg to about 55 mg, about 20 mg to about 50 mg, about 20 mg to about 45 mg, about 20 mg to about 40 mg, about 20 mg to about 35 mg, about 20 mg to about 30 mg, about 20 mg to about 25 mg, about 25 mg to about 250 mg, about 25 mg to about 220 mg, about 25 mg to about 200 mg, about 25 mg to about 180 mg, about 25 mg to about 160 mg, about 25 mg to about 150 mg, about 25 mg to about 140 mg, about 25 mg to about 120 mg, about 25 mg to about 110 mg, about 25 mg to about 100 mg, about 25 mg to about 95 mg, about 25 mg to about 90 mg, about 25 mg to about 85 mg, about 25 mg to about 80 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 25 mg to about 35 mg, about 25 mg to about 30 mg, about 30 mg to about 250 mg, about 30 mg to about 220 mg, about 30 mg to about 200 mg, about 30 mg to about 180 mg, about 30 mg to about 160 mg, about 30 mg to about 150 mg, about 30 mg to about 140 mg, about 30 mg to about 120 mg, about 30 mg to about 110 mg, about 30 mg to about 100 mg, about 30 mg to about 95 mg, about 30 mg to about 90 mg, about 30 mg to about 85 mg, about 30 mg to about 80 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, about 30 mg to about 35 mg, about 35 mg to about 250 mg, about 35 mg to about 220 mg, about 35 mg to about 200 mg, about 35 mg to about 180 mg, about 35 mg to about 160 mg, about 35 mg to about 150 mg, about 35 mg to about 140 mg, about 35 mg to about 120 mg, about 35 mg to about 110 mg, about 35 mg to about 100 mg, about 35 mg to about 95 mg, about 35 mg to about 90 mg, about 35 mg to about 85 mg, about 35 mg to about 80 mg, about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg, about 35 mg to about 40 mg, about 40 mg to about 250 mg, about 40 mg to about 220 mg, about 40 mg to about 200 mg, about 40 mg to about 180 mg, about 40 mg to about 160 mg, about 40 mg to about 150 mg, about 40 mg to about 140 mg, about 40 mg to about 120 mg, about 40 mg to about 110 mg, about 40 mg to about 100 mg, about 40 mg to about 95 mg, about 40 mg to about 90 mg, about 40 mg to about 85 mg, about 40 mg to about 80 mg, about 40 mg to about 75 mg, about 40 mg to about 70 mg, about 40 mg to about 65 mg, about 40 mg to about 60 mg, about 40 mg to about 55 mg, about 40 mg to about 50 mg, about 40 mg to about 45 mg, about 45 mg to about 250 mg, about 45 mg to about 220 mg, about 45 mg to about 200 mg, about 45 mg to about 180 mg, about 45 mg to about 160 mg, about 45 mg to about 150 mg, about 45 mg to about 140 mg, about 45 mg to about 120 mg, about 45 mg to about 110 mg, about 45 mg to about 100 mg, about 45 mg to about 95 mg, about 45 mg to about 90 mg, about 45 mg to about 85 mg, about 45 mg to about 80 mg, about 45 mg to about 75 mg, about 45 mg to about 70 mg, about 45 mg to about 65 mg, about 45 mg to about 60 mg, about 45 mg to about 55 mg, about 45 mg to about 50 mg, about 50 mg to about 250 mg, about 50 mg to about 220 mg, about 50 mg to about 200 mg, about 50 mg to about 180 mg, about 50 mg to about 160 mg, about 50 mg to about 150 mg, about 50 mg to about 140 mg, about 50 mg to about 120 mg, about 50 mg to about 110 mg, about 50 mg to about 100 mg, about 50 mg to about 95 mg, about 50 mg to about 90 mg, about 50 mg to about 85 mg, about 50 mg to about 80 mg, about 50 mg to about 75 mg, about 50 mg to about 70 mg, about 50 mg to about 65 mg, about 50 mg to about 60 mg, about 50 mg to about 55 mg, about 55 mg to about 250 mg, about 55 mg to about 220 mg, about 55 mg to about 200 mg, about 55 mg to about 180 mg, about 55 mg to about 160 mg, about 55 mg to about 150 mg, about 55 mg to about 140 mg, about 55 mg to about 120 mg, about 55 mg to about 110 mg, about 55 mg to about 100 mg, about 55 mg to about 95 mg, about 55 mg to about 90 mg, about 55 mg to about 85 mg, about 55 mg to about 80 mg, about 55 mg to about 75 mg, about 55 mg to about 70 mg, about 55 mg to about 65 mg, about 55 mg to about 60 mg, about 60 mg to about 250 mg, about 60 mg to about 220 mg, about 60 mg to about 200 mg, about 60 mg to about 180 mg, about 60 mg to about 160 mg, about 60 mg to about 150 mg, about 60 mg to about 140 mg, about 60 mg to about 120 mg, about 60 mg to about 110 mg, about 60 mg to about 100 mg, about 60 mg to about 95 mg, about 60 mg to about 90 mg, about 60 mg to about 85 mg, about 60 mg to about 80 mg, about 60 mg to about 75 mg, about 60 mg to about 70 mg, about 60 mg to about 65 mg, about 65 mg to about 250 mg, about 65 mg to about 220 mg, about 65 mg to about 200 mg, about 65 mg to about 180 mg, about 65 mg to about 160 mg, about 65 mg to about 150 mg, about 65 mg to about 140 mg, about 65 mg to about 120 mg, about 65 mg to about 110 mg, about 65 mg to about 100 mg, about 65 mg to about 95 mg, about 65 mg to about 90 mg, about 65 mg to about 85 mg, about 65 mg to about 80 mg, about 65 mg to about 75 mg, about 65 mg to about 70 mg, about 70 mg to about 250 mg, about 70 mg to about 220 mg, about 70 mg to about 200 mg, about 70 mg to about 180 mg, about 70 mg to about 160 mg, about 70 mg to about 150 mg, about 70 mg to about 140 mg, about 70 mg to about 120 mg, about 70 mg to about 110 mg, about 70 mg to about 100 mg, about 70 mg to about 95 mg, about 70 mg to about 90 mg, about 70 mg to about 85 mg, about 70 mg to about 80 mg, about 70 mg to about 75 mg, about 75 mg to about 250 mg, about 75 mg to about 220 mg, about 75 mg to about 200 mg, about 75 mg to about 180 mg, about 75 mg to about 160 mg, about 75 mg to about 150 mg, about 75 mg to about 140 mg, about 75 mg to about 120 mg, about 75 mg to about 110 mg, about 75 mg to about 100 mg, about 75 mg to about 95 mg, about 75 mg to about 90 mg, about 75 mg to about 85 mg, about 75 mg to about 80 mg, about 80 mg to about 250 mg, about 80 mg to about 220 mg, about 80 mg to about 200 mg, about 80 mg to about 180 mg, about 80 mg to about 160 mg, about 80 mg to about 150 mg, about 80 mg to about 140 mg, about 80 mg to about 120 mg, about 80 mg to about 110 mg, about 80 mg to about 100 mg, about 80 mg to about 95 mg, about 80 mg to about 90 mg, about 80 mg to about 85 mg, about 85 mg to about 250 mg, about 85 mg to about 220 mg, about 85 mg to about 200 mg, about 85 mg to about 180 mg, about 85 mg to about 160 mg, about 85 mg to about 150 mg, about 85 mg to about 140 mg, about 85 mg to about 120 mg, about 85 mg to about 110 mg, about 85 mg to about 100 mg, about 85 mg to about 95 mg, about 85 mg to about 90 mg, about 90 mg to about 250 mg, about 90 mg to about 220 mg, about 90 mg to about 200 mg, about 90 mg to about 180 mg, about 90 mg to about 160 mg, about 90 mg to about 150 mg, about 90 mg to about 140 mg, about 90 mg to about 120 mg, about 90 mg to about 110 mg, about 90 mg to about 100 mg, about 90 mg to about 95 mg, about 95 mg to about 250 mg, about 95 mg to about 220 mg, about 95 mg to about 200 mg, about 95 mg to about 180 mg, about 95 mg to about 160 mg, about 95 mg to about 150 mg, about 95 mg to about 140 mg, about 95 mg to about 120 mg, about 95 mg to about 110 mg, about 95 mg to about 100 mg, about 100 mg to about 250 mg, about 100 mg to about 220 mg, about 100 mg to about 200 mg, about 100 mg to about 180 mg, about 100 mg to about 160 mg, about 100 mg to about 150 mg, about 100 mg to about 140 mg, about 100 mg to about 120 mg, about 100 mg to about 110 mg, about 110 mg to about 250 mg, about 110 mg to about 220 mg, about 110 mg to about 200 mg, about 110 mg to about 180 mg, about 110 mg to about 160 mg, about 110 mg to about 150 mg, about 110 mg to about 140 mg, about 110 mg to about 120 mg, about 120 mg to about 250 mg, about 120 mg to about 220 mg, about 120 mg to about 200 mg, about 120 mg to about 180 mg, about 120 mg to about 160 mg, about 120 mg to about 150 mg, about 120 mg to about 140 mg, about 140 mg to about 250 mg, about 140 mg to about 220 mg, about 140 mg to about 200 mg, about 140 mg to about 180 mg, about 140 mg to about 160 mg, about 140 mg to about 150 mg, about 150 mg to about 250 mg, about 150 mg to about 220 mg, about 150 mg to about 200 mg, about 150 mg to about 180 mg, about 150 mg to about 160 mg, about 160 mg to about 250 mg, about 160 mg to about 220 mg, about 160 mg to about 200 mg, about 160 mg to about 180 mg, about 180 mg to about 250 mg, about 180 mg to about 220 mg, about 180 mg to about 200 mg, about 200 mg to about 250 mg, about 200 mg to about 220 mg, or about 220 mg to about 250 mg maralixibat or a pharmaceutically acceptable salt thereof based on the free base weight of maralixibat.

In some embodiments, the composition is administered at a dosage comprising about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 140 mg, about 150 mg, about 160 mg, about 180 mg, about 200 mg, about 220 mg, or about 250 mg maralixibat or a pharmaceutically acceptable salt thereof based on the free base weight of maralixibat.

In some embodiments, the composition is administered at a dosage comprising from about 5 mg to about 50 mg maralixibat, or a pharmaceutically acceptable salt thereof based on the free base weight of maralixibat.

In an additional embodiment, the composition decreases pruritus.

As a further aspect of the invention there are provided the present compositions and dosage forms for use as a pharmaceutical especially in the treatment or prevention of the aforementioned conditions and diseases. Also provided herein is the use of the present compositions and dosage forms in the manufacture of a medicament for the treatment or prevention of one of the aforementioned conditions and diseases.

When used to prevent the onset of any of the aforementioned conditions and diseases, the compositions and dosage forms of this invention can be administered to a patient at risk for developing the condition or disorder, typically on the advice and under the supervision of a physician, in the dosage forms described above. Patients at risk for developing a particular condition generally include those that have a family history of the condition, or those who have been identified by genetic testing or screening to be particularly susceptible to developing the condition.

The compositions and dosage forms of this invention can be administered as the sole active agent or they can be administered in combination with other agents, including other compounds, compositions and dosage forms that demonstrate the same or a similar therapeutic activity and are determined to safe and efficacious for such combined administration.

In some embodiments, the composition is administered with a second agent selected from a bile acid sequestrant or binder.

In one embodiment, the composition is administered before ingestion of food.

In one embodiment, the composition is administered less than about 60 minutes or less than about 30 minutes before ingestion of food.

In one embodiment, the composition is administered orally.

In one embodiment, the composition is administered once daily (QD) or twice daily (BID).

In one embodiment, the composition is administered once daily.

In one embodiment, the composition is administered as an ileal-pH sensitive release or an enterically coated formulation.

In another embodiment, the composition is administered with a vitamin supplement.

In another embodiment, the vitamin supplement comprises a fat-soluble vitamin.

In another embodiment, the fat-soluble vitamin is selected from the group consisting of vitamin A, D, E, and K.

Further provided herein is a method of preparing a dosage form as described herein, comprising:
  milling maralixibat, or a pharmaceutically acceptable salt thereof;
  combining the milled maralixibat, or a pharmaceutically acceptable salt thereof, with the diluent, the glidant, the lubricant; and optionally the disintegrant to form an admixture; and
  compacting the admixture to form the dosage form.

In some embodiments, the milling is loop milling or pin milling.

In some embodiments, the milled maralixibat, or a pharmaceutically acceptable salt thereof, has a particle size distribution with a Dv90 of less than about 850 μm.

In some embodiments, the milled maralixibat, or a pharmaceutically acceptable salt thereof, has a particle size distribution with a Dv90 of less than about 100 μm.

In some embodiments, the milled maralixibat, or a pharmaceutically acceptable salt thereof, has a particle size distribution with a Dv90 of less than about 60 μm.

Also provided herein is a method of treating cholestatic pruritus in a subject in need thereof, comprising administering to the subject a dosage form as described herein.

Also provided herein is a method of treating a disease or condition characterized by cholestatic pruritus in a subject in need thereof, comprising administering to the subject a dosage form as described herein.

In one embodiment, the cholestatic pruritus is associated with Alagille syndrome (ALGS).

In another embodiment, the subject has Alagille syndrome (ALGS).

In a further embodiment, the subject is 2 months of age and older.

In a further embodiment, the subject is 3 months of age and older.

In one embodiment, the subject is a pediatric subject between 2 months and 18 years of age. In one embodiment, the subject is an adult who is 18 years of age or older.

Also provided herein is a method of treating cholestatic liver disease or condition in a subject in need thereof, comprising administering to the subject a dosage form as described herein.

In some embodiments, the cholestatic liver disease or condition is selected from the group consisting of obstructive cholestasis, non-obstructive cholestasis, extrahepatic cholestasis, intrahepatic cholestasis, primary intrahepatic cholestasis, secondary intrahepatic cholestasis, progressive familial intrahepatic cholestasis (PFIC), PFIC type 1, PFIC type 2, PFIC type 3, PFIC type 4, PFIC type 5, PFIC type 6, benign recurrent intrahepatic cholestasis (BRIC), BRIC type 1, BRIC type 2, BRIC type 3, total parenteral nutrition associated cholestasis, paraneoplastic cholestasis, Stauffer syndrome, intrahepatic cholestasis of pregnancy, contraceptive-associated cholestasis, drug-associated cholestasis, infection-associated cholestasis, Dubin-Johnson Syndrome, primary biliary cirrhosis (PBC), primary sclerosing cholangitis (PSC), gallstone disease, Alagille syndrome, Dubin-Johnson Syndrome, biliary atresia, post-Kasai biliary atresia, post-liver transplantation biliary atresia, post-liver transplantation cholestasis, post-liver transplantation associated liver disease, intestinal failure associated liver disease, bile acid mediated liver injury, MRP2 deficiency syndrome, and neonatal sclerosing cholangitis.

In some embodiments, the cholestatic liver disease or condition is Alagille syndrome (ALGS).

In some embodiments, the cholestatic liver disease is progressive familial intrahepatic cholestasis (PFIC).

In some embodiments, the cholestatic liver disease is biliary atresia (BA).

In some embodiments, the dosage form decreases the levels of serum bile acids or hepatic bile acids, reduces bilirubin, reduces liver enzymes, lowers intraenterocyte bile acids/salts, and/or reduces necrosis and/or damage to hepatocellular architecture.

In some embodiments, the dosage form decreases serum bile acid or hepatic bile acid levels in the patient by at least about 20%.

In some embodiments, the dosage form decreases serum bile acid or hepatic bile acid levels in the patient by at least about 30%.

In some embodiments, the dosage form decreases serum bile acid or hepatic bile acid levels in the patient by at least about 40%.

In some embodiments, less than 10% of maralixibat, or a pharmaceutically acceptable salt thereof, is systemically absorbed upon oral administration.

In some embodiments, the dosage form decreases pruritus.

In some embodiments, the dosage form is administered with a second agent selected from a bile acid sequestrant or binder.

In some embodiments, the dosage form is administered before ingestion of food.

In some embodiments, the dosage form is administered less than about 60 minutes or less than about 30 minutes before ingestion of food.

In some embodiments, the dosage form is administered orally.

In one embodiment, the dosage form is administered once daily (QD) or twice daily (BID).

In one embodiment, the dosage form is administered once daily.

In some embodiments, the dosage form is administered as an ileal-pH sensitive release or an enterically coated formulation.

In some embodiments, the dosage form is administered with a vitamin supplement.

In some embodiments, the vitamin supplement comprises a fat-soluble vitamin.

In some embodiments, the fat-soluble vitamin is selected from the group consisting of vitamin A, D, E, and K.

The present application also includes pharmaceutical kits useful, for example, in the treatment or prevention of diseases which include one or more containers containing a pharmaceutical composition comprising a therapeutically effective amount of maralixibat or a pharmaceutically acceptable salt thereof. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the compounds of the invention, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used intranasally.

EXAMPLES

The following examples are provided to further describe some of the embodiments disclosed herein. The examples are intended to illustrate, not to limit, the disclosed embodiments.

Example 1. Particle Size Evaluation and Milling Study

Trials were conducted to evaluate if jet milling and comilling could provide more consistent particle size results. A design of experiments evaluating the particle size using a lab scale jet mill was conducted. The jet milling experiments were performed using Sturtevant Q2 lab, non-gmp jet mill.

The jet mill design of experiments (DOE) at 5 g scale have 2 factors and 2 levels (4 runs). Feed and grind pressure parameter ranges were 10-30 psi. Responses for the experiment were particle size distribution, and microscopy. Design of experiments for milling study is presented in Table 1.1. Microscopy images of the Active Pharmaceutical Ingredient (API, i.e., maralixibat or its pharmaceutically acceptable salt) before and after jet milling is presented in FIGS. 1-4. A summary of the wet and dry laser particle size results is in Table 1.2.

TABLE 1.1

Design of Experiment- Jet Milling

| Experiment | Grind Pressure (psi) | Feed Pressure (psi) | Initial weight (g) | Final weight (g) | Time to finish (mins) |
|---|---|---|---|---|---|
| 1 | 10 | 10 | 5.09 | 3.40 | 46 |
| 2 | 10 | 30 | 5.10 | 3.24 | 41 |
| 3 | 30 | 10 | Material backup. Not viable. | | |
| 4 | 30 | 30 | 5.00 | 3.88 | 40 |

TABLE 1.2

Jet Milling DoE, Laser Particle Size Results

| Experiment | Grind Pressure (psi) | Feed Pressure (psi) | Dispersion | X10 (μm) | X50 (μm) | X90 (μm) |
|---|---|---|---|---|---|---|
| Unmilled API | | | Wet Rep 1 | 24.83 | 88.81 | 264.72 |
| | | | Wet Rep 2 | 24.20 | 87.41 | 257.92 |
| | | | Wet Rep 3 | 24.43 | 87.27 | 265.36 |
| | | | Wet Mean | 24.5 | 87.8 | 263 |
| | | | Dry | 14.3 | 42.2 | 104 |
| 1 | 10 | 10 | Wet Rep 1 | 2.09 | 8.37 | 18.23 |
| | | | Wet Rep 2 | 1.73 | 7.02 | 15.61 |
| | | | Wet Rep 3 | 1.56 | 6.17 | 14.74 |
| | | | Wet Mean | 1.79 | 7.19 | 16.2 |
| | | | Dry | 0.59 | 2.63 | 7.06 |
| 2 | 10 | 30 | Wet Rep 1 | 1.46 | 5.72 | 18.39 |
| | | | Wet Rep 2 | 1.41 | 5.34 | 20.42 |
| | | | Wet Rep 3 | 1.37 | 5.06 | 22.32 |
| | | | Wet Mean | 1.41 | 5.37 | 20.4 |
| | | | Dry | 0.51 | 1.56 | 3.42 |
| 4 | 30 | 30 | Wet Rep 1 | 2.02 | 8.53 | 22.15 |
| | | | Wet Rep 2 | N/A | N/A | N/A |
| | | | Wet Rep 3 | N/A | N/A | N/A |
| | | | Wet Mean | 2.02 | 8.53 | 22.2 |
| | | | Dry | 0.48 | 1.43 | 2.99 |
| Scale-up 50 g | 10 | 10 | Wet Rep 1 | 1.74 | 7.24 | 17.79 |
| | | | Wet Rep 2 | 1.69 | 6.99 | 17.21 |
| | | | Wet Rep 3 | 1.69 | 6.99 | 17.53 |
| | | | Wet Mean | 1.71 | 7.07 | 17.5 |
| | | | Dry | 1.36 | 4.95 | 13.1 |
| Co-Mill Sample 1 Screen | — | — | Wet Rep 1 | 19.31 | 59.78 | 167.94 |
| | | | Wet Rep 2 | 19.10 | 59.37 | 166.40 |
| | | | Wet Rep 3 | 19.13 | 59.25 | 166.19 |
| | | | Wet Mean | 19.2 | 59.5 | 167 |
| | | | Dry | 13.1 | 35.7 | 76.2 |

The particle size results confirmed that micronization of the API was achieved across the range of feed and grind pressures used.

Figure 5:
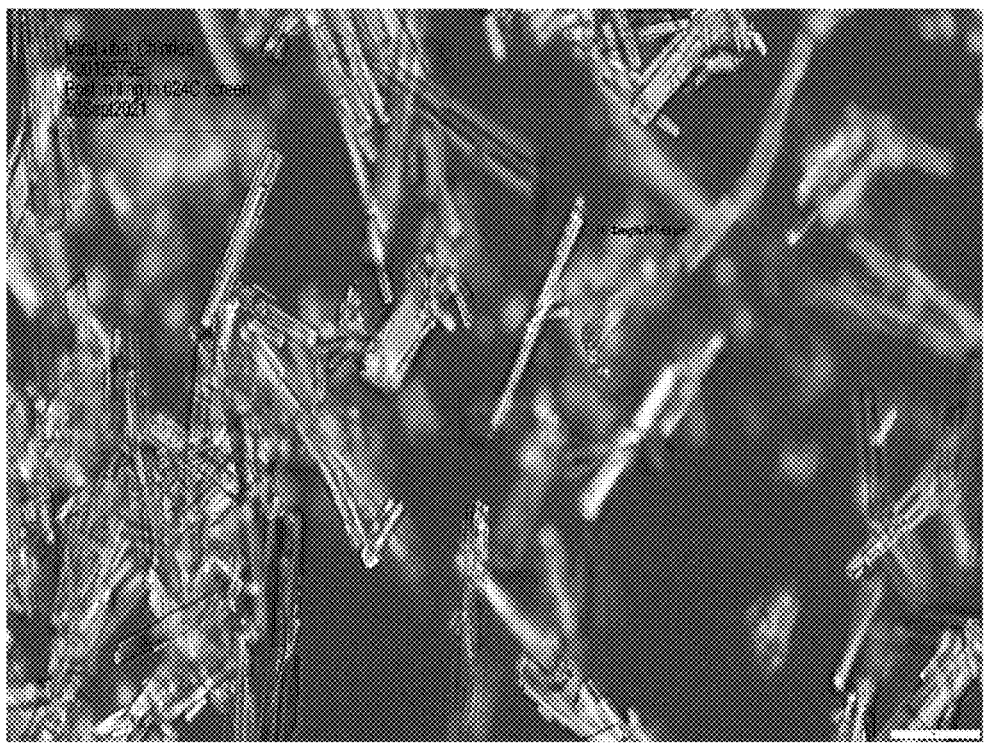
FIG. 5 shows maralixibat chloride post comilling in Sample 3 (640 μm) screen.
Figure 6:
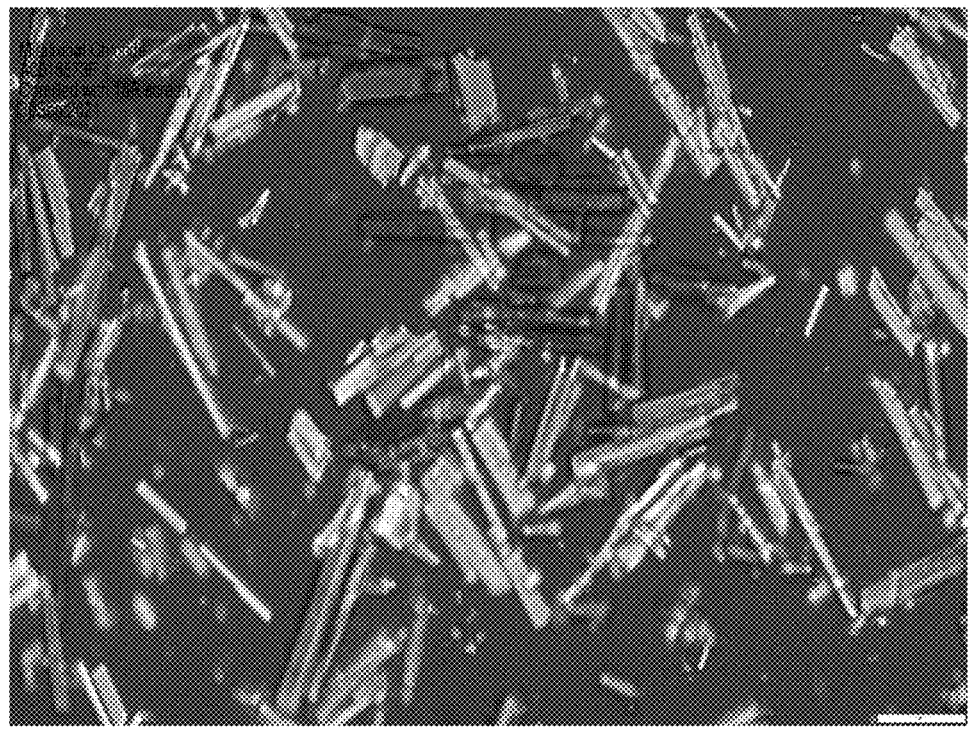
FIG. 6 shows maralixibat chloride post comilling in Sample 2 (457 μm) screen.
Figure 7:
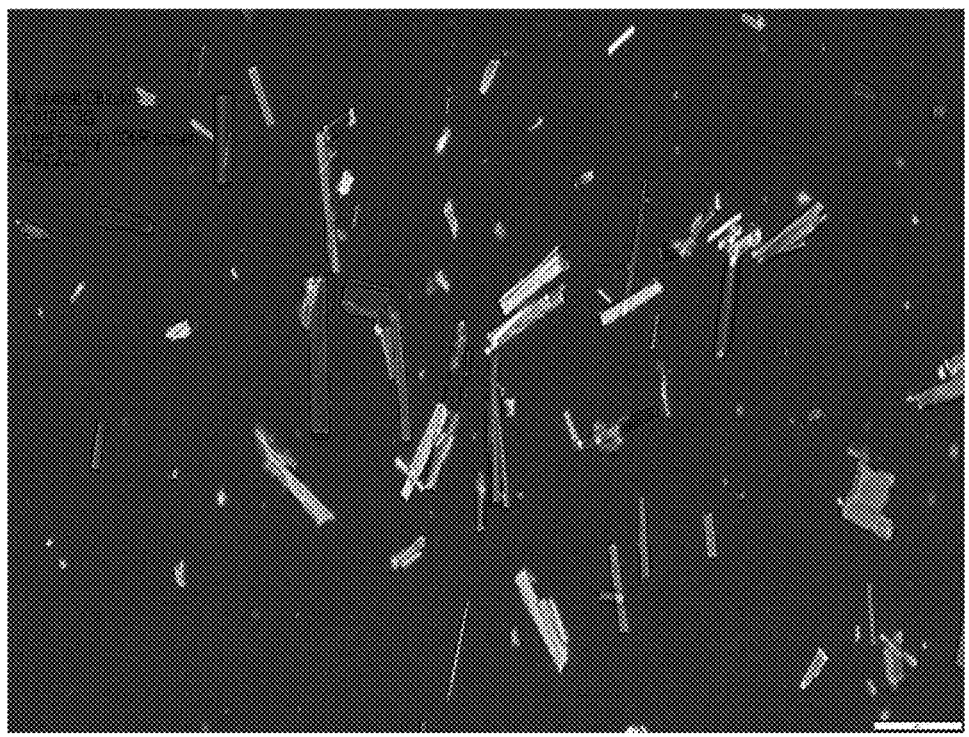
FIG. 7 shows maralixibat chloride post comilling in Sample 1 (229 μm) screen.

The samples were reduced to a micronized size. Next, comilling was evaluated using a range of mill screens in Sample 1 (229 μm), Sample 2 (457 μm), Sample 3 (640 μm), and Sample 4 (813 μm). Microscopy of the feasibility study by comilling is shown in FIGS. 5-7.

Figure 8:
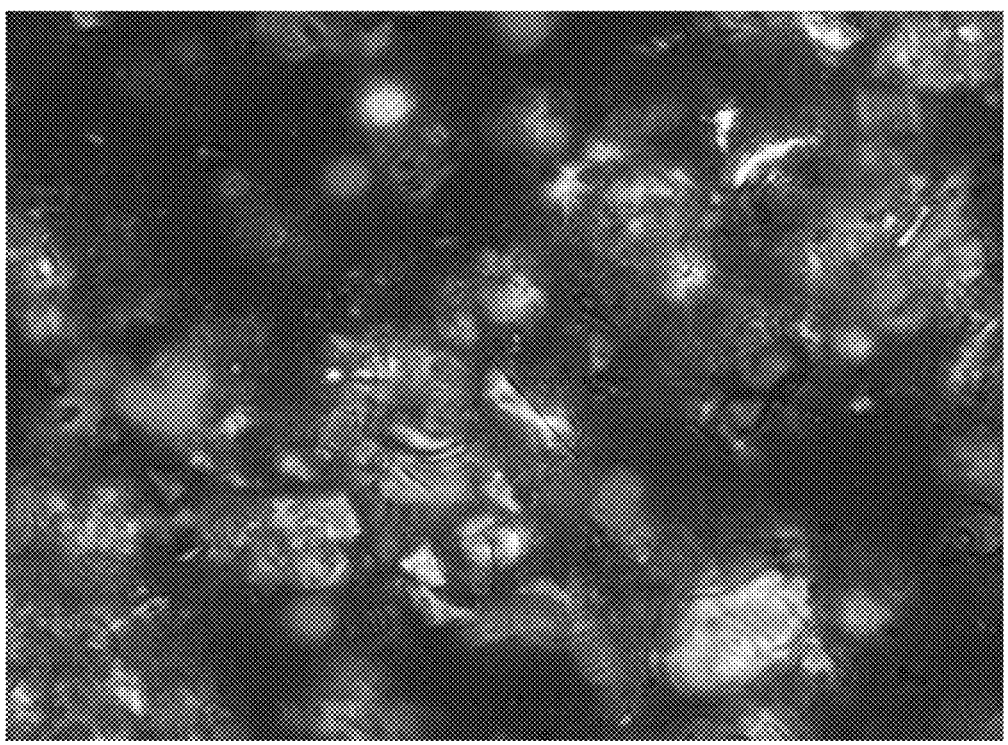
FIG. 8 shows maralixibat chloride API after jet milling 50 g at a feed pressure of 10 psi and a grind pressure of 10 psi.

For the Sample 2 and Sample 3 mill screens, no blinding was observed during milling and little to no change in particle size was observed by microscopy. For the Sample 1 screen, the milling was slow, but no blinding or melting of material was observed. Following these results, the jet mill was used to mill 50 g of drug substance with a setting of 10 psi for the feed and grind pressures. This experiment took approximately 5 hrs to complete milling with yield of 46 g (92%). Microscopy image is presented in FIG. 8.

Example 2. Formulation Development

A direct compression (DC) formulation was produced using MCC and lactose monohydrate, as the primary compaction aids/diluents. A formulation of 25% drug loading was made. A 25 g batch was prepared using the jet milled API. Composition of the formulation is shown in Table 2.1 (Formulation 1). Compression of the batch utilized tooling size of 3/16" round. During the run, the formulation had a sticking problem. Compression was stopped and to resolve the sticking problem, 0.25% more lubricant was added to the remaining formulation. Tablets were still sticking when compressed and high weight variation was also observed. At this point, the remaining material quantity was low, and a new formulation (Formulation 2, Table 2.2) was prepared with the lubricant adjusted to 1.0% magnesium stearate. This formulation was evaluated as a roller compaction granulation.

Figure 9:
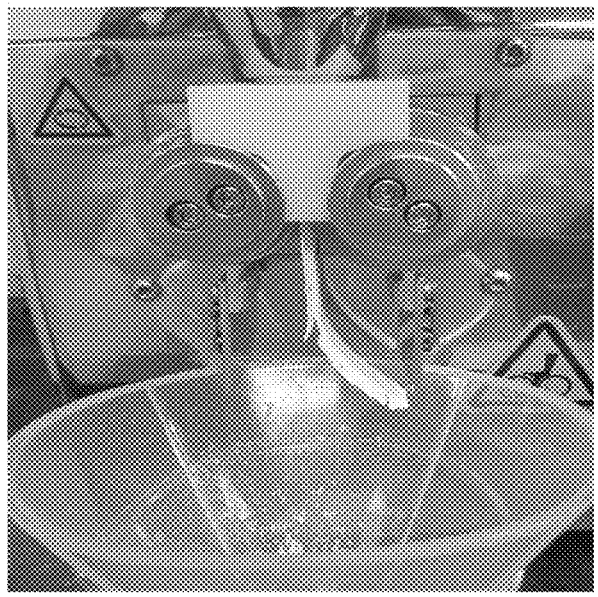
FIG. 9 shows a photo of Formulation 2 compacted blend via roller compaction granulation.

Roller compaction was selected to densify the formulation and to potentially resolve the weight variation issue. Table 2.3 exhibits the roller compaction parameters used. Qualitatively good, continuous ribbons were achieved during the compaction using laddered rollers without sticking issues. A granulation photo is shown in FIG. 9.

TABLE 2.1

Formulation 1

| Components Formulation 1 | %/tab | Mg/tab |
|---|---|---|
| MRX API (jet milled) | 25.00 | 12.50 |
| MCC | 32.00 | 16.00 |
| Lactose monohydrate | 37.00 | 18.50 |
| Croscarmellose Sodium | 5.00 | 2.50 |
| Silicon Dioxide | 0.50 | 0.25 |
| Mag. Stearate | 0.50 | 0.25 |
| Total | 100.00 | 50.00 |

TABLE 2.2

Formulation 2

| Components Formulation 2 | %/tab | Mg/tab |
|---|---|---|
| MRX API (jet milled) | 25.00 | 12.50 |
| MCC | 31.50 | 15.75 |
| Lactose monohydrate | 37.00 | 18.50 |
| Croscarmellose Sodium | 5.00 | 2.50 |
| Silicon Dioxide | 0.50 | 0.25 |
| Mag. Stearate | 1.00 | 0.50 |
| Total | 100.00 | 50.00 |

TABLE 2.3

Roller Compaction Parameters, Formulation 2

| Parameter | Value |
|---|---|
| Roll Type | Laddered/laddered |
| Roll Speed (rpm) | 0.8 |
| Roll Pressure (psi) | 800 |
| Screw Control (rpm) | 11.8 |

Figure 10:
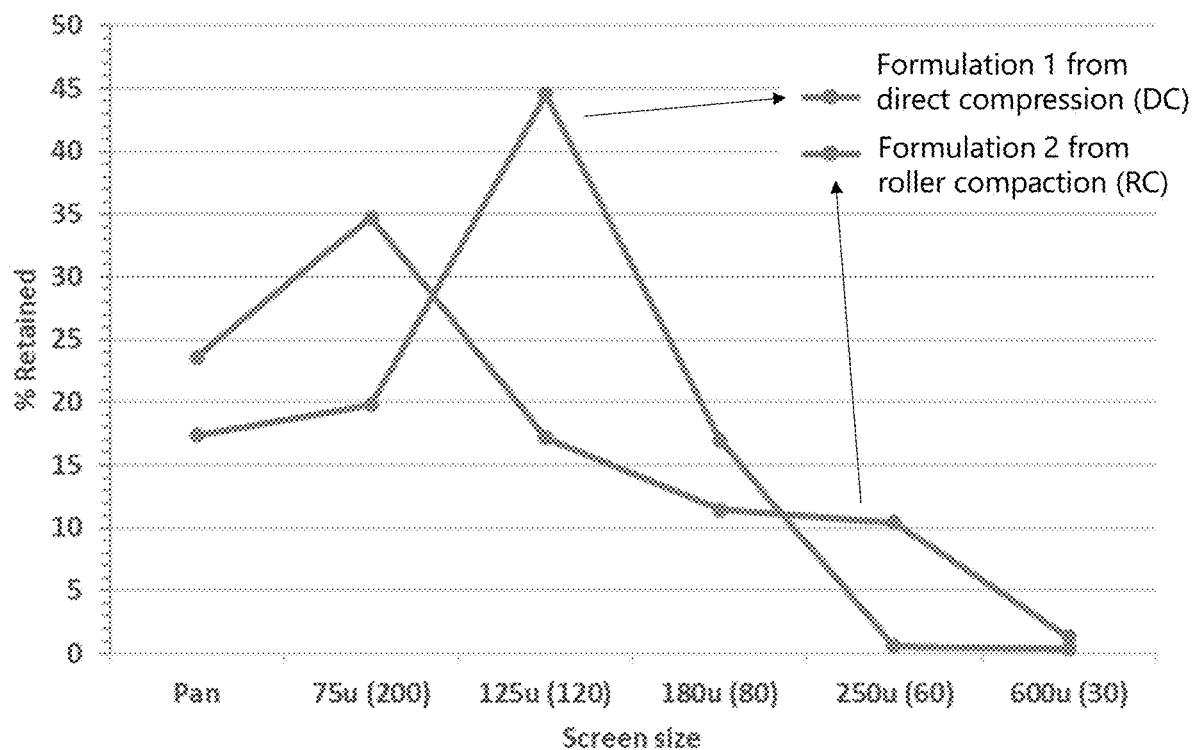
FIG. 10 shows the comparison of the particle size distribution of Formulation 1 from direct compression (DC) vs. Formulation 2 from roller compaction (RC).
Figure 11:
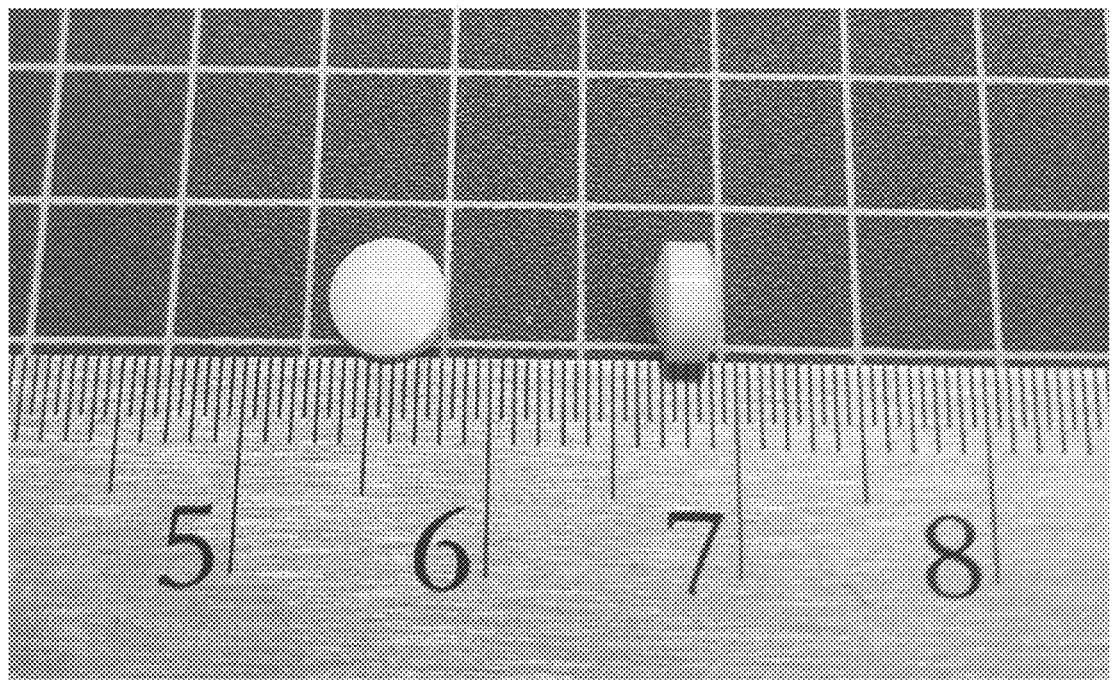
FIG. 11 shows a photo of the compressed tablet of Formulation 2.

After compaction, ribbons were comilled using a screen at 2200 rpm with a round impeller. Bulk and tap density were tested as follows: Bulk density: 0.50 g/mL; tap density: 0.78 g/mL; compressibility index: 36.0 and Hausner ratio is 1.56. Comparison of the particle size distribution of Formulation 1 from DC and Formulation 2 from RC is shown in FIG. 10. Bulk and tap density summary of unmilled API, milled API, DC blend (Formulation 1), and RC granulation (Formulation 2) is presented in Table 2.4. Roller compacted blend was compressed into tablets with no sticking or weight variation issues. Table 2.5 includes a summary of the compression results (Formulation 2). Photo of the tablet is shown in FIG. 11.

TABLE 2.4

Bulk/tap density summary results

| Test | API - unmilled | API - jet milled | DC Blend (Formulation 1) | RC Granulation (Formulation 2) |
|---|---|---|---|---|
| Bulk density (g/mL) | 0.15 | 0.24 | 0.40 | 0.50 |
| Tap density (g/mL) | 0.31 | 0.42 | 0.65 | 0.78 |
| Hausner Ratio | 1.48 | 1.75 | 1.61 | 1.56 |

TABLE 2.5

Compression Results, Formulation 2

| Test | Result |
|---|---|
| Avg Mass (mg) | 51.0 |
| Mass RSD (%) | 0.99% |
| Avg Hardness (kp) | 5.0 |
| Friability (% Loss) | 0.06% |
| Disintegration (s) | 145 |

At this stage, milling studies were undertaken to control the incoming drug substance particle size. Maralixibat DS underwent milling. Loop milled samples of the drug substance were used for the tablet formulation development, 5 mg and 50 mg. The various trial material runs were largely of the same particle size distribution and combined into one sample of Maralixibat DS, loop milled, for use in the formulation development activities. A summary of the loop mill samples is included in Table 2.6. XRPD (to estimate crystallinity) and particle size by wet dispersion were performed.

TABLE 2.6

Maralixibat Chloride (Micronized) Loop Mill Samples

| Micron Run | Feed Rate | Feed Pressure | Mill Pressure | XRD (%) | Wet X10 (µm) | Wet X50 (µm) | Wet X90 (µm) |
|---|---|---|---|---|---|---|---|
| #1 | 576 | 15 | 15 | 95.2 | 9.82 | 41.7 | 107 |
| #2 | 576 | 20 | 20 | 95.3 | 5.47 | 29.7 | 72.5 |
| #3 | 576 | 20 | 20 | 95.1 | 6.31 | 33.7 | 83.8 |
| #4 | 564 | 20 | 20 | 97.4 | 8.24 | 38.1 | 94.0 |
| #5 | 564 | 20 | 20 | 95.5 | 8.82 | 39.5 | 96.6 |

Drug loading of 10% of maralixibat chloride (loop milled) together with excipients such as lactose monohydrate FF316, MCC, croscarmellose sodium, silicon dioxide and magnesium stearate was made. The batch was compressed using ³⁄₁₆" standard round concave (SRC) tooling for 5 mg and modified capsule 6.75 mm×16.00 mm for 50 mg dose. This formulation (Formulation 3) is presented in Table 2.7. A 600 g batch was prepared for Formulation 3.

TABLE 2.7

Direct Compression Formulation, Formulation 3

| Component | Grade/Vendor | %/tab | 5 mg (mg/tab) | 50 mg (mg/tab) |
|---|---|---|---|---|
| MRX salt (Loop milled) | n/a | 10.52 | 5.26 | 52.60 |
| Lactose Monohydrate | FastFlo 316, Kerry/Sheffield | 59.48 | 29.74 | 297.40 |
| MCC | Avicel ® PH302, Dupont | 24.00 | 12.00 | 120.00 |
| Croscarmellose sodium | Ac-Di-Sol ®, Dupont | 5.00 | 2.50 | 25.00 |
| Silicon dioxide | Cab-O-Sil ® M5P, Cabot | 0.50 | 0.25 | 2.50 |
| Mag. Stearate | Spectrum | 0.50 | 0.25 | 2.50 |
| | Total | 100.00 | 50.00 | 500.00 |

Figure 12:
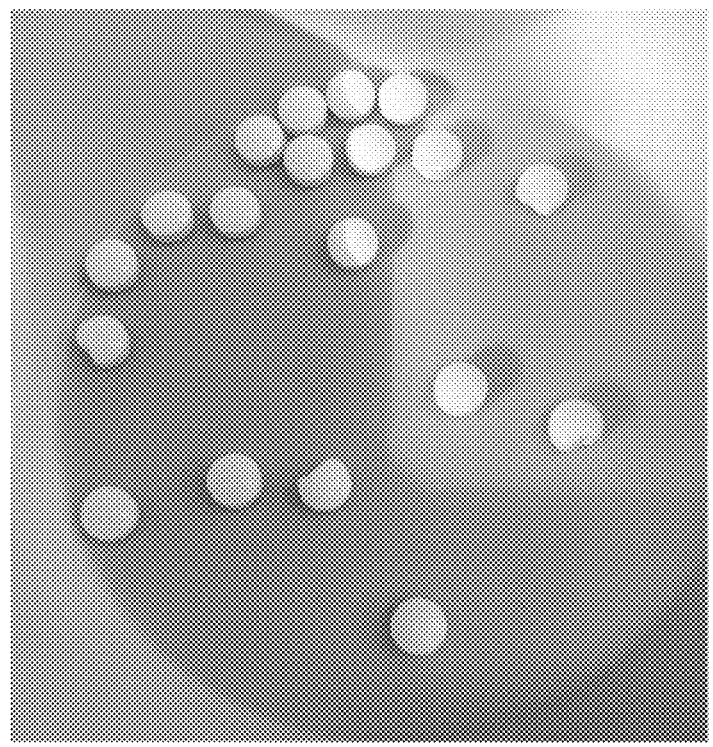
FIG. 12 shows a photo of broken 5 mg dose tablets of Formulation 3.

The initial compression run was performed for the 5 mg dose tablet. Low hardness tablets at ~2 kp were produced. Upon increasing the compression force for the compaction profile, breakage was observed. The tablet breakage stopped upon returning to the lower hardness. Compression profile of 5 mg dose of Formulation 3 is presented in Table 2.8. Photo of breakage tablets is shown in FIG. 12.

TABLE 2.8

Compression Profile 5 mg Dose, Formulation 3

| Parameter | Run 1 | Run 2 | Run 3 | Run 4 |
|---|---|---|---|---|
| Compression Force (kN) | 1.5 | 2.1 | 1.1 | 1.7 |
| Avg Mass (mg) | 50.64 | 47.48 | 50.10 | 50.27 |
| Mass RSD (%) | 0.94 | 2.07 | 0.98 | 1.44 |
| Avg Hardness (kp) | 2.2 | 3.7 | 1.8 | 2.9 |

Figure 13:
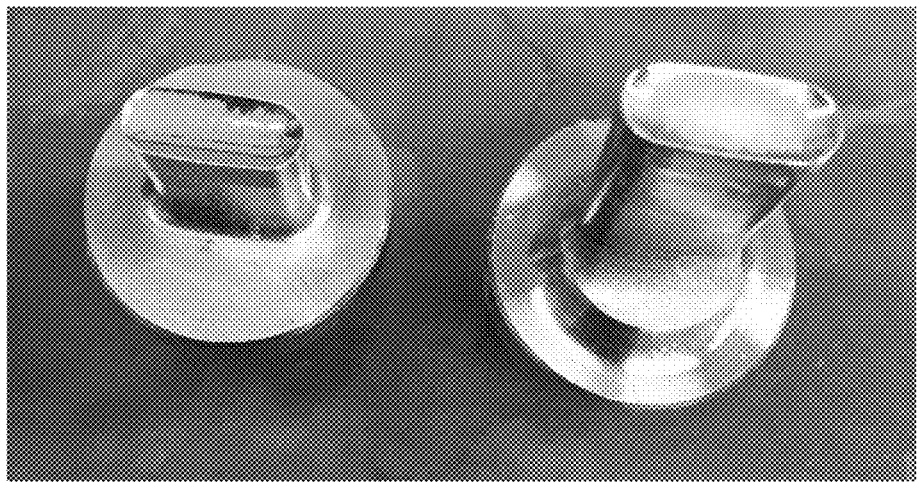
FIG. 13 shows a photo of sticking 50 mg dose tablet of Formulation 3.

Two runs of the 50 mg tablets were produced at high and low force. Approximately 50 tablets per force were produced. No issues with breakage were seen, but the tablet faces were observed to be very dull. The tablet tooling was removed and found to have severe sticking. Tablet breakage on the 5 mg was determined to be sticking related. The compression profile of 50 mg dose of Formulation 3 is presented in Table 2.9 and photo of tablet punches is shown in FIG. 13.

TABLE 2.9

Compression Profile for 50 mg Dose, Formulation 3

| Parameter | Run 1 | Run 2 |
|---|---|---|
| Compression Force (kN) | 6 | 14.8 |
| Avg Mass (mg) | 502.79 | 498.35 |

TABLE 2.9-continued

Compression Profile for 50 mg Dose, Formulation 3

| Parameter | Run 1 | Run 2 |
|---|---|---|
| Mass RSD (%) | 0.35 | 0.39 |
| Avg Hardness (kp) | 7.1 | 19.9 |

Modification of the formulation was needed to eliminate the sticking and breakage issues. The remaining Formulation 3 was used and added 0.50 additional lubricant for a total of 1% magnesium stearate (Formulation 4, Table 2.10). The compression profiles were reattempted for 5 mg and 50 mg tablets using the same tooling. No breakage or sticking was observed across all runs. Tablet weight variability was low indicating good flow in the press. Friability was also low across compression ranges and the disintegration test was fast. Lower disintegration levels were proposed for later trials. The compression profile is presented in Table 2.11.

TABLE 2.10

Formulation 4

| Component | Grade/Vendor | %/tab | 5 mg (mg/tab) | 50 mg (mg/tab) |
|---|---|---|---|---|
| MRX salt (Loop milled) | n/a | 10.48 | 5.24 | 52.39 |
| Lactose Monohydrate | FastFlo 316, Kerry/Sheffield | 59.17 | 29.59 | 295.87 |
| MCC | Avicel ® PH302, Dupont | 23.88 | 11.94 | 119.40 |
| Croscarmellose sodium | Ac-Di-Sol ®, Dupont | 4.98 | 2.49 | 24.88 |
| Silicon dioxide | Cab-O-Sil ® M5P, Cabot | 0.50 | 0.25 | 2.49 |
| Mag. Stearate | Spectrum | 1.00 | 0.50 | 5.00 |
| | Total | 100.00 | 50.00 | 500.00 |

TABLE 2.11

Compression profile, Formulation 4

| | 50 mg | | | 5 mg | | |
|---|---|---|---|---|---|---|
| Parameter | Run1 | Run2 | Run3 | Run4 | Run5 | Run6 |
| Force (kN) | 8.2 | 11.7 | 15.3 | 1.4 | 1.7 | 2.3 |
| Avg Mass (mg) | 509.15 | 507.12 | 503.31 | 50.32 | 50.49 | 50.92 |
| Mass RSD (%) | 0.42% | 0.41% | 0.47% | 0.89% | 0.65% | 0.41% |
| Avg Hardness (kp) | 10.6 | 15.9 | 20.3 | 1.9 | 2.6 | 4.1 |

TABLE 2.11-continued

Compression profile, Formulation 4

|  | 50 mg | | | 5 mg | | |
|---|---|---|---|---|---|---|
| Parameter | Run1 | Run2 | Run3 | Run4 | Run5 | Run6 |
| Friability (%) | 0.32 | 0.22 | 0.13 | 0.25 | 0.22 | 0.14 |
| Disintegration (s) | 40 | 60 | 90 | 3 | 10 | 18 |

Figure 14:
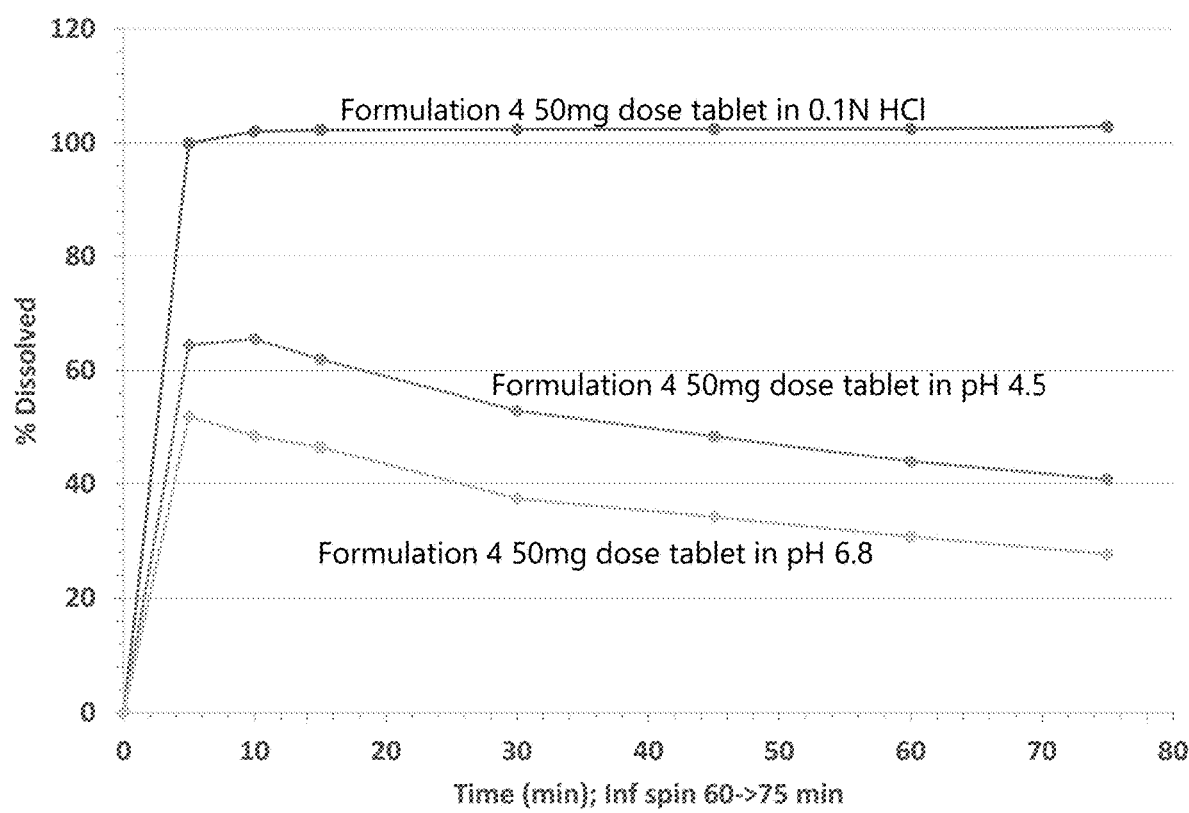
FIG. 14 shows dissolution results of Formulation 4 50 mg dose tablets in various media.

Following a successful compression run, content uniformity was tested on stratified samples collected from Formulation 4 compression (Table 2.12). Dissolution was performed in various media (FIG. 14).

TABLE 2.12

CU (content uniformity) results, 50 mg Tablets, Formulation 4

| Parameter | 50:50:0.05% ACN:Water:TFA (% LC) |
|---|---|
| Tablet 1 | 98.65% |
| Tablet 2 | 99.63% |
| Tablet 3 | 99.63% |
| Tablet 4 | 98.14% |
| Tablet 5 | 100.88% |
| Average | 99.39% |
| % RSD | 1.06% |
| Min | 98.14% |
| Max | 100.88% |

In the dissolution study, tablets were showing full recovery of the 50 mg tablet dose at a lower pH (0.1N HCl) but low recovery at pH 4.5 and 6.8. Solutions were prepared containing Maralixibat and one excipient at the level observed in the tablet. A summary of the results is in Table 2.13 and found that croscarmellose sodium and magnesium stearate may contribute to low recovery in the dissolution test.

TABLE 2.13

Individual Excipient Solubility Study

| Sample | % Recovery |
|---|---|
| Lactose Monohydrate | 86 |
| MCC | 86 |
| Croscarmellose sodium | 53 |
| Silicon dioxide | 83 |
| Magnesium stearate | 57 |

DC Formulation 5 was prepared as shown in Table 2.14. This formulation used the same drug loading at 10%, the amount of MCC was increased, and the amount of lactose FF316 was reduced to see if improved compression performance could be achieved. The same batch size and level of lubricant in the formulation was used.

Initial compression of Formulation 5 was made in 50 mg tablets using the same tooling (15.58 mm×6.63 mm modified capsule). The initial compression run was good, but prolonged compression produced a dull surface of the tablet. The tooling was removed and found to have slight sticking on the lower punch and no sticking on the upper punch. The same modification in the formulation was done for Formulation 5 with the addition of 0.500 lubricant (mag. Stearate) for a total of 1% mag. Stearate (Formulation 6, Table 2.15). The compression profile was then created at 5 mg and 50 mg. No breaking or sticking was observed across these runs. Weight variability was good, also indicates good flow and friability was also low. Compression profile is presented in Table 2.16. Bulk and tap density test were also done to compare Formulation 4 and Formulation 6. Results from both formulations were comparable as presented in Table 2.17.

TABLE 2.14

| | Formulation 5 | | | |
|---|---|---|---|---|
| Component | Grade/Vendor | %/tab | 5 mg (mg/tab) | 50 mg (mg/tab) |
| MRX salt (Loop milled) | n/a | 10.52 | 5.26 | 52.6 |
| Lactose Monohydrate | FastFlo 316, Kerry/Sheffield | 23.48 | 11.74 | 117.40 |
| MCC | Avicel ® PH302, Dupont | 60.00 | 30.00 | 300 |
| Croscarmellose sodium | Ac-Di-Sol ®, Dupont | 5.00 | 2.50 | 25 |
| Silicon dioxide | Cab-O-Sil ® M5P, Cabot | 0.50 | 0.25 | 2.5 |
| Mag. Stearate | Spectrum | 0.50 | 0.25 | 2.5 |
| Total | | 100.00 | 50.00 | 500.00 |

TABLE 2.15

Formulation 6

| Component | Grade/Vendor | %/tab | 5 mg (mg/tab) | 50 mg (mg/tab) |
|---|---|---|---|---|
| MRX salt (Loop milled) | n/a | 10.47 | 5.23 | 52.34 |
| Lactose Monohydrate | FastFlo 316, Kerry/Sheffield | 23.36 | 11.68 | 116.81 |
| MCC | Avicel ® PH302, Dupont | 59.70 | 29.85 | 298.51 |
| Croscarmellose sodium | Ac-Di-Sol ®, Dupont | 4.98 | 2.49 | 24.88 |
| Silicon dioxide | Cab-O-Sil ® M5P, Cabot | 0.50 | 0.25 | 2.49 |
| Mag. Stearate | Spectrum | 1.00 | 0.50 | 4.98 |
| | Total | 100.00 | 50.00 | 500.00 |

TABLE 2.16

Compression Profile of Formulation 6

| | 50 mg | | | 5 mg | | |
|---|---|---|---|---|---|---|
| Parameter | Run1 | Run2 | Run3 | Run4 | Run5 | Run6 |
| Force (kN) | 4.9 | 7.1 | 9.1 | 1.1 | 1.5 | 2.0 |
| Avg Mass (mg) | 499.15 | 500.58 | 502.14 | 49.87 | 49.62 | 49.54 |
| Mass RSD (%) | 0.59% | 0.42% | 0.37% | 0.61 | 0.92 | 0.55 |
| Avg Hardness (kp) | 9.2 | 15.2 | 20.0 | 2.2 | 3.1 | 4.2 |
| Friability (%) | 0.51 | 0.26 | 0.16 | 0.26 | 0.11 | 0.10 |
| Disintegration (s) | 14 secs | 16 secs | 21 secs | <5 secs | 4 secs. | <5 secs |

TABLE 2.17

Bulk and Tap Density Comparison, Formulations 4 & 6

| Test | Formulation 4 | Formulation 6 |
|---|---|---|
| Bulk Density (g/mL) | 0.54 | 0.55 |
| Tap Density (g/mL) | 0.69 | 0.70 |
| Comp Index (%) | 21.84 (passable) | 22.00 (passable) |
| Hausner ratio | 1.28 | 1.28 |

Figure 15:
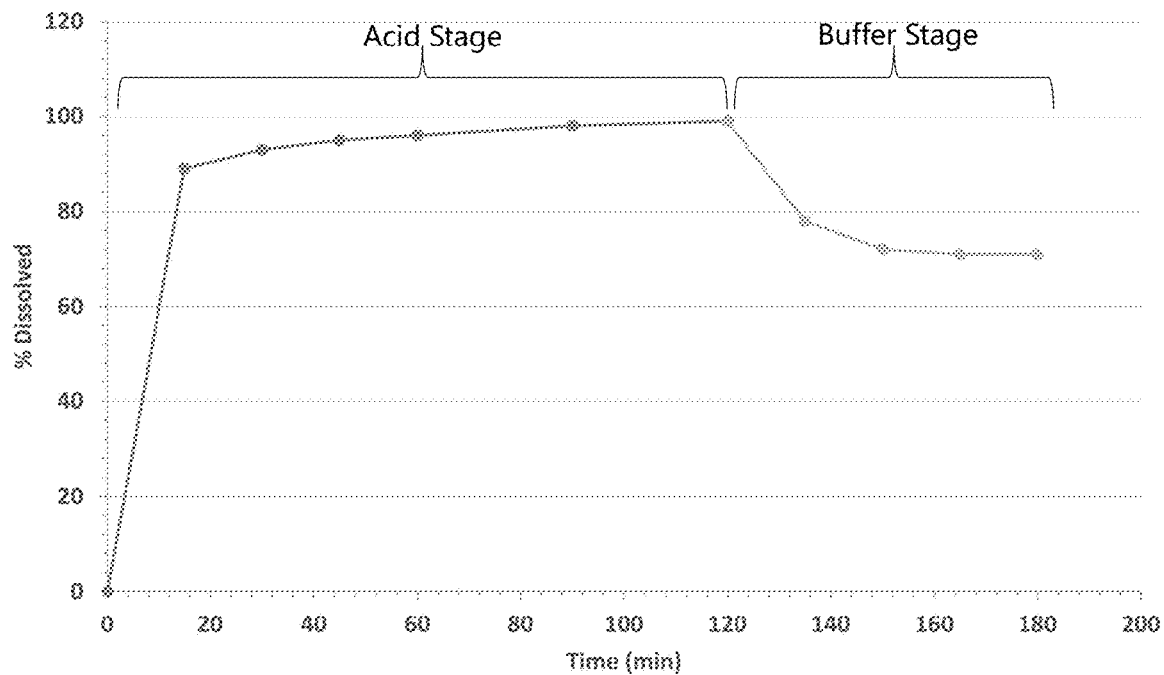
FIG. 15 shows dissolution result plot of a media exchange run with 50 mg dose tablets of Formulation 7.
Figure 16:
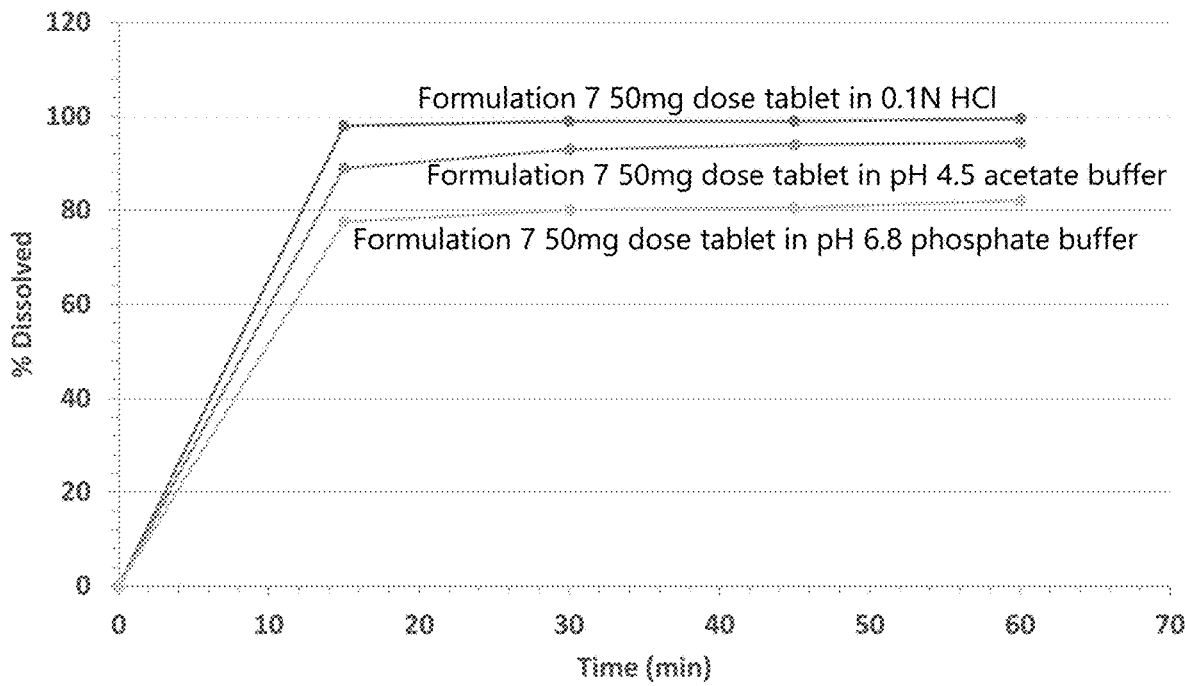
FIG. 16 shows dissolution result plot of 50 mg dose tablets of Formulation 7 in three media.

Formulation 7 was generated by removing croscarmellose sodium and reducing the amount of lubricant to 0.75%. Formulation 7 is presented in Table 2.18. Compression profile is presented in Table 2.19. Dissolution was tested as a media exchange run (FIG. 15, Table 2.20) and in three media (FIG. 16, Table 2.21). The dissolution was performed in 750 mL of 0.1N HCl media for 120 min and then 250 mL of pH 6.8 0.2M phosphate buffer was added and the dissolution continued out to 180 min.

TABLE 2.18

Formulation 7

| Component | Grade/Vendor | %/tab | 5 mg (mg/tab) | 50 mg (mg/tab) |
|---|---|---|---|---|
| MRX salt (Loop milled) | n/a | 10.52 | 5.26 | 52.61 |
| Lactose Monohydrate | FastFlo 316, Kerry/Sheffield | 23.48 | 11.74 | 117.41 |
| MCC | Avicel ® PH302, Dupont | 64.75 | 32.37 | 323.73 |
| Silicon dioxide | Cab-O-Sil ® M5P, Cabot | 0.50 | 0.25 | 2.5 |
| Mag. Stearate | Spectrum | 0.75 | 0.38 | 3.75 |
| | Total | 100.00 | 50.00 | 500.00 |

TABLE 2.19

Formulation 7, Compression Profile

|  | 50 mg | | | 5 mg | | |
| --- | --- | --- | --- | --- | --- | --- |
| Parameter | Run1 | Run2 | Run3 | Run4 | Run5 | Run6 |
| Force (kN) | 5.7 | 8.0 | 10.0 | 0.9 | 1.2 | 1.70 |
| Avg Mass (mg) | 499.63 | 500.78 | 501.03 | 49.76 | 49.79 | 49.95 |
| Mass RSD (%) | 0.59% | 0.10% | 0.76% | 0.78 | 1.00 | 0.73 |
| Avg Hardness (kp) | 11.0 | 16.0 | 20.1 | 2.1 | 2.8 | 4.1 |
| Friability (%) | 0.29 | 0.19 | 0.09 | 0.38 | 0.24 | 0.28 |
| Disintegration (s) | 29 secs | 31 secs | 104 secs | <5 secs | 12 secs | 27 secs |

TABLE 2.20

Dissolution Result Table, 50mg Formulation 7 Tablets

| | Acid Stage | | | | | |
| --- | --- | --- | --- | --- | --- | --- |
| Sample | 15 min | 30 min | 45 min | 60 min | 90 min | 120 min |
| 1 | 86 | 92 | 94 | 96 | 97 | 98 |
| 2 | 88 | 93 | 95 | 96 | 97 | 98 |
| 3 | 85 | 87 | 90 | 92 | 96 | 98 |
| 4 | 93 | 95 | 97 | 98 | 99 | 99 |
| 5 | 89 | 93 | 96 | 97 | 98 | 100 |
| 6 | 95 | 97 | 97 | 99 | 99 | 99 |
| Avg | 89 | 93 | 95 | 96 | 98 | 99 |
| % RSD | 5 | 4 | 3 | 2 | 1 | 1 |

| | Buffer Stage | | | |
| --- | --- | --- | --- | --- |
| Sample | 15 min | 30 min | 45 min | 60 min |
| 1 | 77 | 71 | 70 | 70 |
| 2 | 78 | 72 | 71 | 71 |
| 3 | 78 | 71 | 69 | 71 |
| 4 | 78 | 71 | 71 | 71 |
| 5 | 79 | 73 | 73 | 72 |
| 6 | 80 | 71 | 72 | 71 |
| Avg | 78 | 72 | 71 | 71 |
| % RSD | 1 | 1 | 2 | 1 |

TABLE 2.21

Dissolution Result Table, 50 mg Formulation 7 Tablets

| | 0.1N HCl | | | |
| --- | --- | --- | --- | --- |
| Sample | 15 min | 30 min | 45 min | 60 min |
| 1 | 100 | 100 | 100 | 100 |
| 2 | 96 | 98 | 98 | 99 |
| Avg | 98 | 99 | 99 | 100 |

| | pH 4.5 acetate buffer | | | |
| --- | --- | --- | --- | --- |
| Sample | 15 min | 30 min | 45 min | 60 min |
| 1 | 88 | 92 | 93 | 94 |
| 2 | 90 | 94 | 95 | 95 |
| Avg | 89 | 93 | 94 | 95 |

| | pH 6.8 phosphate buffer | | | |
| --- | --- | --- | --- | --- |
| Sample | 15 min | 30 min | 45 min | 60 min |
| 1 | 77 | 81 | 79 | 82 |
| 2 | 78 | 79 | 82 | 82 |
| Avg | 78 | 80 | 81 | 82 |

Figure 17:
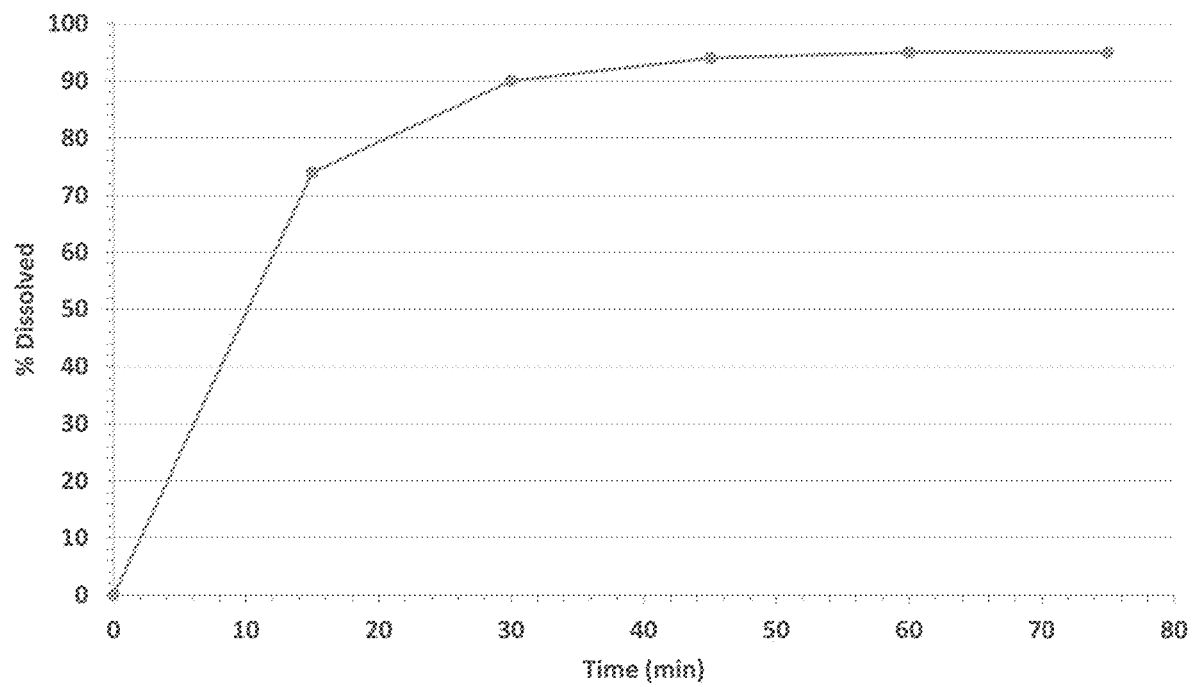
FIG. 17 shows dissolution in pH 6.8 phosphate buffer of 50 mg unmilled maralixibat filled into capsules.

In trend with the previous dissolution results, the acid stage saw complete release of the drug substance, then upon the change to buffer stage, the drug substance came out of solution below 80% release. 50 mg unmilled DS was filled into capsules (opaque, white gelatin) and tested for dissolution in the pH 6.8 phosphate buffer (FIG. 17, Table 2.22).

TABLE 2.22

Drug Substance in Capsule, Dissolution Results

| | Time | | | |
| --- | --- | --- | --- | --- |
| Sample | 15 min | 30 min | 45 min | 60 min |
| 1 | 88 | 92 | 94 | 94 |
| 2 | 79 | 89 | 94 | 94 |
| 3 | 89 | 95 | 95 | 95 |
| 4 | 81 | 88 | 92 | 95 |
| 5 | 90 | 94 | 96 | 96 |
| 6 | 18 | 80 | 92 | 95 |
| Avg | 74 | 90 | 94 | 95 |
| % RSD | 37.7% | 6.1% | 1.7% | 0.8% |

Figure 18:
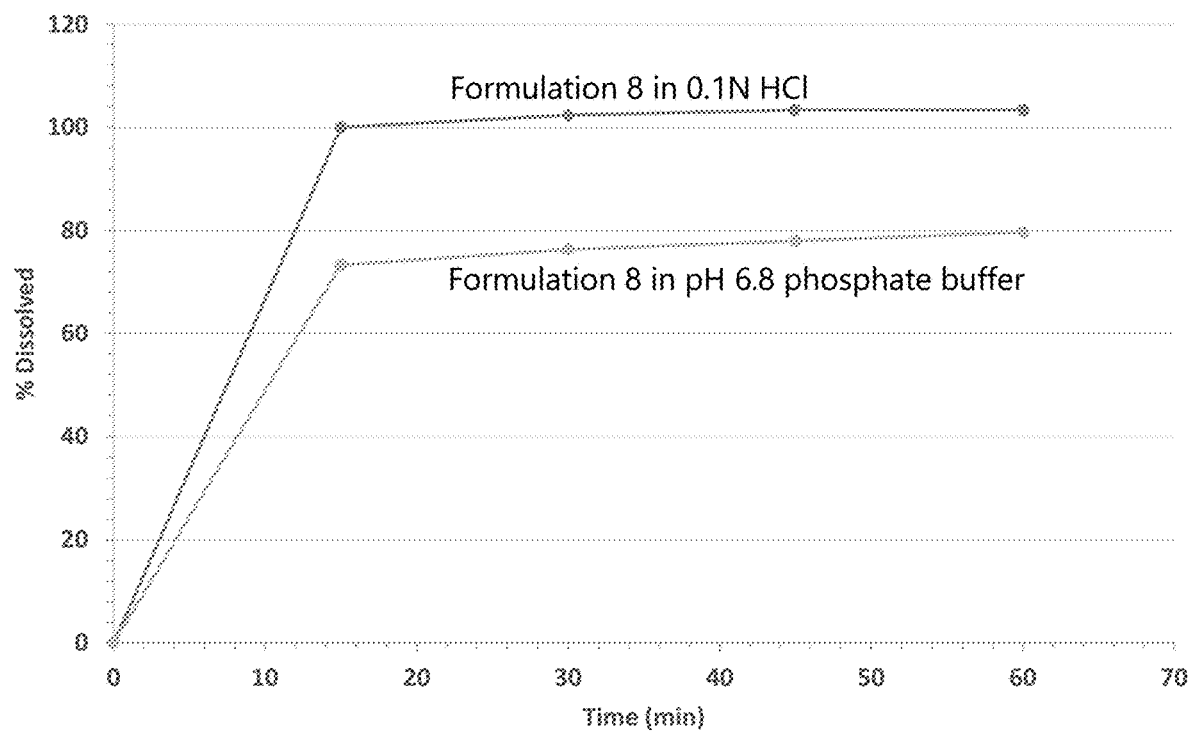
FIG. 18 shows dissolution results of Formulation 8.
Figure 19:
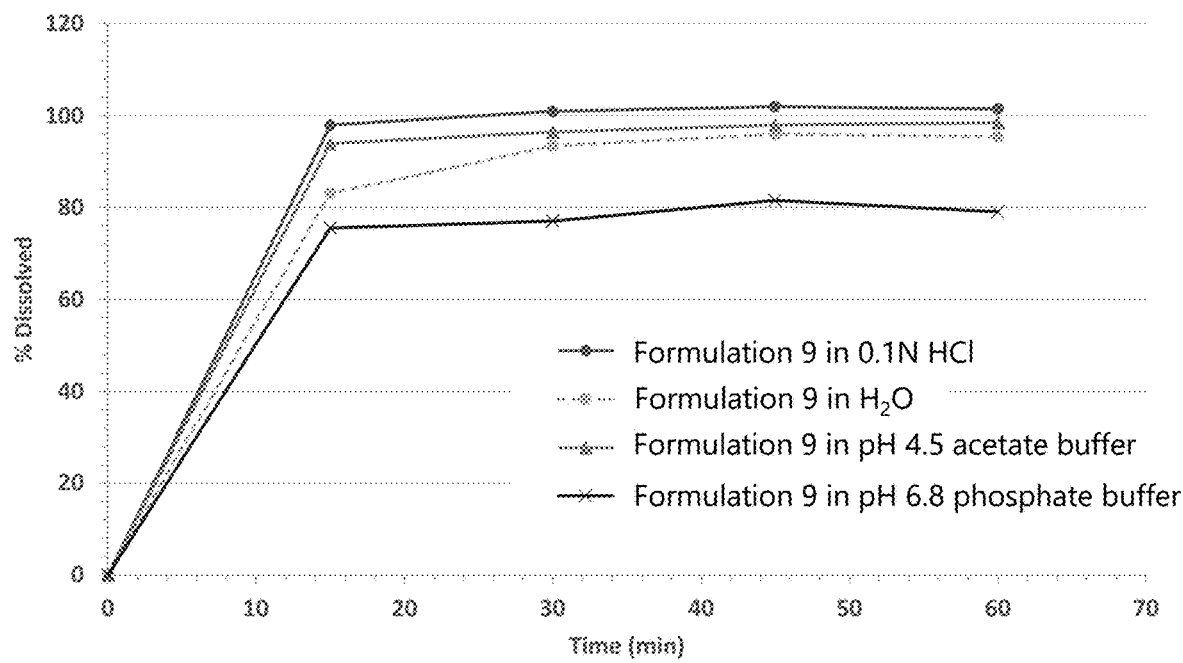
FIG. 19 shows dissolution results of Formulation 9.
Figure 20:
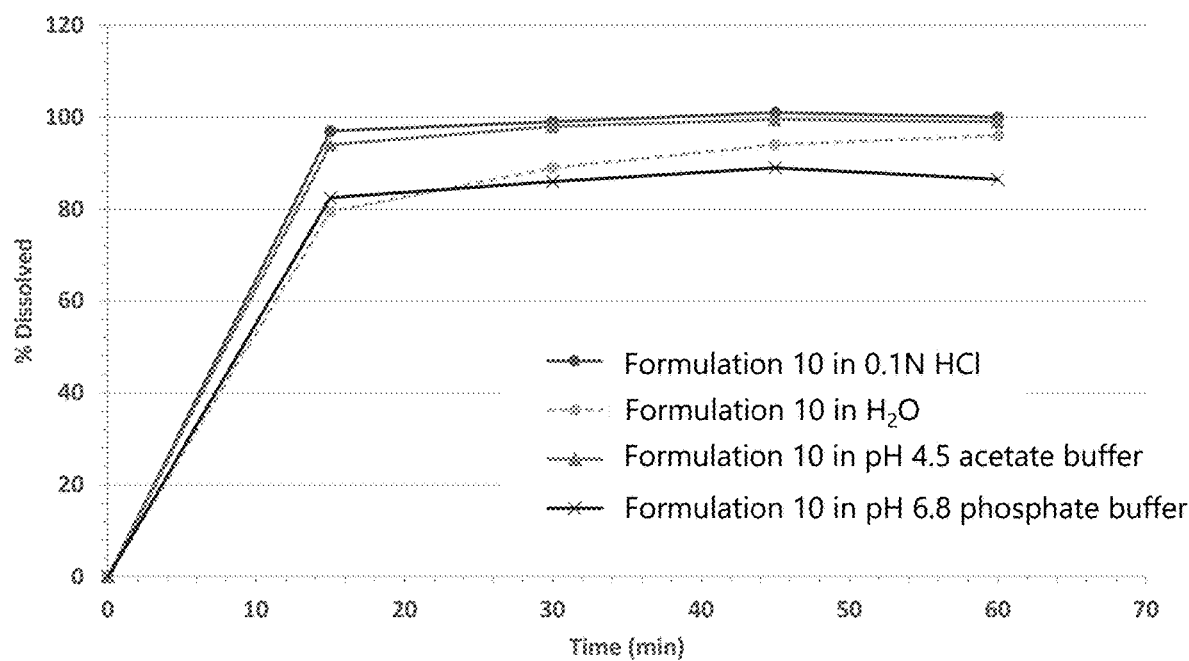
FIG. 20 shows dissolution results of Formulation 10.

Further trials from Formulation 7 were performed to replace magnesium stearate with other lubricants such as sodium stearyl fumarate and stearic acid as presented in Table 2.23. To aid in speed and conserve material, small batches of each formulation trial were produced and hand-filled into capsules for dissolution testing. Formulation 8 was produced by adding EDTA. Formulations 9 and 10 were filled in size 00 gelatin capsules. Dissolution results are shown in FIGS. 18-20 & Tables 2.24, 2.25, and 2.26.

TABLE 2.23

Formulations 8-10

| | Formulation 8 | | Formulation 9 | | Formulation 10 | |
| --- | --- | --- | --- | --- | --- | --- |
| Component | %/tab | 50 mg (mg/tab) | %/caps | 50 mg (mg/cap) | %/caps | 50 mg (mg/cap) |
| Maralixibat salt (Loop milled) | 10.51 | 52.59 | 10.52 | 52.60 | 10.52 | 52.60 |
| Lactose Monohydrate | 23.46 | 117.39 | 23.48 | 117.40 | 23.48 | 117.40 |
| MCC | 64.69 | 323.72 | 64.75 | 323.70 | 64.75 | 323.70 |
| Silicon dioxide | 0.50 | 2.50 | 0.50 | 2.50 | 0.50 | 2.50 |
| Magnesium Stearate | 0.75 | 3.75 | — | — | — | — |
| EDTA | 0.10 | 0.50 | — | — | — | — |
| Sodium stearyl fumarate | — | — | 0.75 | 3.75 | — | — |
| Stearic acid | — | — | — | — | 0.75 | 3.75 |
| total | 100.00 | 500.45 | 100.00 | 499.95 | 100.00 | 499.95 |

TABLE 2.24

Formulation 8, Dissolution Results

| | 0.1N | | | |
| --- | --- | --- | --- | --- |
| Sample | 15 min | 30 min | 45 min | 60 min |
| 1 | 101 | 104 | 104 | 104 |
| 2 | 96 | 99 | 101 | 101 |
| 3 | 103 | 104 | 105 | 105 |
| Avg | 100 | 102 | 103 | 103 |
| % RSD | 3.6% | 2.8% | 2.0% | 2.0% |

TABLE 2.24-continued

Formulation 8, Dissolution Results pH 6.8 phosphate buffer

| Sample | 15 min | 30 min | 45 min | 60 min |
|---|---|---|---|---|
| 1 | 71 | 77 | 78 | 80 |
| 2 | 75 | 76 | 78 | 79 |
| 3 | 74 | 76 | 78 | 80 |
| Avg | 73 | 76 | 78 | 80 |
| % RSD | 2.8% | 0.8% | 0.0% | 0.7% |

TABLE 2.25

Formulation 9, Dissolution Results 0.1N

| Sample | 15 min | 30 min | 45 min | 60 min |
|---|---|---|---|---|
| 1 | 97 | 101 | 102 | 101 |
| 2 | 99 | 101 | 102 | 102 |
| Avg | 98 | 101 | 102 | 102 |

Water

| Sample | 15 min | 30 min | 45 min | 60 min |
|---|---|---|---|---|
| 1 | 86 | 95 | 98 | 97 |
| 2 | 80 | 92 | 94 | 94 |
| Avg | 83 | 94 | 96 | 96 | pH 4.5 acetate buffer

| Sample | 15 min | 30 min | 45 min | 60 min |
|---|---|---|---|---|
| 1 | 93 | 96 | 98 | 98 |
| 2 | 95 | 97 | 98 | 99 |
| Avg | 94 | 97 | 98 | 99 | pH 6.8 phosphate buffer

| Sample | 15 min | 30 min | 45 min | 60 min |
|---|---|---|---|---|
| 1 | 76 | 77 | 80 | 78 |
| 2 | 75 | 77 | 83 | 80 |
| Avg | 76 | 77 | 82 | 79 |

TABLE 2.26

Formulation 10, Dissolution Results 0.1N

| Sample | 15 min | 30 min | 45 min | 60 min |
|---|---|---|---|---|
| 1 | 98 | 99 | 101 | 100 |
| 2 | 96 | 99 | 101 | 100 |
| Avg | 97 | 99 | 101 | 100 |

Water

| Sample | 15 min | 30 min | 45 min | 60 min |
|---|---|---|---|---|
| 1 | 77 | 86 | 93 | 96 |
| 2 | 82 | 92 | 95 | 96 |
| Avg | 80 | 89 | 94 | 96 |

TABLE 2.26-continued

Formulation 10, Dissolution Results pH 4.5 acetate buffer

| Sample | 15 min | 30 min | 45 min | 60 min |
|---|---|---|---|---|
| 1 | 92 | 96 | 97 | 97 |
| 2 | 96 | 100 | 102 | 101 |
| Avg | 94 | 98 | 100 | 99 | pH 6.8 phosphate buffer

| Sample | 15 min | 30 min | 45 min | 60 min |
|---|---|---|---|---|
| 1 | 79 | 81 | 86 | 83 |
| 2 | 86 | 91 | 92 | 90 |
| Avg | 83 | 86 | 89 | 87 |

Figure 21:
FIG. 21 shows a photo of 5 mg dose tablets of Formulation 11.
Figure 22:
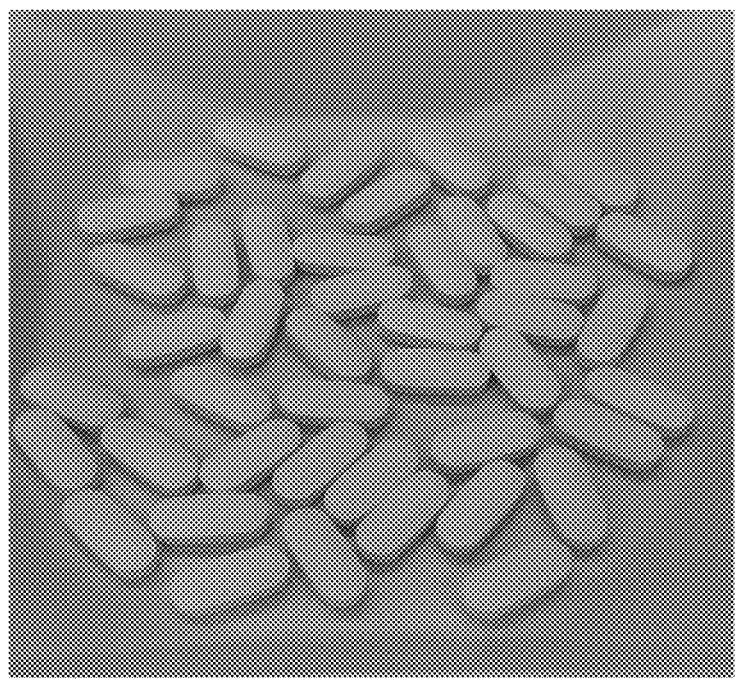
FIG. 22 shows a photo of 50 mg dose tablets of Formulation 11.

Following another round of dissolution testing, the stearic acid formulation was selected to proceed with further testing. Formulation 11 was prepared without croscarmellose sodium and with stearic acid as lubricant at 1.00 level. A 600 g batch size was prepared to check if sticking will be observed during compression run. Formulation and compression profile is presented in Table 2.27 and 2.28, respectively. Density test is shown in Table 2.29. Qualitatively, no breaking or sticking was observed across the runs. Tablet weight variability was low, as shown in Table 2.28, indicating good flow, as shown in Table 2.29, and friability is also low across compression runs. Photo of tablets for 5 mg and 50 mg is shown in FIGS. 21-22.

TABLE 2.27

Formulation 11

| Component | Grade/Vendor | %/tab | 5 mg (mg/tab) | 50 mg (mg/tab) |
|---|---|---|---|---|
| MRX salt (Loop milled) | n/a | 10.52 | 5.26 | 52.60 |
| Lactose Monohydrate | FastFlo 316, Kerry/Sheffield | 23.48 | 11.74 | 117.40 |
| MCC | Avicel ® PH302, Dupont | 64.50 | 32.25 | 322.50 |
| Silicon dioxide | Cab-O-Sil ® M5P, Cabot | 0.50 | 0.25 | 2.50 |
| Stearic acid | Spectrum | 1.00 | 0.50 | 5.00 |
| Total | | 100.00 | 50.00 | 500.00 |

TABLE 2.28

Formulation 11 Compression profile

| | 50 mg | | | 5 mg | | |
|---|---|---|---|---|---|---|
| Parameter | Run1 | Run2 | Run3 | Run4 | Run5 | Run6 |
| Force (kN) | 6.3 | 8.6 | 11.6 | 1.1 | 1.5 | 2.2 |
| Avg Mass (mg) | 488.59 | 500.20 | 496.07 | 50.09 | 49.94 | 49.88 |
| Mass RSD (%) | 0.60 | 0.42 | 0.30 | 0.63 | 1.00 | 0.57 |
| Avg Hardness (kp) | 11.0 | 16.1 | 19.9 | 2.2 | 3.3 | 4.8 |
| Friability (%) | 0.39 | 0.20 | 0.16 | 0.43 | 0.31 | 0.15 |
| Disintegration (s) | 40 secs | 53 secs | 275 secs | <5 secs | 15 secs | 148 secs |

TABLE 2.29

| Formulation 11 Density test | |
|---|---|
| Test | Formulation 11 |
| Bulk Density (g/mL) | 0.53 |
| Tap Density (g/mL) | 1.45 |
| Comp Index (%) | 24.00 |
| Hausner ratio | 1.32 (passable) |

Figure 23:
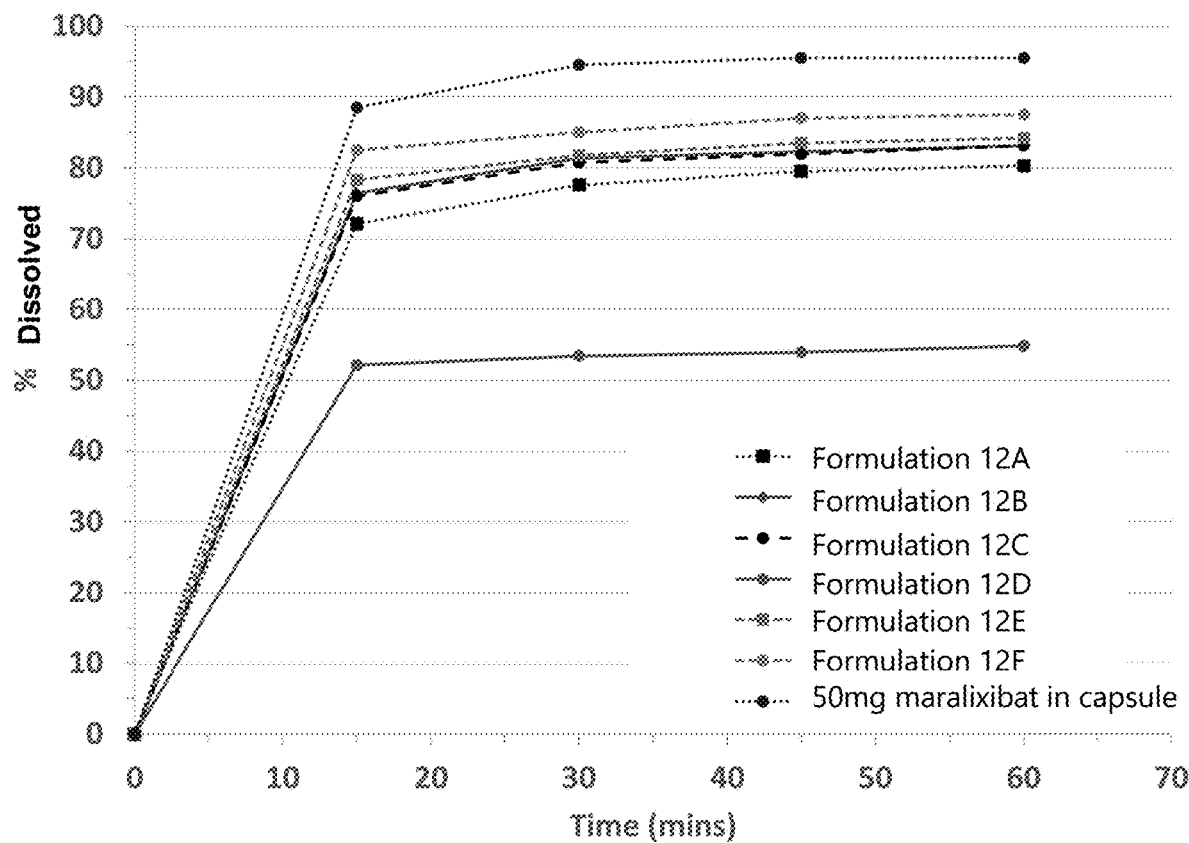
FIG. 23 shows the 50 mg capsule dissolution results of Formulations 12A-12F.

Alternative, water-soluble lubricants were evaluated for a dissolution study in pH 6.8 phosphate buffer. A common batch of the 50 mg (Formulation 11) was prepared up to the glidant, and then the different lubricants or excipients were added at 30 level (Formulations 12A-F) to smaller sub-samples. Each formulation was filled in size 00 gelatin capsules at 500 mg formulation/capsules and were tested. The formulations with these different lubricants are presented in Table 2.30 and Table 2.31. Dissolution results in pH 6.8 phosphate buffer are in FIG. 23 and Table 2.32.

TABLE 2.30

| | Formulations 12A-12F (%/cap) | | | | | |
|---|---|---|---|---|---|---|
| Component | Formulation 12A | Formulation 12B | Formulation 12C | Formulation 12D | Formulation 12E | Formulation 12F |
| [[MXT]]MRX salt loop milled | 10.52% | 10.52% | 10.52% | 10.52% | 10.52% | 10.52% |
| Lactose Monohydrate | 23.48% | 23.48% | 23.48% | 23.48% | 23.48% | 23.48% |
| MCC | 62.50% | 62.50% | 62.50% | 62.50% | 62.50% | 62.50% |
| Silicon Dioxide | 0.50% | 0.50% | 0.50% | 0.50% | 0.50% | 0.50% |
| Hydrogenated Cottonseed Oil | 3.00% | — | — | — | — | — |
| Glyceryl dibehenate | — | 3.00% | — | — | — | — |
| Glyceryl Palmitostearate | — | — | 3.00% | — | — | — |
| Sodium lauryl sulfate | — | — | — | 3.00% | — | — |
| Poloxamer 188 | — | — | — | — | 3.00% | — |
| PEG 8000 | — | — | — | — | — | 3.00% |
| total | 100.00% | 100.00% | 100.00% | 100.00% | 100.00% | 100.00% |

TABLE 2.31

| | Formulations 12A-12F (mg/cap) | | | | | |
|---|---|---|---|---|---|---|
| Component | Formulation 12A | Formulation 12B | Formulation 12C | Formulation 12D | Formulation 12E | Formulation 12F |
| [[MXT]]MRX salt loop milled | 52.60 | 52.60 | 52.60 | 52.60 | 52.60 | 52.60 |
| Lactose Monohydrate | 117.40 | 117.40 | 117.40 | 117.40 | 117.40 | 117.40 |
| MCC | 312.50 | 312.50 | 312.50 | 312.50 | 312.50 | 312.50 |
| Silicon Dioxide | 2.5 | 2.5 | 2.5 | 2.5 | 2.5 | 2.5 |
| Hydrogenated Cottonseed Oil | 15.00 | — | — | — | — | — |
| Glyceryl Dibehenate | — | 15.00 | — | — | — | — |
| Glyceryl Palmitostearate | — | — | 15.00 | — | — | — |
| Sodium lauryl sulfate | — | — | — | 15.00 | — | — |
| Poloxamer 188 | — | — | — | — | 15.00 | — |
| PEG 8000 | — | — | — | — | — | 15.00 |
| total | 500.00 | 500.00 | 500.00 | 500.00 | 500.00 | 500.00 |

TABLE 2.32

| Formulations 12A-12F, Capsule Dissolution Results | | | | |
|---|---|---|---|---|
| | Formulation 12A | | | |
| Sample | 15 min | 30 min | 45 min | 60 min |
| 1 | 73 | 78 | 79 | 80 |
| 2 | 72 | 78 | 80 | 81 |
| Avg | 72 | 78 | 80 | 80 |
| | Formulation 12B | | | |
| Sample | 15 min | 30 min | 45 min | 60 min |
| 1 | 77 | 80 | 82 | 83 |
| 2 | 76 | 82 | 82 | 83 |
| Avg | 76 | 81 | 82 | 83 |

TABLE 2.32-continued

Formulations 12A-12F, Capsule Dissolution Results

Formulation 12C

| Sample | 15 min | 30 min | 45 min | 60 min |
|---|---|---|---|---|
| 1 | 80 | 84 | 84 | 85 |
| 2 | 72 | 78 | 80 | 81 |
| Avg | 76 | 81 | 82 | 83 |

Formulation 12D

| Sample | 15 min | 30 min | 45 min | 60 min |
|---|---|---|---|---|
| 1 | 53 | 55 | 55 | 56 |
| 2 | 51 | 52 | 53 | 54 |
| Avg | 52 | 53 | 54 | 55 |

Formulation 12E

| Sample | 15 min | 30 min | 45 min | 60 min |
|---|---|---|---|---|
| 1 | 77 | 81 | 82 | 83 |
| 2 | 79 | 83 | 85 | 85 |
| Avg | 78 | 82 | 83 | 84 |

Formulation 12F

| Sample | 15 min | 30 min | 45 min | 60 min |
|---|---|---|---|---|
| 1 | 81 | 84 | 85 | 86 |
| 2 | 84 | 86 | 89 | 89 |
| Avg | 83 | 85 | 87 | 88 |

50 mg maralixibat (~52.6 mg maralixibat chloride) in a capsule shell

| Sample | 15 min | 30 min | 45 min | 60 min |
|---|---|---|---|---|
| 1 | 89 | 94 | 95 | 95 |
| 2 | 88 | 95 | 96 | 96 |
| Avg | 89 | 95 | 96 | 96 |

For the lubricant and water soluble excipient results, hydrogenated cottonseed oil, glyceryl dibehenate, glyceryl palmitostearate and poloxamer 188 had dissolution comparable to the DS alone in capsule. The capsules with sodium lauryl sulfate had slow release, <60% at 60 min. Formulations were next created with four of the alternative lubricants considered most viable-hydrogenated cottonseed oil, PEG8000, glyceryl dibehenate and glyceryl palmitostearate—for evaluation as a compressed tablet. A 10 mg tablet was compressed for each formulation using ¼" SRC tooling with compression force of ~2 kN compression force at 3 kp to 5 kp hardness range. Upon compression additional lubricant was added to the formulation based on sticking observations as detailed below.

Hydrogenated cottonseed oil was evaluated up to 5% in 1% increments, and severe punch hazing was observed during compression at all of these lubricant levels. PEG8000 was next evaluated at 1%, 3%, 5%, 8% and 10%. Broken tablets were observed after ~20 tablets were compressed at all levels of increasing PEG8000. Glyceryl dibehenate was evaluated at 1%, 3% and 5%. Breakage was observed at 1% and 3% levels. No breakage was observed at the 5% level, but the punch face had hazing and clear evidence of material build-up. Glyceryl palmitostearate was the next to be evaluated at 1%, 3%, 5% and 10%. No breakage was observed at all levels for the glyceryl palmitostearate compressed tablet (Formulation 12C), but punch hazing and material build-up was noticed up to the 5% level. At 10% level, tablets appear to have good hardness still and minimal punch hazing even after 50 tablets compressed.

Figure 24:
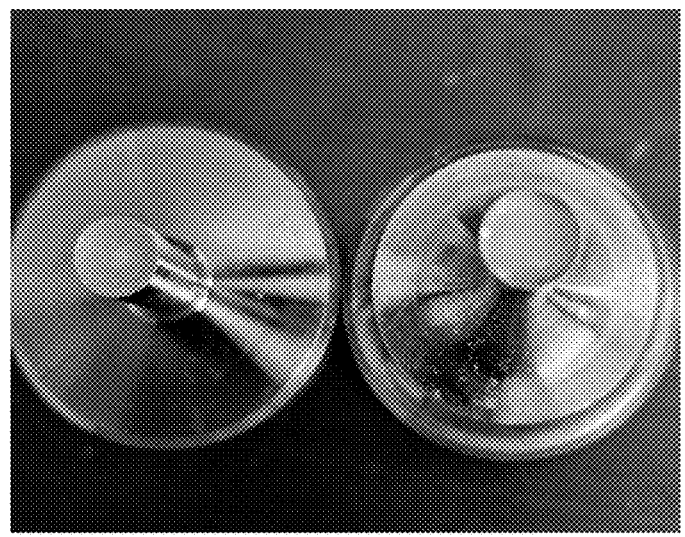
FIG. 24 shows a photo of tooling with picking of Formulation 13A.

Remaining material of the hydrogenated cottonseed oil formulation was further evaluated for compression with an addition of 5% lubricant (total of 10% level, Formulation 13A, Table 2.33). During compression, picking was still observed after a longer run of ~5 mins (30 g total) tablets produced. A photo of this tooling with picking is shown in FIG. 24. At this point the formulation with 10% glyceryl palmitostearate was considered to be the most viable.

TABLE 2.33

| Component | Formulation 13A |
|---|---|
| [[MXT]]MRX salt loop milled | 9.76% |
| Lactose Monohydrate | 21.79% |
| MCC | 57.99% |
| Silicon Dioxide | 0.46% |
| Hydrogenated cottonseed oil | 10.00% |
| total | 100.00% |

A formulation with 7.5% glyceryl palmitostearate (Formulation 13B, Table 2.34) was evaluated to see if the lubricant level could be titrated down. Initially, this formulation looked okay, but then picking was observed after longer run. An addition of 1.5% lubricant for a total of 9% was added to the remaining batch to make Formulation 13C (Table 2.35). No picking was observed during compression of 10 mg and 30 mg dosage forms. Tablet samples of Formulation 13C were tested for dissolution and the tablets disintegrated slowly in the dissolution media. To address this, addition of 5% crospovidone in the remaining samples of Formulation 13C was made to yield Formulation 13 to reduce the disintegration time of the tablets. The disintegration test was performed on the Formulation 13 tablets for 10 mg and 30 mg and the results were 57 secs for 10 mg and 137 secs for the 30 mg. Comparison of the formulation with 0.7500 magnesium stearate with 500 crospovidone (Formulation 14, Table 2.36) vs. 9% glyceryl palmitostearate and 5 crospovidone (Formulation 13, Table 2.37) were evaluated to see which formulation would give better dissolution results. Compression summary results are outlined in Table 2.38. Dissolution results of Formulation 14 are exhibited in FIGS. 25-26 and Tables 2.39 and 2.40. Dissolution results of Formulation 13 are exhibited in FIG. 27 and Table 2.41.

TABLE 2.34

Formulation 13B

| Component | | 10 mg (mg/tab) | 30 mg (mg/cap) |
|---|---|---|---|
| [[MXT]]MRX salt loop milled | 10.52% | 10.52 | 31.56 |
| Lactose Monohydrate | 22.47% | 22.47 | 67.41 |
| MCC | 59.03% | 59.03 | 177.09 |
| Silicon Dioxide | 0.50% | 0.50 | 1.50 |
| Glyceryl Palmitostearate | 7.5% | 7.50 | 22.50 |
| total | 100.00% | 100.00 | 300.00 |

TABLE 2.35

Formulation 13C

| Component | | 10 mg (mg/cap) | 30 mg (mg/cap) |
|---|---|---|---|
| [[MXT]] MRX salt loop milled | 10.35% | 10.35 | 31.04 |
| Lactose Monohydrate | 22.10% | 22.10 | 66.30 |
| MCC | 58.06% | 58.06 | 174.18 |
| Silicon Dioxide | 0.49% | 0.49 | 1.48 |
| Glyceryl Palmitostearate | 9.00% | 9.00 | 27.00 |
| total | 100.00% | 100.00 | 300.00 |

TABLE 2.36

Formulation 14

| Component | | 10 mg (mg/cap) | 30 mg (mg/cap) | 50 mg (mg/cap) |
|---|---|---|---|---|
| [[MXT]]MRX salt loop milled | 10.02% | 10.02 | 30.06 | 50.10 |
| Lactose Monohydrate | 22.36% | 22.36 | 67.09 | 111.81 |
| MCC | 61.67% | 61.67 | 185.00 | 308.33 |
| Silicon Dioxide | 0.48% | 0.48 | 1.43 | 2.38 |
| Magnesium Stearate | 0.71% | 0.71 | 2.14 | 3.57 |
| Crospovidone | 4.76% | 4.76 | 14.29 | 23.81 |
| total | 100.00% | 100.00 | 300.00 | 500.00 |

TABLE 2.37

Formulation 13

| Component | | 10 mg (mg/cap) | 30 mg (mg/cap) | 50 mg (mg/cap) |
|---|---|---|---|---|
| [[MXT]] MRX salt loop milled | 9.83% | 9.83 | 29.49 | 49.15 |
| Lactose Monohydrate | 21.00% | 21.00 | 62.99 | 104.98 |
| MCC | 55.16% | 55.16 | 165.47 | 275.79 |
| Silicon Dioxide | 0.47% | 0.47 | 1.40 | 2.34 |
| Glyceryl Palmitostearate | 8.55% | 8.55 | 25.65 | 42.75 |
| Crospovidone | 5.00% | 5.00 | 15.00 | 25.00 |
| total | 100.00% | 100.00 | 300.00 | 500.00 |

TABLE 2.38

Compression Comparison between Formulations 14 & 13

| Parameter | Formulation 14 | | | Formulation 13 |
|---|---|---|---|---|
| | 10 mg | 30 mg | 50 mg | 50 mg |
| Force (kN) | 2.7 | 5.4 | 8.5 | 10.5 |
| Avg Mass (mg) | 103.85 | 318.28 | 523.97 | 531.2 |
| Mass RSD (%) | 0.51% | 0.42% | 0.11% | 0.37% |
| Avg Hardness (kp) | 4.55 | 10.5 | 19.7 | 20.6 |
| Disintegration (s) | 10 secs | 31 secs | 71 secs | >10 mins |

TABLE 2.39

Dissolution results of Formulation 14 in 0.1N HCl 10 mg

| Sample | 15 min | 30 min | 45 min | 60 min |
|---|---|---|---|---|
| 1 | 80 | 84 | 87 | 89 |
| 2 | 77 | 80 | 84 | 87 |
| Avg | 79 | 82 | 85 | 88 |

30 mg

| Sample | 15 min | 30 min | 45 min | 60 min |
|---|---|---|---|---|
| 1 | 79 | 82 | 85 | 87 |
| 2 | 93 | 95 | 96 | 97 |
| Avg | 86 | 88 | 90 | 92 |

50 mg

| Sample | 15 min | 30 min | 45 min | 60 min |
|---|---|---|---|---|
| 1 | 94 | 96 | 96 | 97 |
| 2 | 95 | 96 | 97 | 98 |
| Avg | 95 | 96 | 97 | 97 |

TABLE 2.40

Dissolution results, Formulation 14 in pH 6.8 phosphate buffer 10 mg

| Sample | 15 min | 30 min | 45 min | 60 min |
|---|---|---|---|---|
| 1 | 59 | 65 | 69 | 71 |
| 2 | 62 | 67 | 70 | 71 |
| Avg | 61 | 66 | 70 | 71 |

30 mg

| Sample | 15 min | 30 min | 45 min | 60 min |
|---|---|---|---|---|
| 1 | 65 | 71 | 77 | 79 |
| 2 | 69 | 74 | 76 | 77 |
| Avg | 67 | 72 | 76 | 78 |

50 mg

| Sample | 15 min | 30 min | 45 min | 60 min |
|---|---|---|---|---|
| 1 | 70 | 79 | 85 | 88 |
| 2 | 79 | 86 | 89 | 91 |
| Avg | 75 | 82 | 87 | 90 |

TABLE 2.41

Dissolution results, Formulation 13, 50 mg Tablets 0.1N HCl

| Sample | 15 min | 30 min | 45 min | 60 min |
|---|---|---|---|---|
| 1 | 39 | 64 | 77 | 85 |
| 2 | 44 | 67 | 96 | 100 |
| Avg | 42 | 65 | 87 | 92 | pH 6.8 Phosphate Buffer

| Sample | 15 min | 30 min | 45 min | 60 min |
|---|---|---|---|---|
| 1 | 84 | 97 | 98 | 98 |
| 2 | 89 | 94 | 94 | 94 |
| Avg | 87 | 95 | 96 | 96 |

Figure 25:
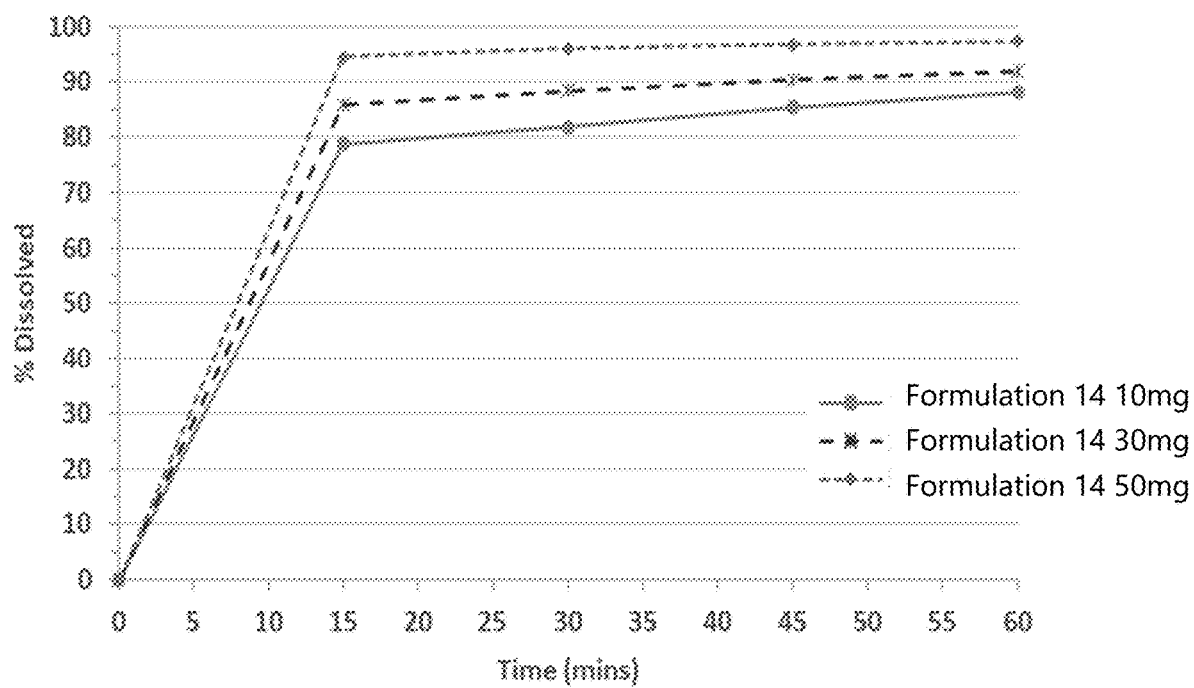
FIG. 25 shows dissolution results of Formulation 14 in 0.1N HCl.
Figure 26:
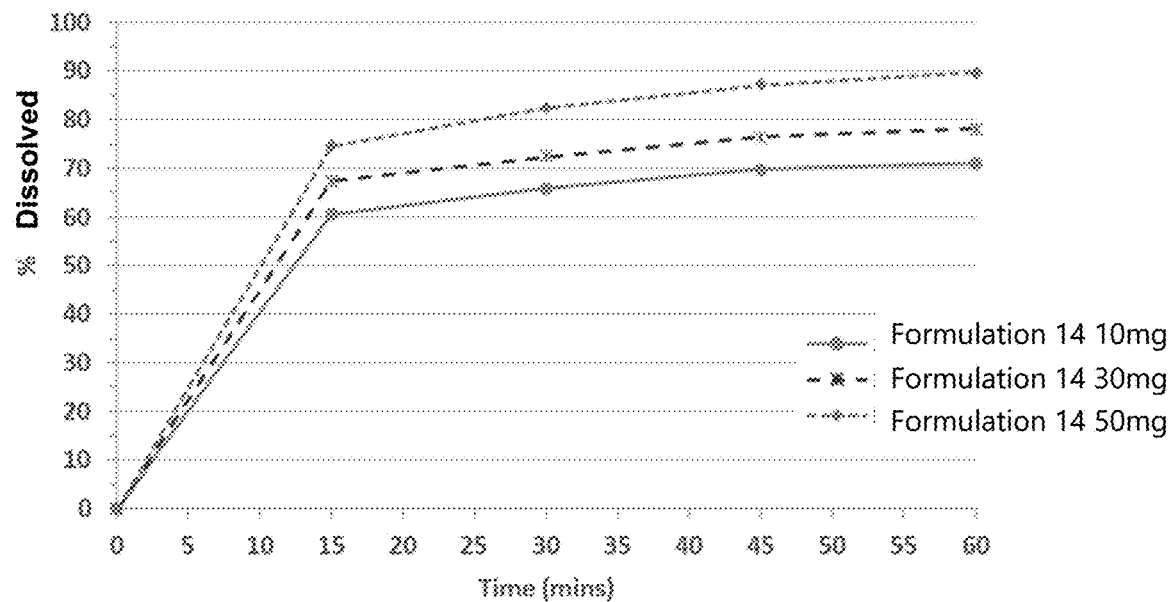
FIG. 26 shows dissolution results of Formulation 14 in pH 6.8 phosphate buffer.
Figure 27:
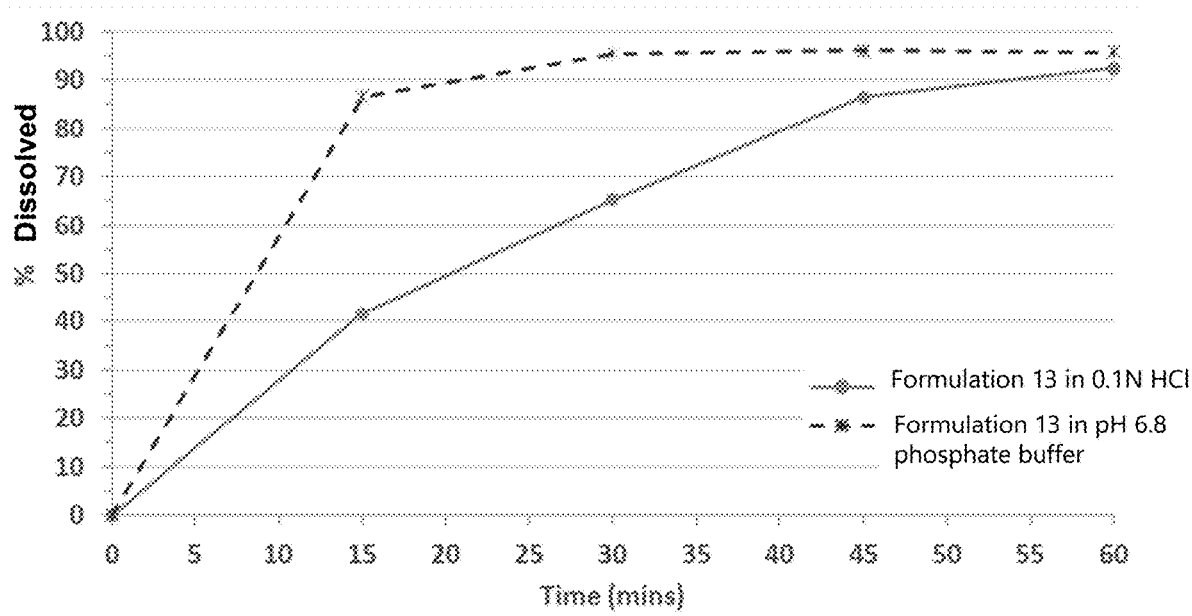
FIG. 27 shows dissolution results of 50 mg dose tablets of Formulation 13 in 0.1N HCl and pH 6.8 phosphate buffer.

Dissolution was evaluated using the two different lubricant formulations. Disintegration was slower for the glyceryl palmitostearate formulation, Formulation 13, compared to the magnesium stearate formulation, Formulation 14 (Table 2.38) in the compression studies. Formulation 14 had a fast release in 0.1N HCl media across the dose range (FIG. 25) compared to in pH 6.8 phosphate buffer (FIG. 26). In 0.7N HCl and in pH 6.8 phosphate buffer, final release percentage of each dosage form of Formulation 14 was proportional to dose with an unexpected and surprising finding that the lower dose has a lower final release percentage at the plateau (FIGS. 25 and 26). Dissolution results of Formulation 13 were different. Surprisingly, the 50 mg tablets of Formulation 13 were dissolved faster in the pH 6.8 phosphate buffer than in the 0.1N HCl media (FIG. 27), which presents a more favorable dissolution profile. The slow dissolution in 0.1N HCl may be attributed to the high tablet hardness of ~20 kp (Table 2.38).

A glyceryl palmitostearate based formulation, Formulation 15, was further prepared for a compressibility study of the 3 dosages, 10 mg, 30 mg, and 50 mg.

Figure 28:
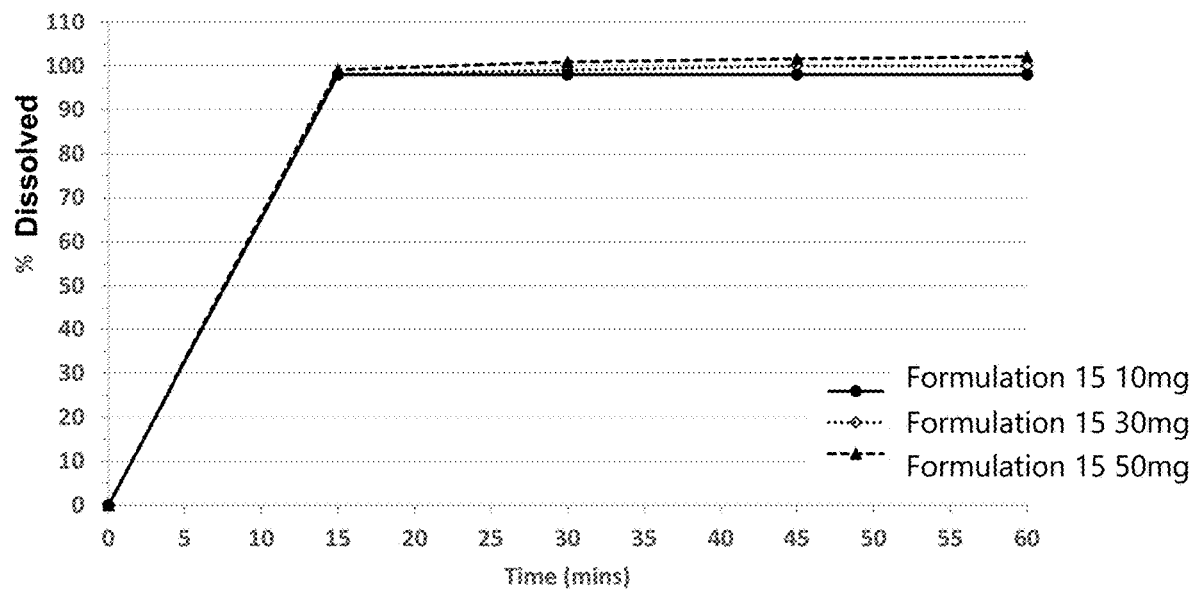
FIG. 28 shows dissolution results of Formulation 15 in 0.1N HCl.
Figure 29:
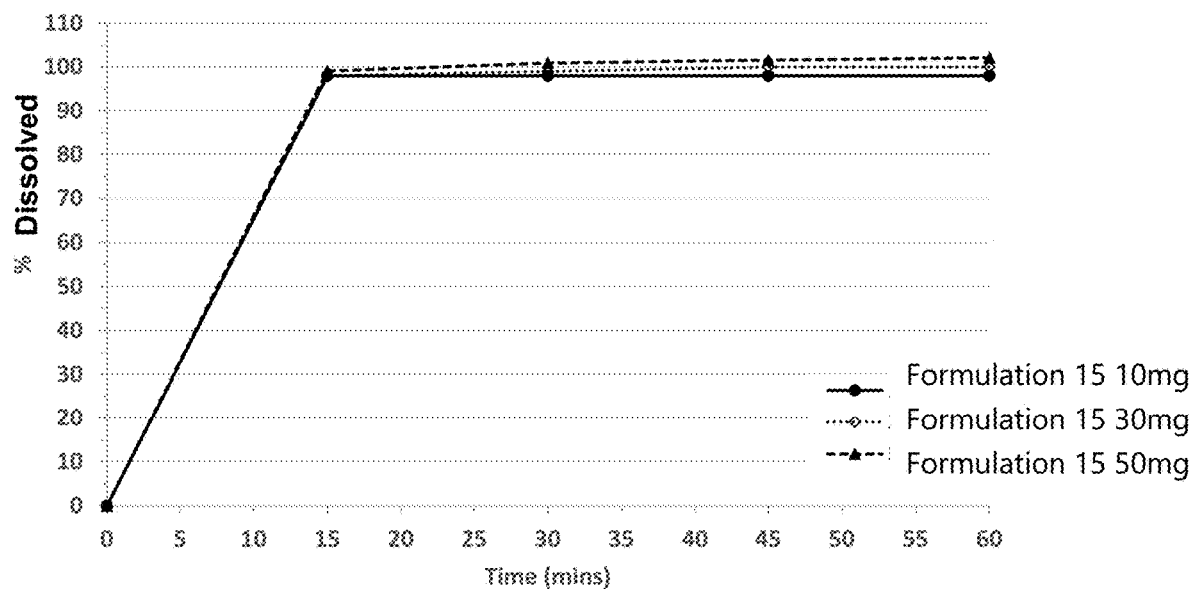
FIG. 29 shows dissolution results of Formulation 15 in pH 4.5 acetate buffer.
Figure 30:
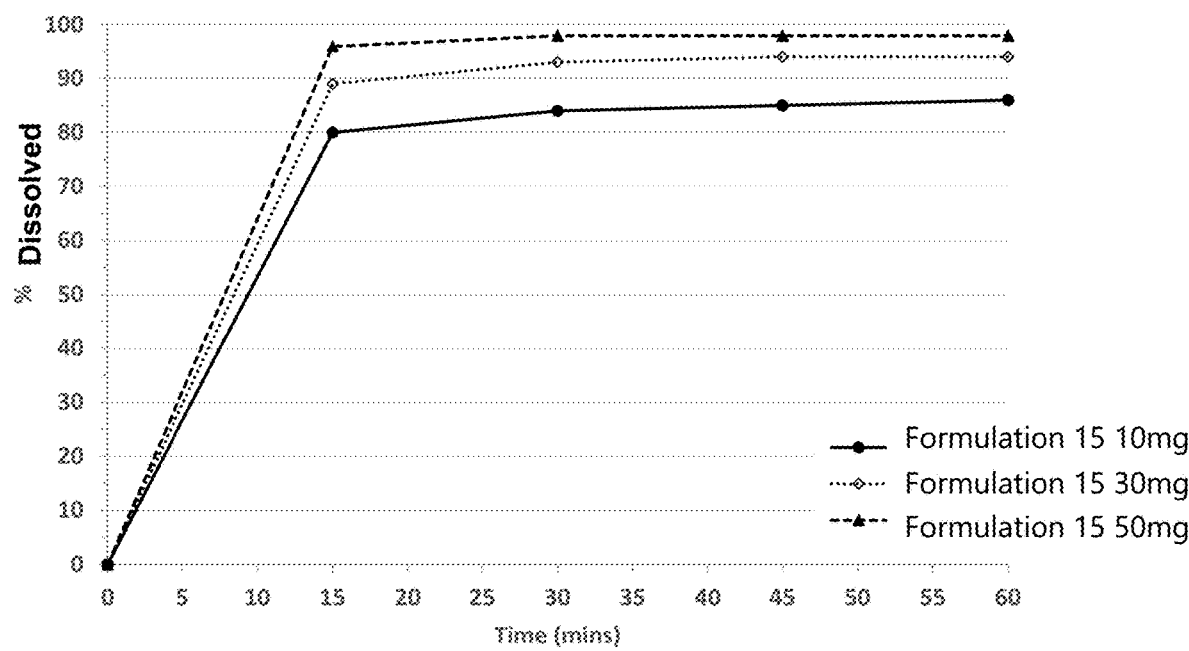
FIG. 30 shows dissolution results of Formulation 15 in pH 6.8 phosphate buffer.

The formulation (Formulation 15) is presented in Table 2.42 and tabulated results of the compression study are presented in Table 2.43. Dissolution results are provided in FIGS. 28-30 and Tables 2.44, 2.45, and 2.46. In FIG. 30, it is unexpected and surprising to find that the higher dose is associated with higher dissolution percentage.

TABLE 2.44

Formulation 15 Dissolution Results, 0.1N HCl

| | 10 mg | | | |
|---|---|---|---|---|
| Sample | 15 min | 30 min | 45 min | 60 min |
| 1 | 99 | 98 | 98 | 98 |
| 2 | 96 | 97 | 97 | 95 |
| 3 | 97 | 97 | 96 | 96 |
| 4 | 98 | 99 | 99 | 100 |
| 5 | 99 | 98 | 99 | 99 |
| 6 | 98 | 97 | 97 | 98 |
| 7 | 97 | 98 | 98 | 98 |
| 8 | 97 | 99 | 99 | 100 |
| 9 | 98 | 101 | 101 | 101 |
| 10 | 100 | 101 | 102 | 102 |
| 11 | 98 | 100 | 100 | 100 |
| 12 | 99 | 100 | 100 | 101 |
| Avg | 98 | 99 | 99 | 99 |
| % RSD | 1.2% | 1.5% | 1.8% | 2.1% |

| | 30 mg | | | |
|---|---|---|---|---|
| Sample | 15 min | 30 min | 45 min | 60 min |
| 1 | 93 | 97 | 99 | 100 |
| 2 | 99 | 100 | 100 | 101 |
| 3 | 102 | 101 | 101 | 101 |
| 4 | 99 | 100 | 101 | 101 |
| 5 | 94 | 96 | 98 | 99 |
| 6 | 99 | 100 | 100 | 100 |
| Avg | 98 | 99 | 100 | 100 |
| % RSD | 3.4% | 2.1% | 1.4% | 1.0% |

TABLE 2.42

| | Formulation 15 | | | | |
|---|---|---|---|---|---|
| Component | Grade/Vendor | %/tab | 10 mg (mg/tab) | 30 mg (mg/tab) | 50 mg (mg/tab) |
| MRX salt (Loop milled) | n/a | 10.53% | 10.53 | 31.59 | 52.65 |
| Lactose monohydrate | FastFlo 316, Kerry/Sheffield | 24.97% | 24.97 | 74.91 | 124.85 |
| Microcrystalline cellulose | Avicel ® PH302, Dupont | 50.00% | 50.00 | 150.00 | 250.00 |
| Silicon dioxide | Cab-O-Sil ® M5P, Cabot | 0.50% | 0.50 | 1.50 | 2.50 |
| Crospovidone | Kollidon CL, BASF | 5.00% | 5.00 | 15.00 | 25.00 |
| Glyceryl Palmitostearate | Gattefosse | 9.00% | 9.00 | 27.00 | 45.00 |
| total | | 100.00% | 100.00 | 300.00 | 500.00 |

TABLE 2.43

| | Compressibility study results | | | | | | | | |
|---|---|---|---|---|---|---|---|---|---|
| | Formulation 15 10 mg | | | Formulation 15 30 mg | | | Formulation 15 50 mg | | |
| Parameter | Run 1 | Run 2 | Run 3 | Run 1 | Run 2 | Run 3 | Run 1 | Run 2 | Run 3 |
| Force (kN) | 1.8 | 3.3 | 5.7 | 3.4 | 5.2 | 5.5 | 4.8 | 6.0 | 7.7 |
| Avg Mass (mg) | 100.6 | 100.5 | 100.1 | 299.2 | 302.3 | 302.0 | 497.4 | 497.9 | 498.0 |
| Mass RSD (%) | 0.50 | 0.56 | 0.70 | 0.52 | 0.43 | 0.49 | 0.51 | 0.41 | 0.25 |
| Avg Hardness (kp) | 3.2 | 5.4 | 7.5 | 7.0 | 10.7 | 12.6 | 10.6 | 12.6 | 15.6 |
| Friability (%) | 0.49 | 0.16 | 0.08 | 0.21 | 0.13 | 0.12 | 0.09 | 0.09 | 0.05 |
| Disintegration (s) | 20 secs | 2 min 10 secs | 5 mins 25 secs | 1 min 12 secs | 3 mins 28 secs | 5 mins 13 secs | 1 min 26 secs | 3 mins 13 secs | 6 mins 4 secs |

TABLE 2.44-continued

Formulation 15 Dissolution Results, 0.1N HCl

| | 50 mg | | | |
|---|---|---|---|---|
| Sample | 15 min | 30 min | 45 min | 60 min |
| 1 | 99 | 101 | 102 | 102 |
| 2 | 98 | 99 | 100 | 101 |
| 3 | 96 | 98 | 99 | 100 |
| 4 | 97 | 99 | 100 | 101 |
| 5 | 99 | 101 | 102 | 102 |
| 6 | 99 | 101 | 102 | 102 |
| 7 | 97 | 98 | 99 | 99 |
| 8 | 95 | 96 | 98 | 98 |
| 9 | 96 | 98 | 99 | 99 |
| 10 | 95 | 97 | 98 | 99 |
| 11 | 95 | 97 | 98 | 99 |
| 12 | 97 | 98 | 99 | 99 |
| Avg | 97 | 99 | 100 | 100 |
| % RSD | 1.6% | 1.7% | 1.6% | 1.4% |

TABLE 2.45

Formulation 15 Dissolution Results, pH 4.5 Acetate Buffer

| | 10 mg | | | |
|---|---|---|---|---|
| Sample | 15 min | 30 min | 45 min | 60 min |
| 1 | 93 | 93 | 93 | 94 |
| 2 | 95 | 96 | 96 | 96 |
| 3 | 94 | 96 | 97 | 97 |
| 4 | 94 | 95 | 96 | 96 |
| 5 | 94 | 97 | 96 | 95 |
| 6 | 96 | 94 | 94 | 95 |
| 7 | 87 | 92 | 93 | 93 |
| 8 | 93 | 93 | 94 | 95 |
| 9 | 88 | 89 | 88 | 89 |
| 10 | 87 | 89 | 89 | 89 |
| 11 | 85 | 93 | 91 | 94 |
| 12 | 90 | 92 | 93 | 93 |
| Avg | 91 | 93 | 93 | 94 |
| % RSD | 4.1% | 2.7% | 3.0% | 2.7% |

| | 30 mg | | | |
|---|---|---|---|---|
| Sample | 15 min | 30 min | 45 min | 60 min |
| 1 | 100 | 101 | 102 | 103 |
| 2 | 97 | 99 | 99 | 100 |
| 3 | 101 | 102 | 103 | 102 |
| 4 | 98 | 98 | 100 | 99 |
| 5 | 95 | 98 | 98 | 99 |
| 6 | 102 | 102 | 103 | 103 |
| Avg | 99 | 100 | 101 | 101 |
| % RSD | 2.7% | 1.9% | 1.9% | 1.8% |

| | 50 mg | | | |
|---|---|---|---|---|
| Sample | 15 min | 30 min | 45 min | 60 min |
| 1 | 100 | 102 | 101 | 103 |
| 2 | 100 | 103 | 103 | 104 |
| 3 | 99 | 103 | 104 | 104 |
| 4 | 96 | 99 | 100 | 101 |
| 5 | 101 | 103 | 104 | 104 |
| 6 | 98 | 101 | 102 | 103 |
| 7 | 93 | 95 | 95 | 95 |
| 8 | 92 | 94 | 96 | 96 |
| 9 | 97 | 98 | 98 | 98 |
| 10 | 92 | 94 | 95 | 95 |
| 11 | 96 | 97 | 97 | 97 |
| 12 | 94 | 95 | 95 | 96 |
| Avg | 97 | 99 | 99 | 100 |
| % RSD | 3.3% | 3.7% | 3.6% | 3.8% |

TABLE 2.46

Formulation 15 Dissolution Results, pH 6.8 Phosphate Buffer

| | 10 mg | | | |
|---|---|---|---|---|
| Sample | 15 min | 30 min | 45 min | 60 min |
| 1 | 79 | 84 | 84 | 85 |
| 2 | 81 | 86 | 87 | 87 |
| 3 | 80 | 84 | 85 | 87 |
| 4 | 79 | 83 | 85 | 87 |
| 5 | 80 | 83 | 86 | 87 |
| 6 | 80 | 84 | 86 | 85 |
| 7 | 84 | 89 | 89 | 89 |
| 8 | 83 | 88 | 86 | 88 |
| 9 | 84 | 86 | 86 | 85 |
| 10 | 82 | 85 | 86 | 85 |
| 11 | 84 | 87 | 87 | 87 |
| 12 | 83 | 83 | 85 | 84 |
| Avg | 82 | 85 | 86 | 86 |
| % RSD | 2.4% | 2.4% | 1.5% | 1.7% |

| | 30 mg | | | |
|---|---|---|---|---|
| Sample | 15 min | 30 min | 45 min | 60 min |
| 1 | 88 | 94 | 95 | 95 |
| 2 | 87 | 93 | 94 | 93 |
| 3 | 89 | 90 | 92 | 93 |
| 4 | 91 | 93 | 95 | 95 |
| 5 | 89 | 92 | 94 | 94 |
| 6 | 88 | 92 | 94 | 93 |
| Avg | 89 | 93 | 94 | 94 |
| % RSD | 1.6% | 1.4% | 1.1% | 1.1% |

| | 50 mg | | | |
|---|---|---|---|---|
| Sample | 15 min | 30 min | 45 min | 60 min |
| 1 | 96 | 98 | 99 | 98 |
| 2 | 97 | 100 | 99 | 99 |
| 3 | 97 | 99 | 98 | 98 |
| 4 | 93 | 97 | 97 | 98 |
| 5 | 95 | 97 | 98 | 98 |
| 6 | 95 | 98 | 99 | 98 |
| 7 | 93 | 95 | 95 | 95 |
| 8 | 91 | 94 | 93 | 93 |
| 9 | 93 | 96 | 96 | 96 |
| 10 | 94 | 95 | 95 | 96 |
| 11 | 91 | 92 | 92 | 93 |
| 12 | 93 | 94 | 95 | 94 |
| Avg | 94 | 96 | 96 | 96 |
| % RSD | 2.2% | 2.4% | 2.5% | 2.2% |

Figure 31:
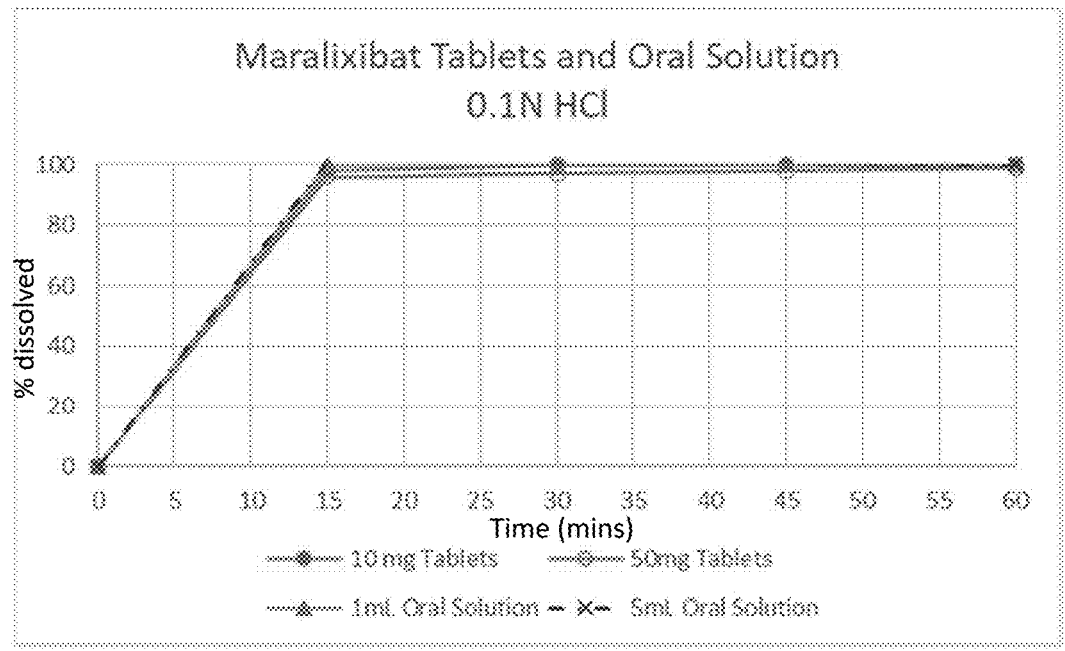
FIG. 31 shows an overlay of maralixibat dissolution profiles of tablets and oral solution in 0.1N HCl.

The oral solution formulation is listed in Table 2.47, as shown by example in Kommuru, T., et al., U.S. patent Ser. No. 17/973,194, which is incorporated herein in its entirety. Individual dissolution results for various product configurations of tablets and oral solution in 0.1N HCl are presented in Tables 2.44, 2.48, and 2.49, and an overlay of each dissolution profile is presented in FIG. 31.

TABLE 2.47

Oral Solution Formulation

| Ingredient | Grade | Function | Formulation (Quantity per Unit Dose, % w/w) |
|---|---|---|---|
| Maralixibat Chloride[a] | In-House | MRX Drug Substance (API) | Fixed concentration (5 to 50 mg/mL) |
| Propylene glycol | USP Ph. Eur. | Co-solvent and preservative | 32.03 to 35.00 |
| Purified water[b] | USP Ph. Eur. | Solvent | 58.10 to 63.50 |

TABLE 2.47-continued

Oral Solution Formulation

| Ingredient | Grade | Function | Formulation (Quantity per Unit Dose, % w/w) |
|---|---|---|---|
| Disodium EDTA Dihydrate | USP Ph. Eur. | Antioxidant | 0.1 |
| Sucralose | NF Ph. Eur. | Sweetener | 0.92 to 1.00 |
| Grape Flavor | In-House | Taste Masking Agent | 0.46 to 0.50 |
| | | Total | 100% |

[a] quantity is expressed as maralixibat chloride (salt form), which can be converted to maralixibat (free base) using a conversion factor of 0.95
[b] amount of purified water is adjusted based on the assay of maralixibat chloride in order to maintain the weight of 1.00 mL of the solution

TABLE 2.48

1 mL Oral Solution Dissolution - 0.1N HCl

| Replicate | 15 min | 30 min | 45 min | 60 min |
|---|---|---|---|---|
| 1 | 100 | 101 | 101 | 101 |
| 2 | 100 | 101 | 101 | 101 |
| 3 | 100 | 100 | 100 | 101 |
| 4 | 100 | 101 | 102 | 101 |
| 5 | 100 | 101 | 101 | 101 |
| 6 | 101 | 101 | 102 | 101 |
| Average | 100 | 101 | 101 | 101 |
| RSD | 0 | 0 | 0 | 0 |

TABLE 2.49

5 mL Oral Solution Dissolution - 0.1N HCl

| Replicate | 15 min | 30 min | 45 min | 60 min |
|---|---|---|---|---|
| 1 | 100 | 101 | 101 | 96 |
| 2 | 102 | 103 | 103 | 103 |
| 3 | 100 | 100 | 100 | 99 |
| 4 | 100 | 100 | 100 | 100 |
| 5 | 100 | 100 | 100 | 101 |
| 6 | 101 | 102 | 102 | 102 |
| Average | 101 | 101 | 101 | 100 |
| RSD | 1 | 1 | 1 | 2 |

Figure 32:
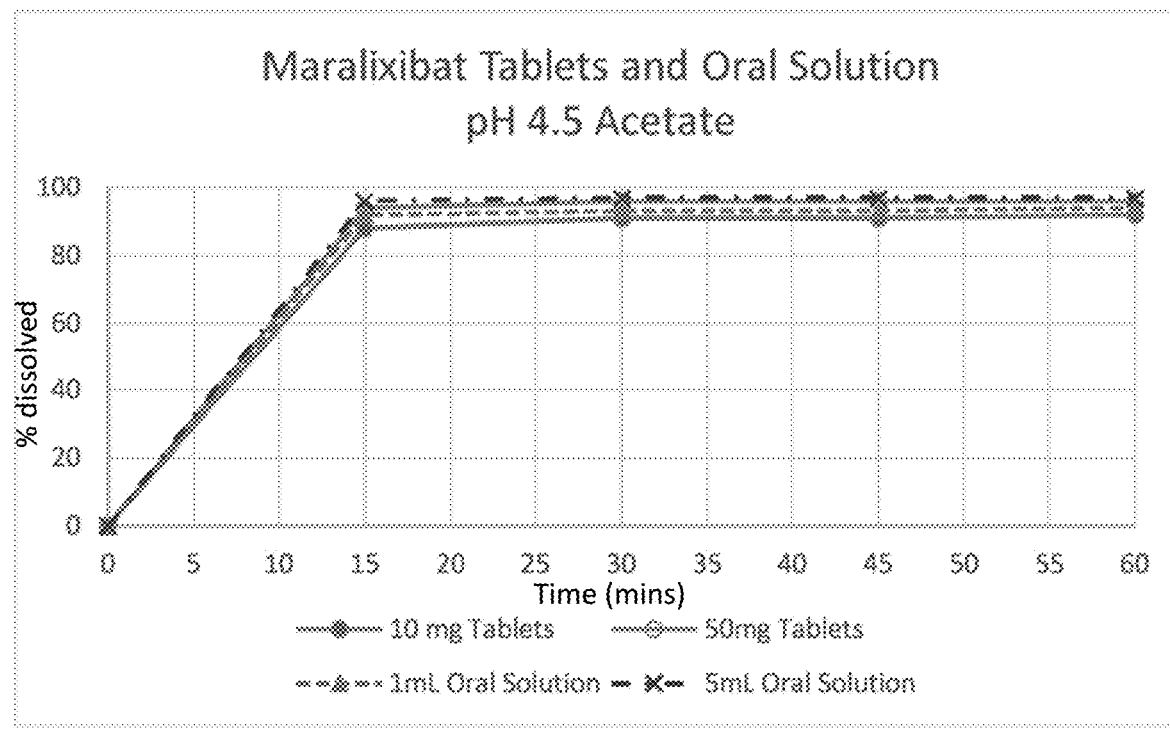
FIG. 32 shows an overlay of maralixibat dissolution profiles of tablets and oral solution in pH 4.5 acetate buffer.

Individual dissolution results for various product configurations of tablets and oral solution in pH 4.5 acetate buffer are presented in Tables 2.45, 2.50, and 2.51, and an overlay of each dissolution profile is presented in FIG. 32.

TABLE 2.50

1 mL Oral Solution Dissolution - pH 4.5 Acetate Buffer

| Replicate | 15 min | 30 min | 45 min | 60 min |
|---|---|---|---|---|
| 1 | 94 | 91 | 94 | 92 |
| 2 | 93 | 92 | 93 | 94 |
| 3 | 91 | 93 | 93 | 92 |
| 4 | 92 | 93 | 94 | 95 |
| 5 | 92 | 93 | 92 | 94 |
| 6 | 92 | 92 | 94 | 94 |
| Average | 92 | 93 | 93 | 94 |
| RSD | 1 | 1 | 1 | 1 |

TABLE 2.51

5 mL Oral Solution Dissolution - pH 4.5 Acetate Buffer

| Replicate | 15 min | 30 min | 45 min | 60 min |
|---|---|---|---|---|
| 1 | 93 | 96 | 95 | 96 |
| 2 | 95 | 96 | 97 | 97 |
| 3 | 97 | 98 | 98 | 98 |
| 4 | 94 | 97 | 98 | 97 |
| 5 | 97 | 98 | 98 | 98 |
| 6 | 98 | 99 | 99 | 99 |
| Average | 96 | 97 | 97 | 97 |
| RSD | 2 | 1 | 2 | 1 |

Figure 33:
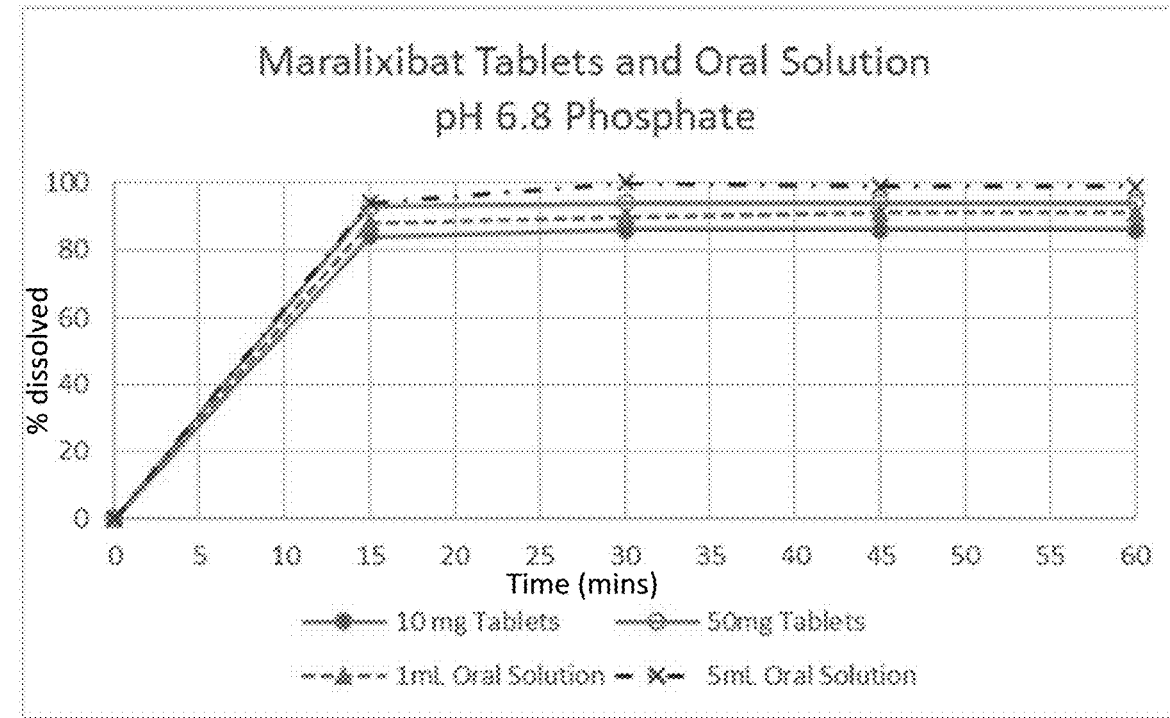
FIG. 33 shows an overlay of maralixibat dissolution profiles of tablets and oral solution in pH 6.8 phosphate buffer.

Individual dissolution results for various product configurations of tablets and oral solution in pH 6.8 phosphate buffer are presented in Tables 2.46, 2.52, and 2.53, and an overlay of each dissolution profile is presented in FIG. 33.

TABLE 2.52

1 mL Oral Solution Dissolution - pH 6.8 Phosphate Buffer

| Replicate | 15 min | 30 min | 45 min | 60 min |
|---|---|---|---|---|
| 1 | 86 | 89 | 89 | 91 |
| 2 | 88 | 90 | 91 | 92 |
| 3 | 89 | 90 | 92 | 91 |
| 4 | 91 | 94 | 93 | 93 |
| 5 | 87 | 89 | 91 | 90 |
| 6 | 90 | 91 | 91 | 92 |
| Average | 88 | 90 | 91 | 91 |
| RSD | 2 | 2 | 1 | 1 |

TABLE 2.53

5 mL Oral Solution Dissolution - pH 6.8 Phosphate Buffer

| Replicate | 15 min | 30 min | 45 min | 60 min |
|---|---|---|---|---|
| 1 | 95 | 99 | 99 | 99 |
| 2 | 93 | 100 | 99 | 99 |
| 3 | 96 | 102 | 100 | 100 |
| 4 | 91 | 97 | 97 | 97 |
| 5 | 96 | 100 | 98 | 98 |
| 6 | 95 | 100 | 98 | 98 |
| Average | 94 | 100 | 99 | 99 |
| RSD | 2 | 1 | 1 | 1 |

Figure 34:
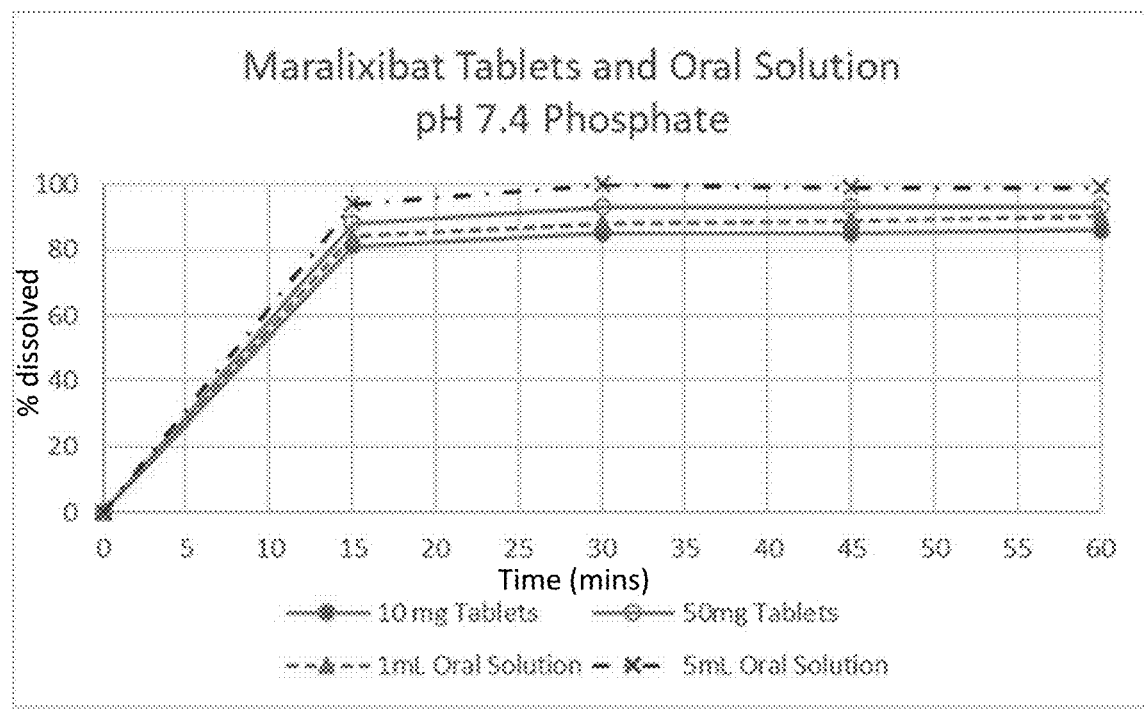
FIG. 34 shows an overlay of maralixibat dissolution profiles of tablets and oral solution in pH 7.4 phosphate buffer.

Individual dissolution results for various product configurations of tablets and oral solution in pH 7.4 phosphate buffer are presented in Tables 2.54, 2.55, 2.56, and 2.57 and an overlay of each dissolution profile is presented in FIG. 34.

TABLE 2.54

Formulation 15 10 mg Tablet Dissolution - pH 7.4 Phosphate Buffer

| Replicate | 15 min | 30 min | 45 min | 60 min |
|---|---|---|---|---|
| 1 | 84 | 88 | 88 | 88 |
| 2 | 79 | 84 | 82 | 85 |
| 3 | 79 | 83 | 82 | 83 |
| 4 | 82 | 87 | 87 | 87 |
| 5 | 84 | 87 | 86 | 86 |
| 6 | 79 | 84 | 83 | 85 |
| Average | 81 | 85 | 85 | 86 |
| RSD | 3 | 3 | 3 | 2 |

TABLE 2.55

Formulation 15 50 mg Tablet Dissolution - pH 7.4 Phosphate Buffer

| Replicate | 15 min | 30 min | 45 min | 60 min |
|---|---|---|---|---|
| 1 | 90 | 96 | 95 | 95 |
| 2 | 89 | 94 | 94 | 94 |
| 3 | 86 | 93 | 92 | 91 |
| 4 | 90 | 94 | 93 | 93 |
| 5 | 85 | 92 | 91 | 91 |
| 6 | 90 | 92 | 91 | 91 |
| Average | 88 | 93 | 93 | 93 |
| RSD | 2 | 2 | 2 | 2 |

TABLE 2.56

1 mL Oral Solution Dissolution - pH 7.4 Phosphate Buffer

| Replicate | 15 min | 30 min | 45 min | 60 min |
|---|---|---|---|---|
| 1 | 84 | 90 | 91 | 93 |
| 2 | 82 | 87 | 89 | 90 |
| 3 | 87 | 88 | 87 | 90 |
| 4 | 84 | 89 | 88 | 90 |
| 5 | 81 | 85 | 88 | 87 |
| 6 | 85 | 89 | 92 | 92 |
| Average | 84 | 88 | 89 | 90 |
| RSD | 2 | 2 | 2 | 2 |

TABLE 2.57

5 mL Oral Solution Dissolution - pH 7.4 Phosphate Buffer

| Replicate | 15 min | 30 min | 45 min | 60 min |
|---|---|---|---|---|
| 1 | 95 | 101 | 101 | 101 |
| 2 | 92 | 97 | 97 | 96 |
| 3 | 98 | 99 | 99 | 99 |
| 4 | 94 | 101 | 100 | 101 |
| 5 | 94 | 100 | 100 | 99 |
| 6 | 94 | 101 | 99 | 100 |
| Average | 94 | 100 | 99 | 99 |
| RSD | 2 | 2 | 1 | 2 |

Figure 35:
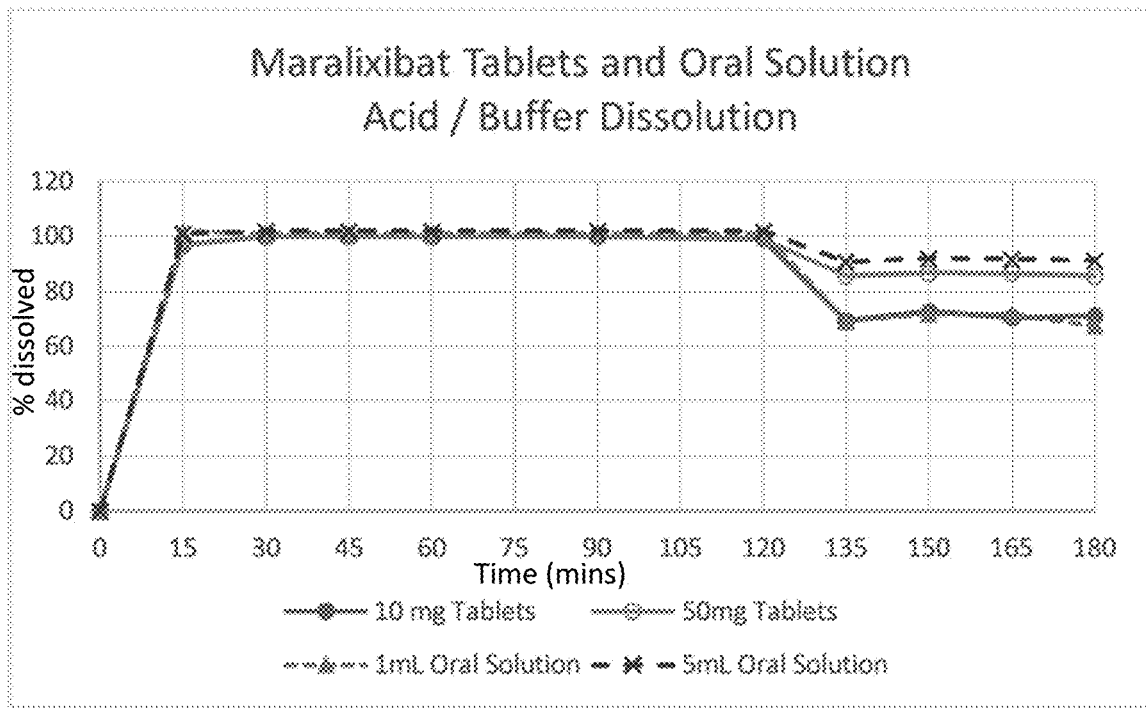
FIG. 35 shows an overlay of maralixibat dissolution profiles of tablets and oral solution through media exchange from 0.1N HCl to pH 6.8 phosphate buffer.
Figure 36:
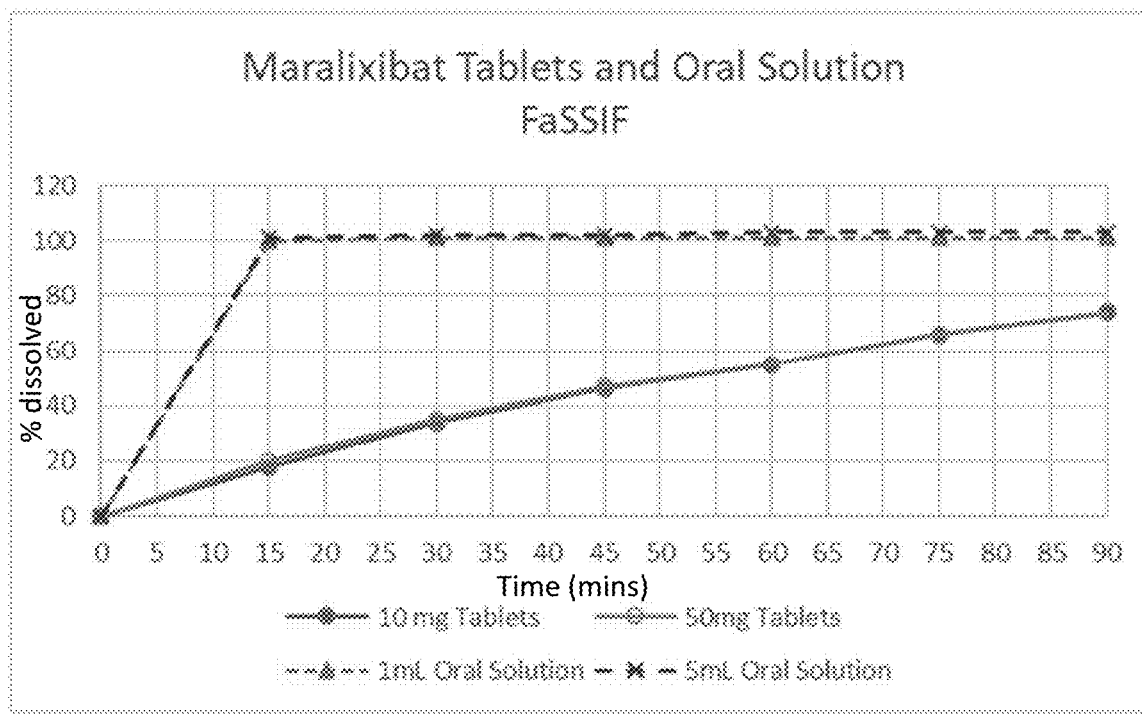
FIG. 36 shows an overlay of maralixibat dissolution profiles of tablets and oral solution in Fasted State Simulated Intestinal Fluid (FaSSIF) media.
Figure 37:
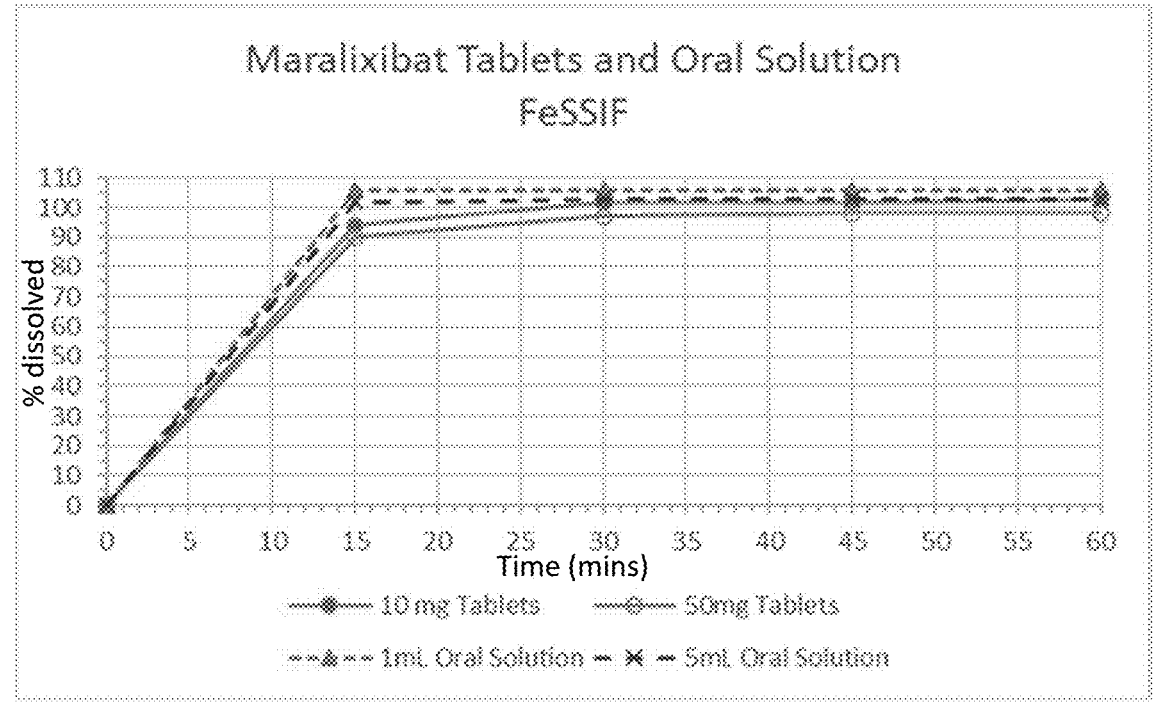
FIG. 37 shows an overlay of maralixibat dissolution profiles of tablets and oral solution in Fed State Simulated Intestinal Fluid (FeSSIF) media.
Figure 38:
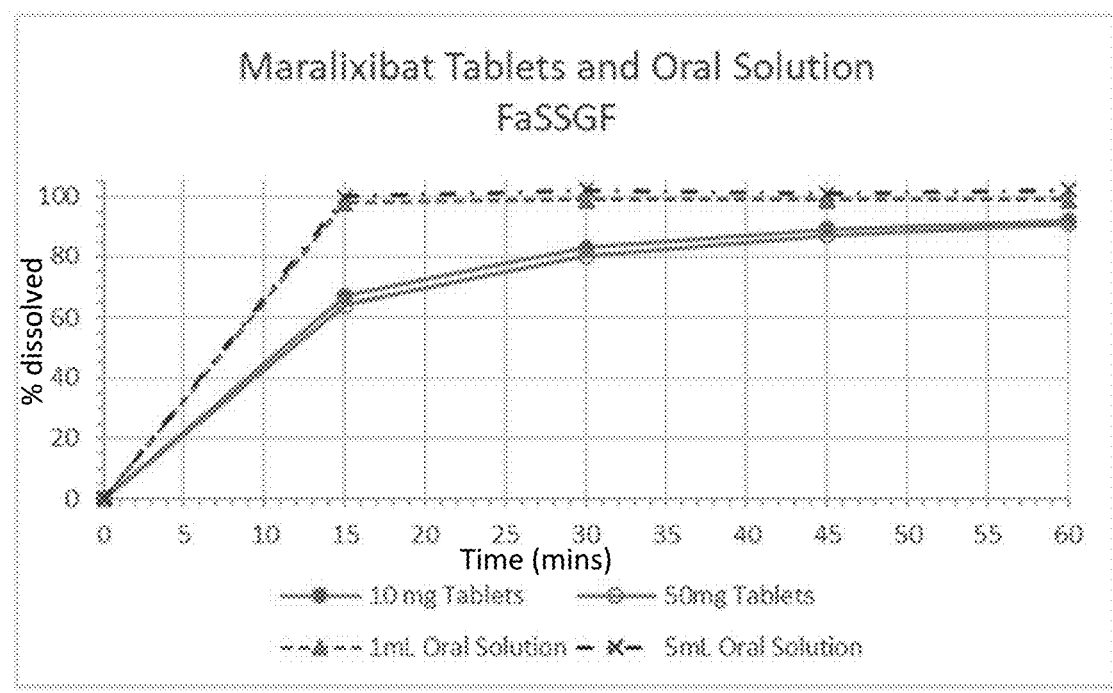
FIG. 38 shows an overlay of maralixibat dissolution profiles of tablets and oral solution in Fasted State Simulated Gastric Fluid (FaSSGF) media.

Media exchange dissolution evaluations were completed from 0.1N HCl to pH 6.8 phosphate buffer for Formulation 15. The acid pH environment was in 750 mL of 0.1N HCl. Following sampling at the 120-minute timepoint, an additional 250 mL of 0.2M phosphate buffer was added to each vessel to result in a final solution pH of 6.8. Individual dissolution results for various product configurations of tablets and oral solutions are presented in Tables 2.58, 2.59, 2.60, and 2.61 and an overlay of each dissolution profile is presented in FIG. 35. It is unexpected and surprising to find that the 50 mg dosage form of Formulation 15 dissolves more than the 50 mg dosage form of Formulation 7 after media exchange (FIG. 15 and FIG. 35). It is also unexpected and surprising to find that after media exchange, the higher dosage 50 mg is associated with higher dissolution percentage (FIG. 35). As such, we have surprisingly found Maralixibat tablet formulations and dosage forms with favorable dissolution profiles. Such formulations and dosage forms of maralixibat have favorable dissolution and pharmacokinetic profiles, which also demonstrate good storage stability.

TABLE 2.58

Formulation 15 10 mg Tablet Dissolution - Media Exchange

| | Stage | | | | | | | | | |
|---|---|---|---|---|---|---|---|---|---|---|
| | Acid Stage | | | | | | Buffer Stage | | | |
| Replicate | 15 min | 30 min | 45 min | 60 min | 90 min | 120 min | 135 min | 150 min | 165 min | 180 min |
| 1 | 98 | 101 | 101 | 101 | 100 | 100 | 69 | 73 | 74 | 68 |
| 2 | 100 | 100 | 101 | 100 | 100 | 100 | 70 | 74 | 70 | 73 |
| 3 | 94 | 102 | 101 | 102 | 103 | 102 | 72 | 75 | 70 | 75 |
| 4 | 97 | 9 | 9 | 98 | 98 | 98 | 69 | 69 | 68 | 72 |
| 5 | 97 | 9 | 9 | 98 | 99 | 98 | 68 | 73 | 71 | 70 |
| 6 | 98 | 100 | 9 | 99 | 98 | 99 | 68 | 72 | 70 | 68 |
| Average | 97 | 100 | 100 | 100 | 100 | 99 | 69 | 73 | 71 | 71 |
| RSD | 2 | 1 | 1 | 2 | 2 | 2 | 3 | 3 | 3 | 4 |

TABLE 2.59

Formulation 15 50 mg Tablet Dissolution - Media Exchange

| | Stage | | | | | | | | | |
|---|---|---|---|---|---|---|---|---|---|---|
| | Acid Stage | | | | | | Buffer Stage | | | |
| Replicate | 15 min | 30 min | 45 min | 60 min | 90 min | 120 min | 135 min | 150 min | 165 min | 180 min |
| 1 | 100 | 102 | 101 | 101 | 102 | 102 | 89 | 89 | 89 | 88 |
| 2 | 98 | 99 | 99 | 99 | 98 | 98 | 86 | 85 | 86 | 85 |
| 3 | 99 | 99 | 100 | 100 | 100 | 100 | 86 | 87 | 88 | 86 |
| 4 | 97 | 98 | 98 | 98 | 98 | 97 | 84 | 85 | 85 | 84 |
| 5 | 97 | 98 | 98 | 98 | 98 | 98 | 83 | 86 | 86 | 85 |
| 6 | 98 | 99 | 99 | 99 | 99 | 99 | 86 | 87 | 87 | 86 |

TABLE 2.59-continued

Formulation 15 50 mg Tablet Dissolution - Media Exchange

| | Stage | | | | | | | | | |
|---|---|---|---|---|---|---|---|---|---|---|
| | Acid Stage | | | | | | Buffer Stage | | | |
| Replicate | 15 min | 30 min | 45 min | 60 min | 90 min | 120 min | 135 min | 150 min | 165 min | 180 min |
| Average | 98 | 99 | 99 | 99 | 99 | 99 | 86 | 87 | 87 | 86 |
| RSD | 1 | 1 | 1 | 1 | 1 | 2 | 3 | 2 | 2 | 2 |

TABLE 2.60

1 mL Oral Solution Dissolution - Media Exchange

| | Stage | | | | | | | | | |
|---|---|---|---|---|---|---|---|---|---|---|
| | Acid Stage | | | | | | Buffer Stage | | | |
| Replicate | 15 min | 30 min | 45 min | 60 min | 90 min | 120 min | 135 min | 150 min | 165 min | 180 min |
| 1 | 99 | 100 | 100 | 99 | 100 | 100 | 67 | 72 | 73 | 66 |
| 2 | 103 | 102 | 101 | 100 | 100 | 100 | 71 | 73 | 70 | 70 |
| 3 | 101 | 100 | 100 | 101 | 100 | 100 | 67 | 72 | 75 | 70 |
| 4 | 101 | 101 | 101 | 100 | 100 | 100 | 69 | 69 | 68 | 65 |
| 5 | 104 | 102 | 102 | 103 | 102 | 101 | 71 | 73 | 72 | 65 |
| 6 | 102 | 103 | 102 | 102 | 102 | 102 | 70 | 72 | 73 | 69 |
| Average | 102 | 101 | 101 | 101 | 101 | 101 | 69 | 72 | 72 | 68 |
| RSD | 1 | 1 | 1 | 1 | 1 | 1 | 3 | 2 | 4 | 4 |

TABLE 2.61

5 mL Oral Solution Dissolution - Media Exchange

| | Stage | | | | | | | | | |
|---|---|---|---|---|---|---|---|---|---|---|
| | Acid Stage | | | | | | Buffer Stage | | | |
| Replicate | 15 min | 30 min | 45 min | 60 min | 90 min | 120 min | 135 min | 150 min | 165 min | 180 min |
| 1 | 104 | 104 | 104 | 104 | 105 | 105 | 93 | 94 | 94 | 94 |
| 2 | 100 | 101 | 101 | 101 | 101 | 101 | 91 | 92 | 91 | 91 |
| 3 | 100 | 101 | 101 | 101 | 101 | 102 | 90 | 92 | 91 | 91 |
| 4 | 102 | 103 | 102 | 103 | 103 | 103 | 92 | 92 | 92 | 91 |
| 5 | 102 | 102 | 102 | 102 | 102 | 102 | 88 | 92 | 91 | 90 |
| 6 | 100 | 102 | 102 | 102 | 102 | 102 | 90 | 91 | 92 | 91 |
| Average | 101 | 102 | 102 | 102 | 102 | 102 | 91 | 92 | 92 | 91 |
| RSD | 2 | 1 | 1 | 1 | 1 | 1 | 2 | 1 | 1 | 2 |

Example 3. Tablet Formulation and Manufacturing Process

Figure 39:
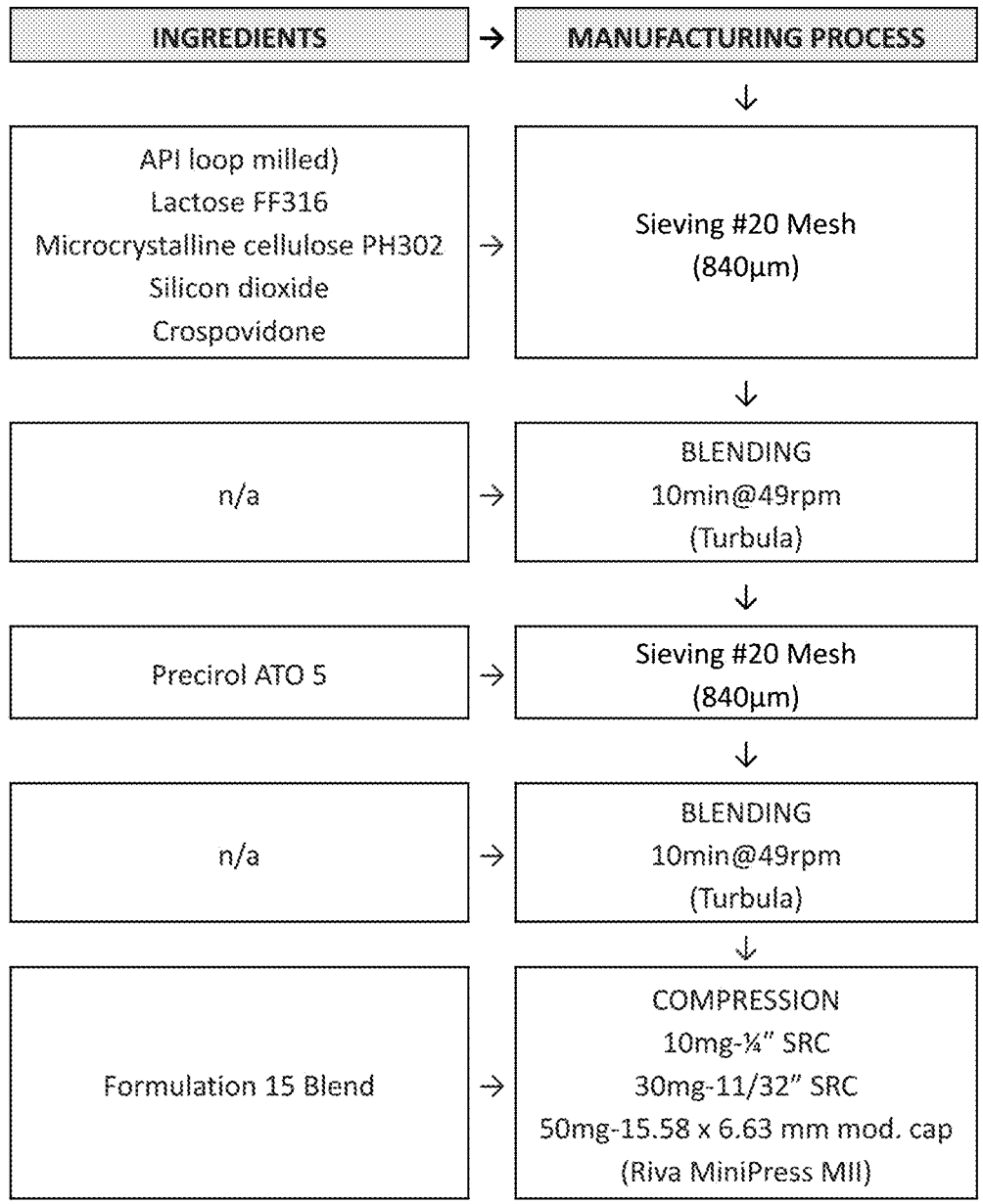
FIG. 39 shows Formulation 15 lab-scale manufacturing process.

This section encompasses the tablet formulation and manufacturing process from the lab-scale formulation development activities. FIG. 39 shows the formulation lab-scale manufacturing process of Formulation 15. Advantageously, the process can be scaled up to suit the needs for commercial-scale production.

The present application is not to be limited in scope by the specific embodiments described herein. Indeed, various modifications of the embodiments in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A pharmaceutical composition comprising maralixibat, or a pharmaceutically acceptable salt thereof, and:
   (i) a diluent selected from the group consisting of dextrates, dextrin, dextrose, lactose, lactose monohydrate, mannitol, sorbitol, cellulose, modified celluloses, and any combination thereof;
   (ii) a glidant selected from the group consisting of silicon dioxide, magnesium stearate, talc, and any combinations thereof;

(iii) a lubricant that is glyceryl palmitostearate in an amount of from about 6% to about 12% (w/w); and
(iv) a disintegrant selected from the group consisting of croscarmellose sodium, crospovidone, starch, sodium starch glycolate, and any combinations thereof in an amount of from about 1% to about 10% (w/w).

2. The composition of claim 1, comprising maralixibat, or a pharmaceutically acceptable salt thereof, and:
(i) the diluent selected from the group consisting of dextrates, dextrin, dextrose, lactose, lactose monohydrate, mannitol, sorbitol, cellulose, modified celluloses, and any combination thereof;
(ii) the glidant selected from the group consisting of silicon dioxide, magnesium stearate, talc, and any combinations thereof in an amount of from about 0.1% to about 2% (w/w);
(iii) the lubricant that is glyceryl palmitostearate in an amount of from about 6% to about 12% (w/w); and
(iv) the disintegrant selected from the group consisting of croscarmellose sodium, crospovidone, starch, sodium starch glycolate, and any combinations thereof in an amount of from about 3% to about 7% (w/w).

3. The composition of claim 1, wherein the composition is formulated as a solid dosage form.

4. The composition of claim 1, wherein the composition is formulated as a capsule, a pill, a cachet, a tablet, a granule, a multi-particulate, a mini-tablet, or a powder.

5. The composition of claim 4, wherein the composition is formulated as a tablet.

6. The composition of claim 1, wherein the composition comprises from about 5 mg to about 50 mg of maralixibat or a pharmaceutically acceptable salt thereof based on the free base weight of maralixibat.

7. The composition of claim 1, wherein the composition comprises from about 10% to about 25% (w/w) of maralixibat or a pharmaceutically acceptable salt thereof based on the free base weight of maralixibat.

8. The composition of claim 1, wherein the composition comprises maralixibat chloride.

9. The composition of claim 1, wherein the maralixibat, or a pharmaceutically acceptable salt thereof is loop milled or pin milled.

10. The composition of claim 1, wherein the maralixibat, or a pharmaceutically acceptable salt thereof has a particle size distribution characterized by Dv90 of less than about 850 µm in diameter measured by laser diffraction.

11. The composition of claim 1, wherein the maralixibat, or a pharmaceutically acceptable salt thereof has a particle size distribution characterized by Dv90 of less than about 100 µm in diameter measured by laser diffraction.

12. The composition of claim 1, wherein:
a) the disintegrant is selected from the group consisting of croscarmellose sodium, crospovidone, and any combinations thereof;
b) the glidant is selected from the group consisting of silicon dioxide, talc, and any combinations thereof; and
c) the diluent is selected from the group consisting of lactose, lactose monohydrate, cellulose, modified celluloses, mannitol, and any combination thereof.

13. The composition of claim 12, wherein:
a) the disintegrant is crospovidone,
b) the glidant is silicon dioxide, and
c) the diluent is selected from the group consisting of microcrystalline cellulose (MCC), lactose monohydrate, mannitol, and a combination thereof.

14. The composition of claim 1, consisting of about 10.5% (w/w) of maralixibat chloride and
(i) about 50% (w/w) of MCC and about 25% (w/w) of lactose monohydrate;
(ii) about 0.5% (w/w) of silicon dioxide;
(iii) about 9% (w/w) of glyceryl palmitostearate; and
(iv) about 5% (w/w) of crospovidone.

15. The composition of claim 1, consisting of about 9.8% (w/w) of maralixibat chloride and
(i) about 55.2% (w/w) of MCC and about 21.0% (w/w) of lactose monohydrate;
11 about 0.5% (w/w) of silicon dioxide;
(iii) about 8.6% (w/w) of glyceryl palmitostearate; and
(iv) about 5.0% (w/w) of crospovidone.

16. A method of preparing the pharmaceutical composition of claim 1, comprising:
milling maralixibat, or a pharmaceutically acceptable salt thereof;
combining the milled maralixibat, or a pharmaceutically acceptable salt thereof, with the diluent, the glidant, the lubricant; and optionally the disintegrant to form an admixture; and
compacting the admixture to form the pharmaceutical composition.

17. A method of treating cholestatic pruritus in a subject in need thereof, comprising administering to the subject a therapeutically effective amount of the pharmaceutical composition of claim 1.

18. The method of claim 17, wherein the cholestatic pruritus is associated with Alagille syndrome, wherein the subject has Alagille syndrome, wherein the subject is a pediatric subject between 2 months and 18 years of age, or wherein the subject is an adult who is 18 years of age or older.

19. A method of treating cholestatic liver disease or condition in a subject in need thereof, comprising administering to the subject a therapeutically effective amount of the pharmaceutical composition of claim 1.

20. The method of claim 19, wherein the cholestatic liver disease or condition is selected from the group consisting of obstructive cholestasis, non-obstructive cholestasis, extrahepatic cholestasis, intrahepatic cholestasis, primary intrahepatic cholestasis, secondary intrahepatic cholestasis, progressive familial intrahepatic cholestasis (PFIC), PFIC type 1, PFIC type 2, PFIC type 3, PFIC type 4, PFIC type 5, PFIC type 6, benign recurrent intrahepatic cholestasis (BRIC), BRIC type 1, BRIC type 2, BRIC type 3, total parenteral nutrition associated cholestasis, paraneoplastic cholestasis, Stauffer syndrome, intrahepatic cholestasis of pregnancy, contraceptive-associated cholestasis, drug-associated cholestasis, infection-associated cholestasis, Dubin-Johnson Syndrome, primary biliary cirrhosis, primary sclerosing cholangitis, gallstone disease, Alagille syndrome, Dubin-Johnson Syndrome, biliary atresia, post-Kasai biliary atresia, post-liver transplantation biliary atresia, post-liver transplantation cholestasis, post-liver transplantation associated liver disease, intestinal failure associated liver disease, bile acid mediated liver injury, multidrug resistance-associated protein 2 (MRP2) deficiency syndrome, and neonatal sclerosing cholangitis.

21. An oral dosage form comprising from about 5 mg to about 50 mg of maralixibat, or a pharmaceutically acceptable salt thereof, based on the free base weight of maralixibat, and:
(i) a diluent selected from the group consisting of dextrates, dextrin, dextrose, lactose, lactose monohydrate, mannitol, sorbitol, cellulose, modified celluloses, and any combination thereof;

(ii) a glidant selected from the group consisting of silicon dioxide, magnesium stearate, talc, and any combinations thereof in an amount of from about 0.1% to about 2% (w/w);

(iii) a lubricant that is glyceryl palmitostearate in an amount of from about 6% to about 12% (w/w); and (iv) a disintegrant selected from the group consisting of croscarmellose sodium, crospovidone, starch, sodium starch glycolate, and any combinations thereof in an amount of from about 3% to about 7% (w/w).

22. The dosage form of claim 21, comprising about 10 mg or about 50 mg of maralixibat or a pharmaceutically acceptable salt thereof based on the free base weight of maralixibat.

23. The dosage form of claim 21, wherein the dosage form does not comprise metal ions.

24. The dosage form of claim 21, comprising from about 5 mg to about 50 mg of maralixibat, or a pharmaceutically acceptable salt thereof, based on the free base weight of maralixibat, and:

(i) the diluent that is selected from the group consisting of microcrystalline cellulose (MCC), lactose monohydrate, mannitol, and combinations thereof;

(ii) the glidant that is silicon dioxide in an amount of from about 0.1% to about 2% (w/w);

(iii) the lubricant that is glyceryl palmitostearate in an amount of from about 6% to about 12% (w/w); and (iv) the disintegrant that is crospovidone in an amount of from about 3% to about 7% (w/w).

25. The dosage form of claim 21, comprising about 50 mg of maralixibat, or a pharmaceutically acceptable salt thereof, based on the free base weight of maralixibat, and (i) about 50% (w/w) of MCC and about 25% (w/w) of lactose monohydrate;

(ii) about 0.5% (w/w) of silicon dioxide;

(iii) about 9% (w/w) of glyceryl palmitostearate; and (iv) about 5% (w/w) of crospovidone.

26. A method of treating cholestatic pruritus or a cholestatic liver disease or condition in a subject in need thereof, comprising administering to the subject the dosage form of claim 21.

27. The method of claim 26, wherein the cholestatic pruritus is associated with Alagille syndrome, wherein the subject has Alagille syndrome, wherein the subject is a pediatric subject between 2 months and 18 years of age, or wherein the subject is an adult who is 18 years of age or older.

28. The method of claim 27, wherein the cholestatic liver disease or condition is selected from the group consisting of obstructive cholestasis, non-obstructive cholestasis, extrahepatic cholestasis, intrahepatic cholestasis, primary intrahepatic cholestasis, secondary intrahepatic cholestasis, progressive familial intrahepatic cholestasis (PFIC), PFIC type 1, PFIC type 2, PFIC type 3, PFIC type 4, PFIC type 5, PFIC type 6, benign recurrent intrahepatic cholestasis (BRIC), BRIC type 1, BRIC type 2, BRIC type 3, total parenteral nutrition associated cholestasis, paraneoplastic cholestasis, Stauffer syndrome, intrahepatic cholestasis of pregnancy, contraceptive-associated cholestasis, drug-associated cholestasis, infection-associated cholestasis, Dubin-Johnson Syndrome, primary biliary cirrhosis, primary sclerosing cholangitis, gallstone disease, Alagille syndrome, Dubin-Johnson Syndrome, biliary atresia, post-Kasai biliary atresia, post-liver transplantation biliary atresia, post-liver transplantation cholestasis, post-liver transplantation associated liver disease, intestinal failure associated liver disease, bile acid mediated liver injury, MRP2 deficiency syndrome, and neonatal sclerosing cholangitis.

\* \* \* \* \*